US007534859B2

(12) United States Patent
Messing et al.

(10) Patent No.: US 7,534,859 B2
(45) Date of Patent: May 19, 2009

(54) PROTEIN KINASE C EPSILON AS MODULATOR OF ANXIETY, ALCOHOL CONSUMPTION AND SELF-ADMINISTRATION OF DRUGS OF ABUSE

(75) Inventors: Robert O Messing, Foster City, CA (US); Clyde W Hodge, Chapel Hill, NC (US)

(73) Assignee: The Regents of the University of California, Oakland, CA (US)

( * ) Notice: Subject to any disclaimer, the term of this patent is extended or adjusted under 35 U.S.C. 154(b) by 159 days.

(21) Appl. No.: 11/501,667

(22) Filed: Aug. 8, 2006

(65) Prior Publication Data

US 2007/0039063 A1    Feb. 15, 2007

Related U.S. Application Data

(62) Division of application No. 10/746,049, filed on Dec. 23, 2003, which is a division of application No. 09/340,283, filed on Jun. 25, 1999, now Pat. No. 6,717,030.

(60) Provisional application No. 60/091,755, filed on Jul. 6, 1998, provisional application No. 60/125,995, filed on Mar. 24, 1999.

(51) Int. Cl.
*A61K 38/00* (2006.01)
*C07K 5/00* (2006.01)
*C07K 14/00* (2006.01)
*A01N 43/54* (2006.01)
*A01N 43/62* (2006.01)

(52) U.S. Cl. ................. 530/300; 530/350; 514/2; 514/270; 514/221

(58) Field of Classification Search ............. 530/300, 530/350; 514/2, 221, 270
See application file for complete search history.

(56) References Cited

U.S. PATENT DOCUMENTS

| | | | |
|---|---|---|---|
| 5,141,957 A | 8/1992 | Jiang et al. | 514/510 |
| 5,216,014 A | 6/1993 | Jiang et al. | 514/455 |
| 5,270,310 A | 12/1993 | Bell et al. | 514/238.2 |
| 5,292,737 A | 3/1994 | Defauw | 514/247 |
| 5,344,841 A | 9/1994 | Jiang et al. | 514/459 |
| 5,360,818 A | 11/1994 | Jiang et al. | 514/459 |
| 5,432,198 A | 7/1995 | Jagdmann, Jr. | 514/544 |
| 5,464,764 A | 11/1995 | Capecchi et al. | 435/172.3 |
| 5,783,405 A | 7/1998 | Mochly-Rosen et al. | 435/15 |

FOREIGN PATENT DOCUMENTS

WO    WO 97/25861    7/1997

WO    WO 98/17299    4/1998

OTHER PUBLICATIONS

Johnson et al., 1996, JBC, vol. 271, pp. 24962-24966.*
Chiryo, The Journal of Therapy, (1987), vol. 69, No. 2, p. 697-701. (Including translation of relevant part).
International Preliminary Examination Report, dated Jan. 16, 2001, App No. PCT/US99/15152.
International Search Report, dated Oct. 21, 1999, App No. PCT/US99/1512.
PCT Written Opinion, dated Nov. 9, 2000, App No. PCT/US99/1512.
Yakkyoku, The Journal of Practical Pharmacy, (1997), vol. 48, No. 1, p. 73-82. (Including translation of relevant part.).
Berg, K.A. et al., Molecular Pharmacology 45:826-836, 1994.
Bowers, et al., Mice lacking PKC gamma exhibit decreased anxiety. Behavioral Genetics 30:111-121, 2000 Abstract only.

(Continued)

*Primary Examiner*—Peter Paras, Jr.
*Assistant Examiner*—David Montanari
(74) *Attorney, Agent, or Firm*—Jones Day

(57) ABSTRACT

The present invention is directed to the production of PKC isozyme ε (PKCε)-deficient cells and non-human animals. The present invention is further directed to the identification of PKCε as a target for drugs that reduce anxiety. According to the present invention, PKCε-inhibiting compounds act in synergy with drugs acting at the $GABA_A$ receptor. The present invention is also directed to the use of modulators of PKCε to modulate alcohol consumption, self-administration of other drugs of abuse, and the effects of alcohol consumption as well as the use of inhibitors of PKCε, either alone or in conjunction with allosteric agonists of $GABA_A$ receptors, to treat conditions, such as addiction, withdrawal syndrome, skeletal muscle spasms, convulsive seizures, and epilepsy, that are amenable to treatment by allosteric agonists of $GABA_A$ receptors. Additional aspects of the present invention are diagnostic methods for identifying individuals at risk for becoming alcoholics or abusers of other drugs and kits for performing such diagnostic methods.

The present invention relates to: cells and non-human animals deficient for the PKC isozyme ε (PKCε); the use of PKCε as a target for drugs; the use of inhibitors of PKCε in methods of reducing anxiety and treating conditions associated with insufficient activity of the $GABA_A$ receptor; the use of modulators of PKCε in methods of modulating alcohol consumption, modulating self-administration of other drugs of abuse, and altering the effects of alcohol; pharmaceutical compositions comprising inhibitors of PKCε and allosteric agonists of $GABA_A$ receptors; and the identification of individuals with enhanced susceptibility to alcoholism or other forms of addiction.

4 Claims, 15 Drawing Sheets

OTHER PUBLICATIONS

Bowers et al., Ethanol consumption and behavioral impulsivity are increased in protein kinase c gamma null mutant mice. The Journal of Neuroscience 21:RC180-185, 2001.
Hodge, C.W. et al. Nature Neuroscience 2:997-1002, 1999.
Hogg, Sandy Pharmacology Biochemistry and Bahavior, vol. 54, No. 1, pp. 21-30, 1996.
Nomikos, G.G. and Spyraki, C. Neuropharmacology, vol. 27, No. 7, pp. 691-696, 1988.
Onaivi et al., In vivo ibogaine blockade and in vitro PKC action of cocaine. Annals of NY Acadamy of Science 844:227-224, 1998.
Pass, et al. PKC epsilon activation induces dichotomous cardiac phenotypes and modulates PKC epsilon-RACK interactions and RACK expression. American J of Physiology (Heart Circulation Physiology) 280:H946-955, 2001.
Rogers DC. Behavioral Brain Research 105: 207-217, 1999.
Salzman, C. et al., Harv Rev Psychiatry 1:197-206, 1993.
Stenzel-Poore MP et al. 14:2579-2584, 1994.
Takeishi et al., Transgenic overexpression of constitutively active protein kinase c epsilon concentric cardiac hypertrophy Circulation Research 86:1218-1223, 2000.
Allan et al, "Acute and Chronic Ethanol Treatments Alter GABA Receptor-Operated Chloride Channels," *Pharmacology Biochemistry and Behavior*, 27:665-670, (1987).
Berra et al, "Protein Kinase C ζ Isoform Is Critical for Mitogenic Signal Transduction," *Cell*, 74:555-563, (1993).
Chakravarthy et al, "The Direct Measurement of Protein Kinase C (PKC) Activity in Isolated Membranes Using a Selective Peptide Substrate," *Analytical Biochemistry*, 196:144-150, (1991).
Chakravarthy et al, "Inactive membrane: protein kinase Cs: a possible target for receptor signalling," *Biochem. J.*, 304:809-816, (1994).
Cooper et al, "Antagonism of the Enhanced Susceptibility to Audiogenic Seizures during Alcohol Withdrawal in the Rat by γ-Aminobutyric Acid (GABA) and 'GABA-mimetic' Agents," *The Journal of Pharmacology and Experimental Therapeutics*, 209:396-403, (1979).
Crabbe et al. "Acute Dependence on Depressant Drugs is Determined by Common Genes in Mice," *The Journal of Pharmacology and Experimental Therapeutics*, 257(2):663-667, (1991).
Crabbe et al, "Elevated alcohol consumption in null mutant mice lacking 5-HT$_{1B}$ serotonin receptors," *Nature Genetics*, 14:98-101, (1996).
Crabbe et al, "Genetic Animal Models of Alcohol and Drug Abuse," *Science*, 264(5166):1715-1723, (1994).
Decock et al, "Classical, novel and atypical isoforms of PKC stimulate ANF- and TRE/AP-1-regulated-promoter activity in ventricular cardiomyocytes," *FEBS Letters*, 356:275-278, (1994).
Demarest et al, "Identification of an Acute Ethanol Response Quantitative Trait Locus on Mouse Chromosome-2," *The Journal of Neuroscience*, 19(2):549-561, (1999).
Dewey et al, "A Novel Strategy for the Treatment of Cocaine-Addiction," *Synapse*, 80:119-129, (1998).
Di Chiara et al, "Drugs abused by humans preferentially increase synaptic dopamine concentration in the mesolimbic system of freely moving rate," *Proc. Natl. Acad. Sci. USA*, 85:5274-5278, (1988).
Donzanti et al, "An improved and rapid HPLC-EC-method for the isocratic separation of amino acid neurotransmitters from brain tissue and microdialysis perfusates," *Life Sciences*, 43:913-922, (1988).
Evans et al, "Establishment in culture of pluripotential cells from mouse embryos," *Nature*, 292:154-156, (1981).
Finn et al, "Temperature Dependence of Ethanol Depression in Mice: Dose-Response," *Alcoholism: Clinical and Experimental Research*, 18(2):382-386, (1994).
Frye et al, "An Evaluation of the Locomotor Stimulating Action of Ethanol in Rats and Mice," *Psychopharmacology*, 75:372-379, (1981).
Frye et al, "Differential Sensitivity of Ethanol Withdrawal Signs in the Rat to γ-Aminobutyric Acid (GABA)Mimetics: Blockade of Audiogenic Seizures But Not Forelimb Tremors," *The Journal of Pharmacology and Experimental Therapeutics*, 226:720-725, (1983).

Gamache et al, "Simultaneous measurement of monoamines, metabolites and amino acids in brain tissue and microdialysis perfusates," *Journal of Chromatography*, 614:213-220, (1993).
Gobert et al, "Simultaneous quantification of serotonin, dopamine and noradrenaline levels in single frontal cortex dialysates of freely-moving rats reveals a complex pattern of reciprocal auto- and heteroreceptor-mediated control of release," *Neuroscience*, 84(2):413-429, (1998).
Goodnight et al, "Selective involvement of protein kinase C isozymes in differentiation and neoplastic transformation," *Advances in Cancer Research*, 64:159-209, (1994).
Gruber et al, "Increased Expression of Protein Kinase C$_\alpha$ Plays a Key Role in Retinoic Acid-induced Melanoma Differentiation," *The Journal of Biological Chemistry*, 267(19):13356-13360, (1992).
Guidotti et al, "Gabaergic Synapses: Supramolecular Organization and Biochemical Regulation," *Neuropharmacology*, 22(12B):1471-1479, (1983).
Harris et al, "Functional Coupling of γ-Aminobutyric Acid Receptors to Chloride Channels in Brain Membranes," *Science*, 228:1108-1110, (1985).
Hauger et al, "Corticotropin-Releasing Factor Receptors and Pituitary Adrenal Responses during Immobilization Stress," *Endocrinology*, 123:396-405, (1988).
Hesselbrock, "The Genetic Epidemiology of Alcoholism," in *The Genetics of Alcoholism*, 17-39, (Begleiter et al., eds., Oxford University Press, 1995).
Hodge et al, "Effects of Intraaccumbens Injections of Dopamine Agonists and Antagonists on Sucrose and Sucrose-Ethanol Reinforced Responding," *Pharmacology Biochemistry and Behavior*, 48(1):141-150, (1994).
Hodge et al, "Increased exploratory behavior and diminished anxiety in mutant mice lacking PKCε," *Society for Neuroscience Abstracts*, 24(1-2):117, (Nov. 1998).
Homanics et al, "Alcohol and anesthetic mechanisms in genetically-engineered mice," *Frontiers in Bioscience*, 3:548-558, (1998).
Hundle et al, "Overexpression of ε-Protein Kinase. C Enhances Nerve Growth Factor-induced Phosphorylation of Mitogen-activated Protein Kinases and Neurite Outgrowth," *The Journal of Biological Chemistry*, 270(50):30134-30140. (1995).
Hundle et al, "An Inhibitory Fragment Derived from Protein Kinase Cε Prevents Enhancement of Nerve Growth Factor Responses by Ethanol and Phorbol Esters," *The Journal of Biological Chemistry*, 272(23):15028-15035, (1997).
Johannes et al, "PKCμ Is a Novel, Atypical Member of the Protein Kinase C Family," *The Journal of Biological Chemistry*, 269(8):6140-6148, (1994).
Jolly et al, "In vivo mictodialysis in the rat: low cost and low labor construction of a small diameter, removable, concentric-style microdialysis probe system," *Journal of Neuroscience Methods*, 68:259-267, (1996).
Kellenberger et al, "Function of the α1β2γ2S γ-Aminobutyric Acid Type A Receptor Is Modulated by Protein Kinase C via Multiple Phosphorylation Sites," *The Journal of Biological Chemistry*, 267(36):25660-25663, (1992).
Kelley et al, "Absence of PKCε produces changes in ethanol and GABA$_A$ agonist-induced sedation in mice," *Society for Neuroscience Abstracts*, 24(1-2):2166, (Nov. 1998).
Kitano et al, "Assay and Purification of Protein Kinase C," *Methods in Enzymology*, 124:349-352, (1986).
Koob et al, "Neuroscience of Addiction," *Neuron*, 21:467-476, (1998).
Krishek et al, "Regulation of GABA$_A$ Receptor Function by Protein Kinase C Phosphorylation," *Neuron*, 12:1081-1095, (1994).
Kushner et al, "Gamma-vinyl GABA attenuates cocaine-induced lowering of brain stimulation reward thresholds," *Psychopharmacology*, 133 (4):383-388, (1997).
Lehel et al, "A Chemiluminescent Microtiter Plate Assay for Sensitive Detection of Protein Kinase Activity," *Analytical Biochemistry*, 244:340-346, (1997).
Lin et al, "Protein Kinase C Enhances Recombinant Bovine α1β1γ2L GABA$_A$ Receptor Whole-Cell Currents Expressed in L929 Fibroblasts," *Neuron*, 13:1421-1431, (1994).

Lovinger et al, "Ethanol Inhibits NMDA-Activated Ion Current in Hippocampal Neurons," *Science*, 243 :1721-1724, (1989).

Macfarlane et al, "Activation of β-Isozyme of Protein Kinase C (PKCβ) Is Necessary and Sufficient for Phorbol Ester-induced Differentiation of HL-60 Promyelocytes," *The Journal of Biological Chemistry*, 269(6) :4327-4331, (1994).

Marszalec et al, "Selective Effects of Alcohols on γ-Aminobutyric Acid A Receptor Subunits Expressed in Human Embryonic Kidney Cells," *The Journal of Pharmacology and Experimental Therapeutics*, 269(1):157-163, (1994).

Mehta et al, "Ethanol Potentiation-of GABAergic Transmission in-Cultured Spinal Cord-Neurons Involves γ-Aminobutyric Acid$_A$-Gated Chloride Channels," *The Journal of Pharmacology and Experimental Therapeutics*, 246(2) :558-564, (1988).

Meiner et al, "Disruption of the acyl-CoA:cholesterol acyltransferase gene in mice: Evidence suggesting multiple cholesterol esterification enzymes, in mammals," *Proc. Natl Acad. Sci. USA*, 93:14041-14046, (1996).

Mello et al, "A Primate Model of Polydrug Abuse: Cocaine and Heroin Combinations," *The Journal of Pharmacology and Experimental Therapeutics*, 274(3) :1325-1337, (1995).

Messing et al, "Chronic Ethanol Exposure Increases Levels of Protein Kinase C δ and ε and Protein Kinase C-mediated Phosphorylation in Cultured Neural Cells," *The Journal of Biological Chemistry*, 266(34) :23428-23432, (1991).

Miyakawa et al, "Fyn-Kinase as a Determinant of Ethanol Sensitivity: Relation to NMDA-Receptor Function," *Science*, 278:698-701, (1997).

Nestler et al, "Molecular and Cellular Basis of Addiction," *Science*, 278(5335) :58-63, (1997).

Nishizuka, "Intracellular Signaling by Hydrolysis of Phospholipids and Activation of Protein Kinase C," *Science*, 258(5082) :607-614, (1992).

Ohmichi et al, "Nerve growth factor activates calcium-insensitive protein kinase C-ε in PC-12 rat pheochromocytoma cells," *Biochem. J.*, 295:767-772, (1993).

Olive et al, "Differential behavioral and neurochemical responses to ethanol in mice lacking protein kinase C-epsilon," *Alcoholism Clinical and Experimental Research*, 23:21a, (1999).

Ono et al, "The Structure, Expression, and Properties of Additional Members of the Protein Kinase C Family," *The Journal of Biological Chemistry*, 263:6927-6932, (1988).

Pahlman et al, "Kinetics and concentration effects of TPA-induced differentiation of cultured human neuroblastoma cells," *Cell Differentiation*, 12:165-170, (1983).

Papadopoulos et al, "Isolation and Characterization of Protein Kinase C from Y-1 Adrenal Cell Cytoskeleton," *The Journal of Cell Biology*, 108:553-567, (1989).

Pennisi, "Enzyme Linked to Alcohol Sensitivity in Mice," *Science*, 278:573, (1997).

Poisbeau et al, "Modulation of Synaptic GABA$_A$ Receptor-Function by PKA and PKC in Adult Hippocampal Neurons," *The Journal of Neuroscience*, 19(2) : 674-683, (1999).

Powell et al, "Protein kinase C isozymes ε and α in murine erythroleukemia cells," *Proc. Natl. Acad. Sci. USA*, 89:147-151, (1992).

Reich et al, "Genome-Wide Search for Genes Affecting the Risk for Alcohol Dependence," *American Journal of Medical Genetics (Neuropsychiatric Genetics)*, 81:207-215, (1998).

Roivainen et al, "Protein kinase C and adaptation to ethanol," in *Toward a Molecular Basis of Alcohol Use and Abuse*, 29-37, (Jansson et al., eds., Birkhauser Verlag, 1994).

Roivainen et al, "Ethanol enhances growth factor activation of mitogen-activated protein kinases by a protein kinase C-dependent mechanism," *Proc. Natl. Acad. Sci. USA*, 92:1891-1895, (1995).

Roivainen et al, "Protein kinase C isozymes that mediate enhancement of neurite outgrowth by ethanol and phorbol esters in PC12 cells," *Brain Research*, 624:85-93, (1993).

Roth et al, "Rat Brain Protein Kinase C: Purification, Antibody Production, and Quantification in Discrete Regions of Hippocampus," *Journal of Neurochemistry*, 52:215-221, (1989).

Sanchez-Perez et al, "Increased acute responses to ethanol and enhanced sensitivity of GABA-A receptors to ethanol and benzodiazepines in PKC epsilon mutant mice," *Alcoholism Clinical and Experimental Research*, 23:12a, (1999).

Sapp et al. "Ethanol-GABA$_A$ Receptor Interactions: A Comparison between Cell Lines and Cerebellar Purkinje Cells," *The Journal of Pharmacology and Experimental Therapeutics*, 284(2) :768-776, (1998).

Schuckit, "Low Level of Response to Alcohol as a Predictor of Future Alcoholism," *Am. J. Psychiatry*, 151:184-189, (1994).

Selbie et al, "Molecular Cloning and Characterization of PKC$_1$, an Atypical Isoform of Protein Kinase C Derived from Insulin-secreting Cells," *The Journal of Biological Chemistry*, 268(32) :24296-24302, (1993).

Sharpe, "Researchers Say Hoechst Drug May Be Treatment for Cocaine, Nicotine Addicts," *Wall Street Journal*, Aug. 5, 1998.

Sigel et al, "Recombinant GABA$_A$ receptor function and ethanol," *FEBS Letters*, 324 (2) :140-142, (1993).

Slawecki et al, "Differential Changes in Sucrose/Ethanol and Sucrose Maintained Responding by Independently Altering Ethanol or Sucrose Concentration," *Alcoholism: Clinical and Experimental Research*, 21(2) :250-260, (1997).

Stewart et al, "Expression of retroviral vectors in transgenic mice obtained by embryo infection," *The EMBO Journal*, 6 (2) :383-388, (1987).

Suen et al, "NMDA receptor subunits in the postsynaptic density of rat brain: expression and phosphorylation by endogenous protein kinases," *Molecular Brain Research*, 59:215-228, (1998).

Uchida et al, "Affinity Chromatography of Protein Kinase C-Phorbol Ester Receptor on Polyacrylamide-immobilized Phosphatidylserine," *The Journal of Biological Chemistry*, 259(20) :12311-12314, (1984).

Valverde et al, "Molecular cloning and characterization of protein kinase D: A target for diacylglycerol and phorbol esters with a distinctive catalytic domain," *Proc. Natl. Acad. Sci. USA*, 91:8572-8576, (1994).

von Melcher et al, "Selective disruption of genes expressed in totipotent embryonal stem cells," *Genes and Development*, 6:919-927, (1992).

Wafford et al, "Genetic Differences in the Ethanol Sensitivity of GABA$_A$ Receptors Expressed in *Xenopus* Oocytes," *Science*, 249:291-293, (1990).

Wafford et al, "Ethanol Sensitivity of the GABA$_A$ Receptor Expressed in Xenopus Oocytes Requires 8 Amino Acids Contained in the γ2L Subunit," *Neuron*, 7:27-33, (1991).

Walton et al, "A Three-Step Purification Procedure for Protein Kinase C: Characterization of the Purified Enzyme," *Analytical Biochemistry*, 161:425-437, (1987).

Weiner et al, "Elevation of Basal Protein Kinase C Activity Increases Ethanol Sensitivity of GABA$_A$ Receptors in Rat Hippocampal CA1 Pyramidal Neurons," *Journal of Neurochemistry*, 68:1949-1959 (1997).

Hofmann et al., "The Potential for Isoenzyme-Selective Modulation of Protein Kinase C," The FASEB Journal, vol. 11:649-669, 1997.

* cited by examiner

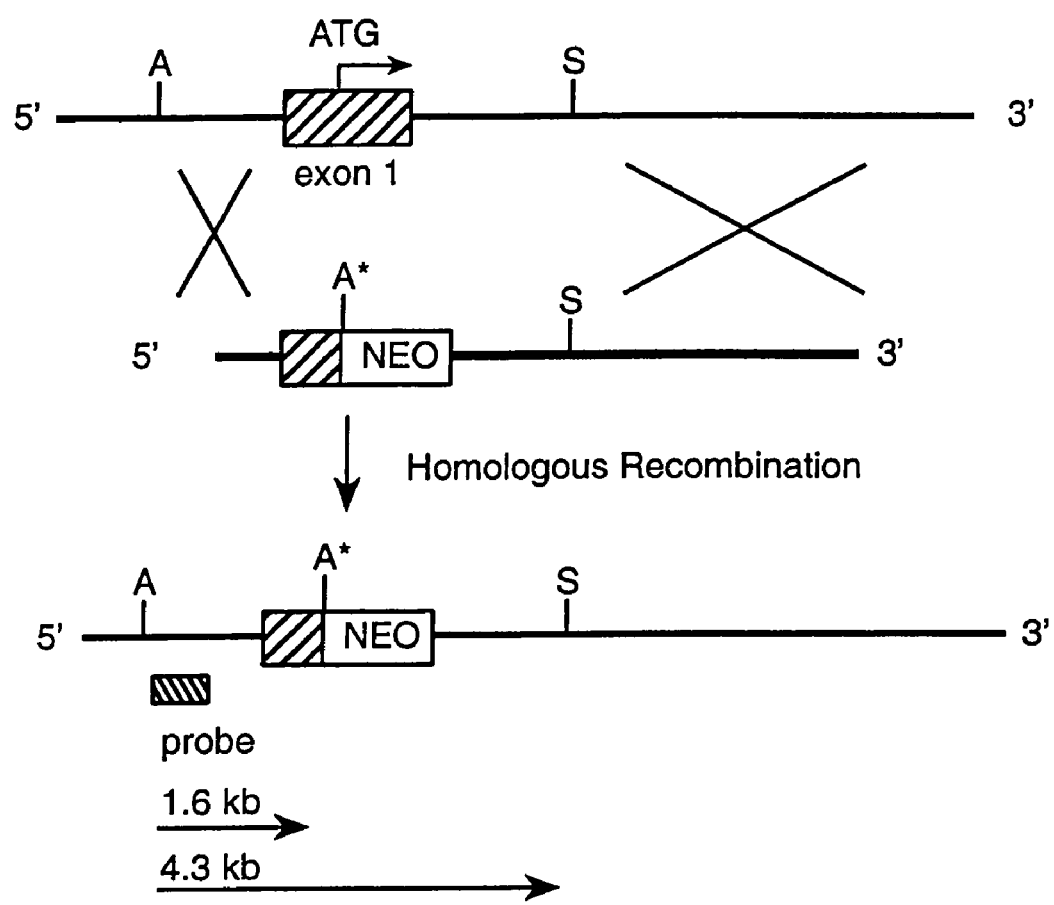
FIG._1A

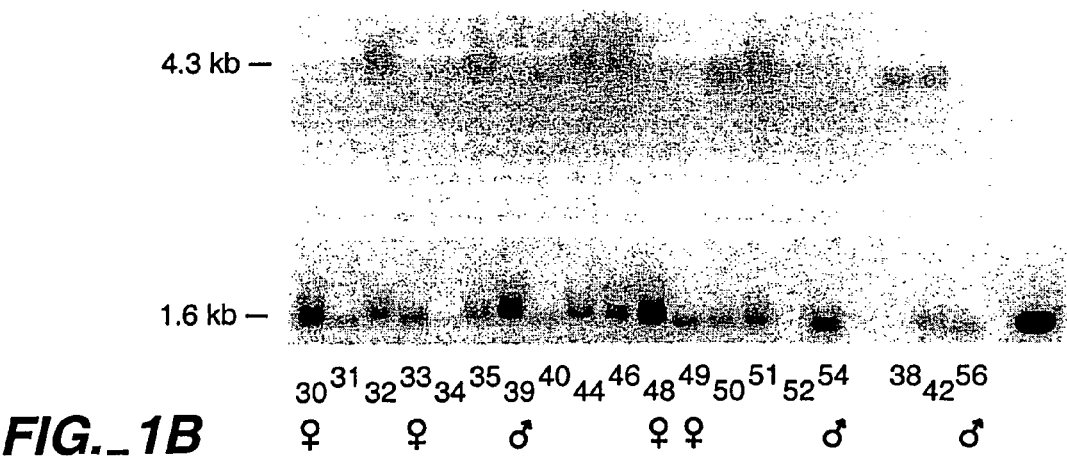
FIG._1B
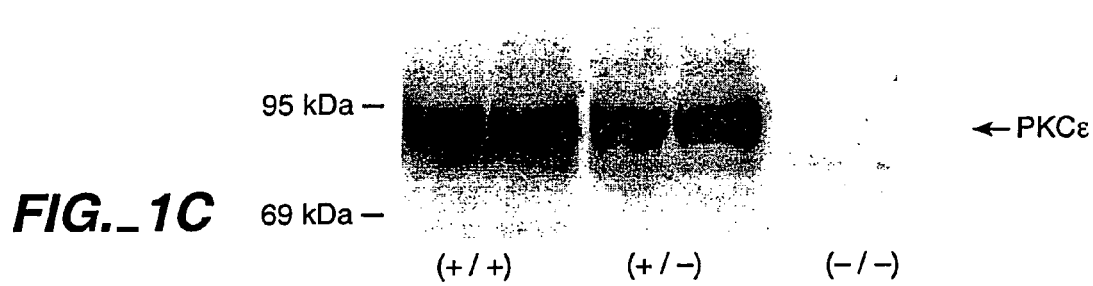
FIG._1C
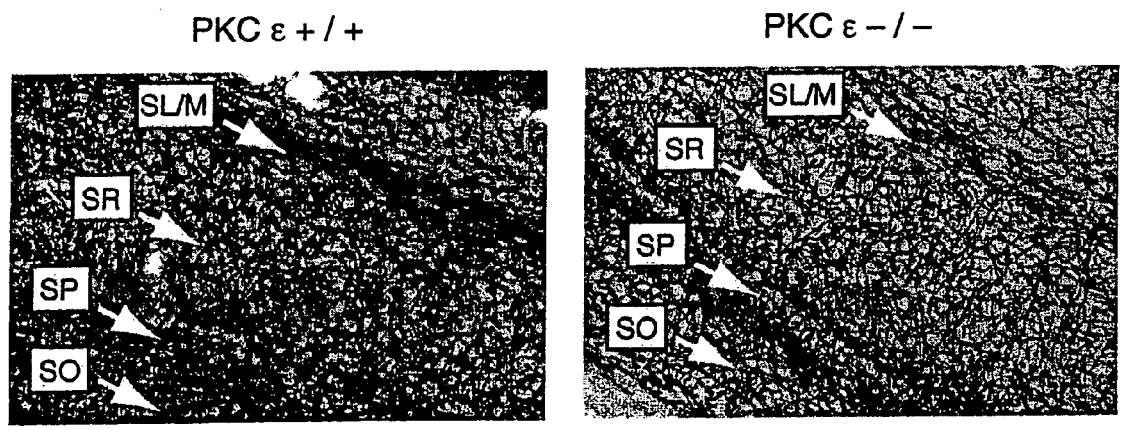
FIG._4A  FIG._4B

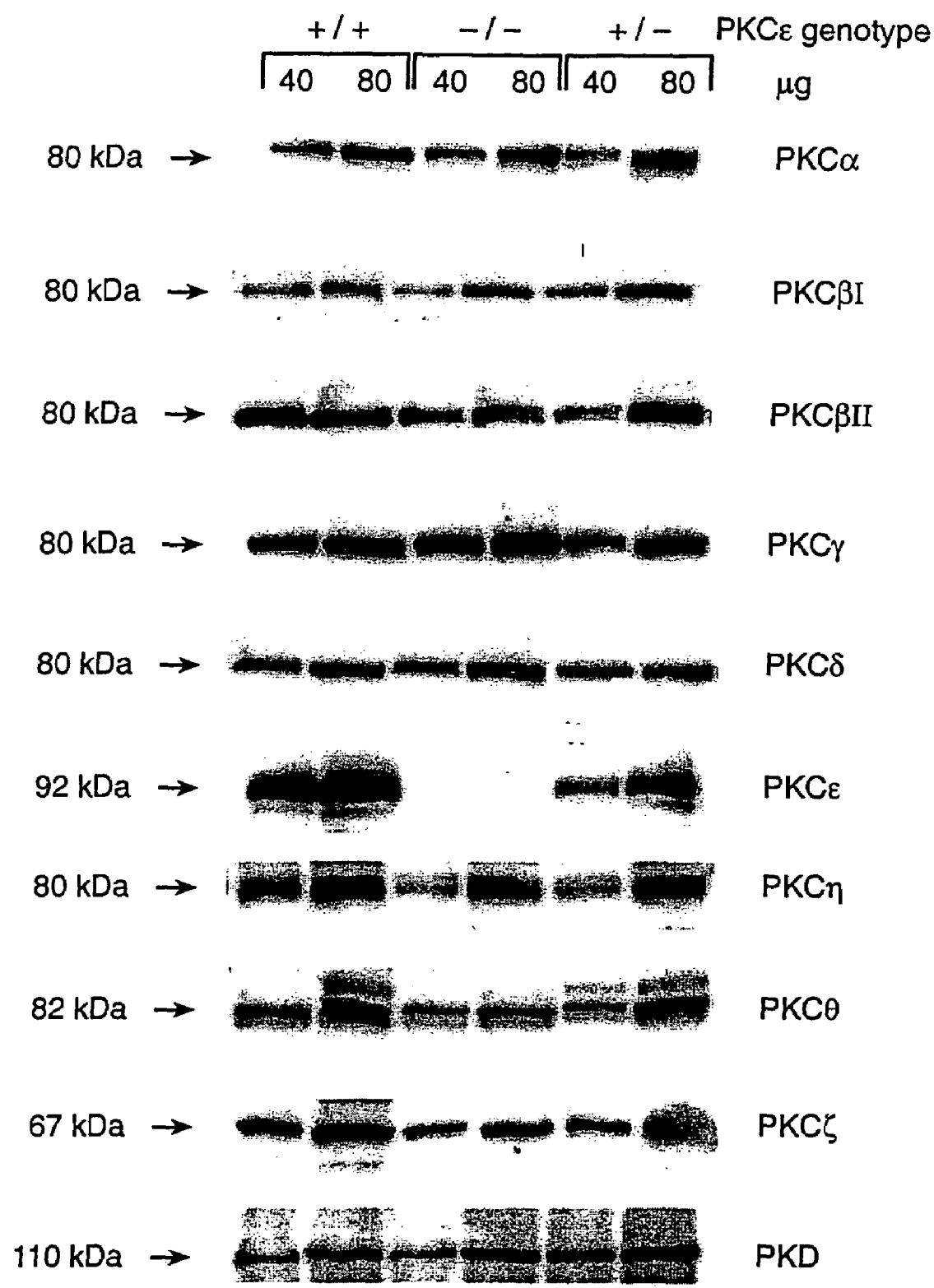
FIG._2

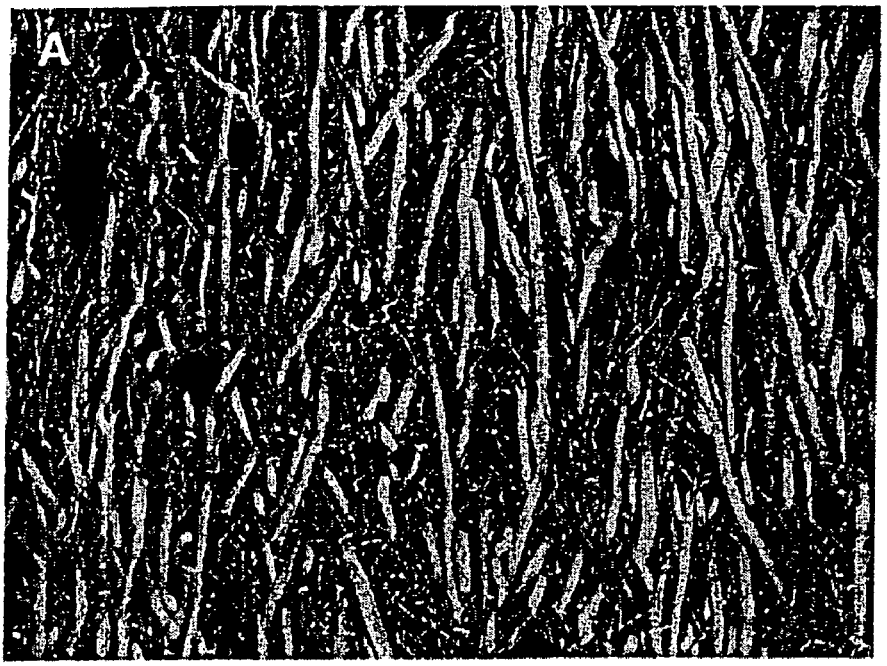
FIG._3A
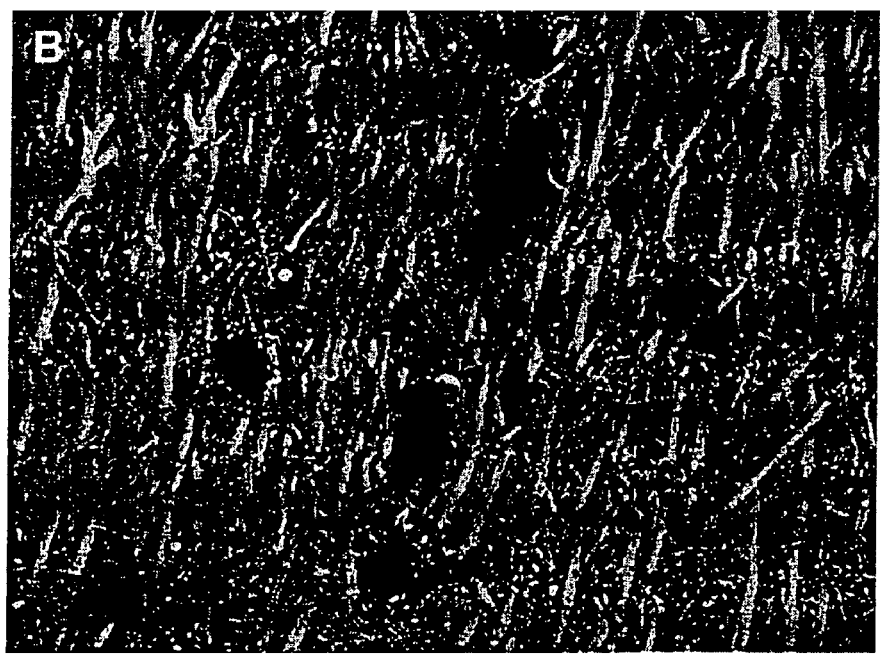
FIG._3B

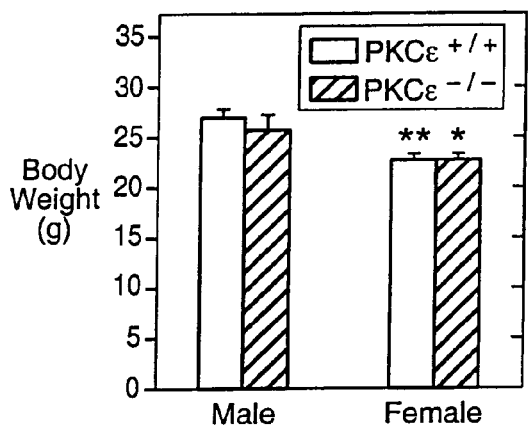
FIG._5A
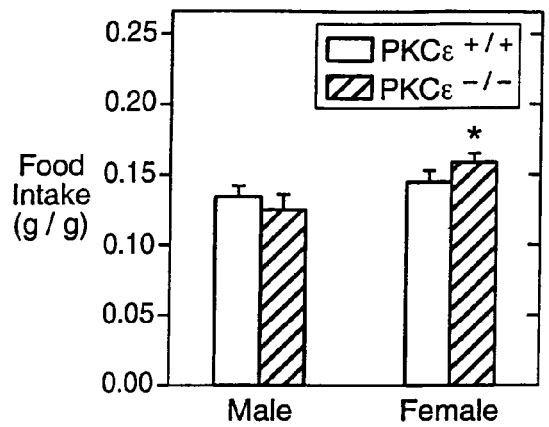
FIG._5B
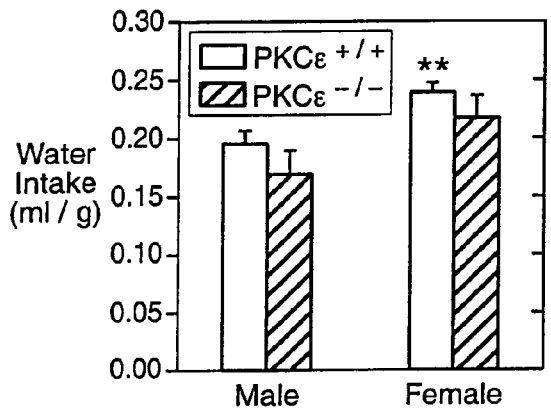
FIG._5C
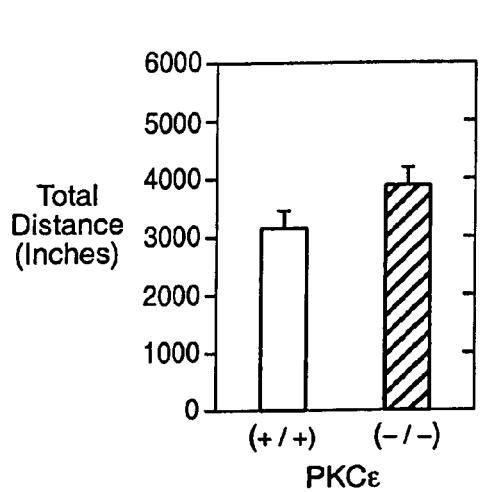
FIG._6A
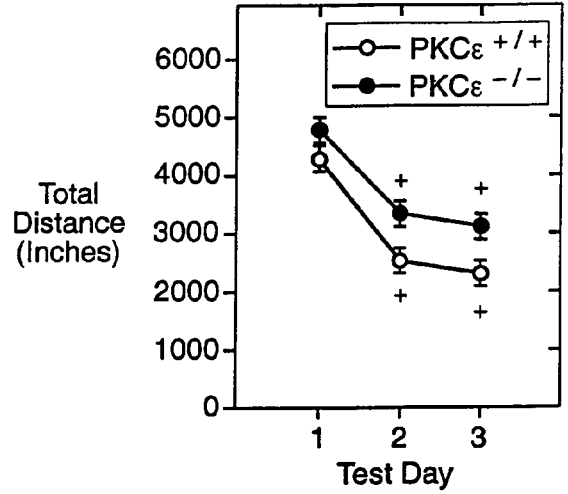
FIG._6B

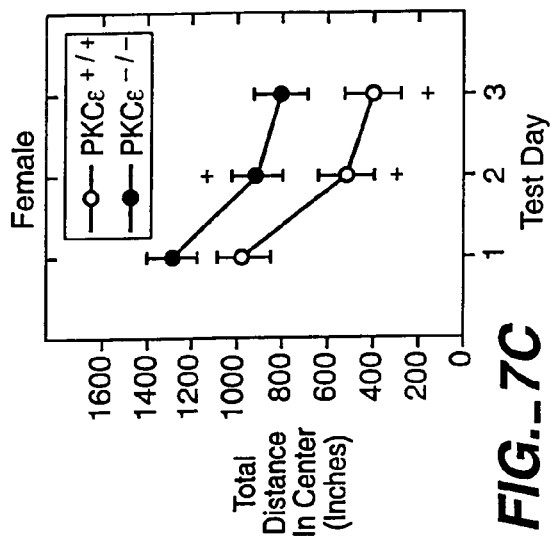
FIG._7C
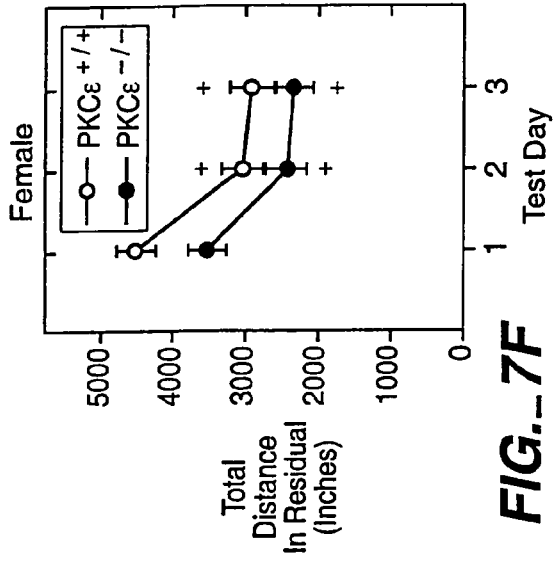
FIG._7F
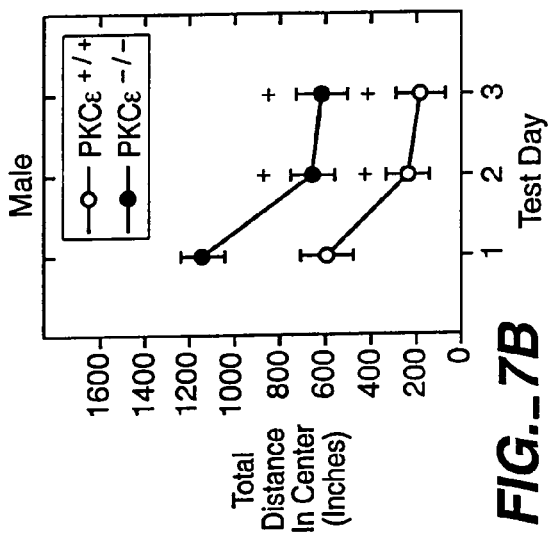
FIG._7B
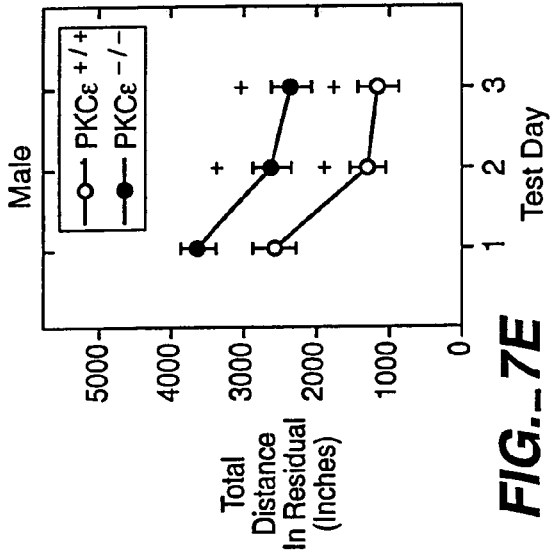
FIG._7E
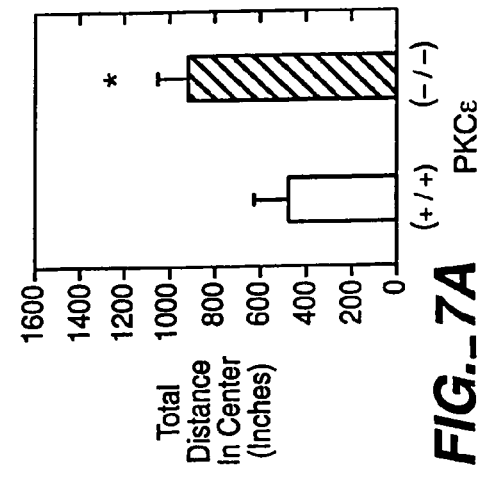
FIG._7A
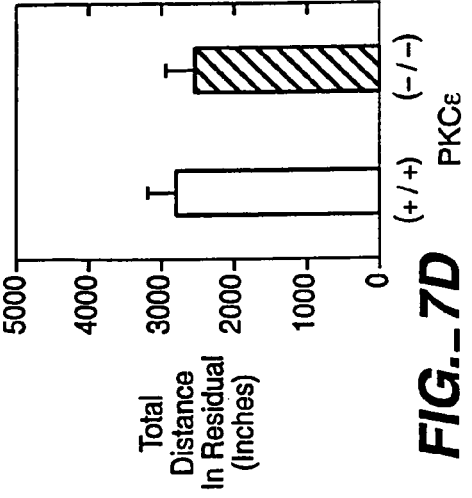
FIG._7D

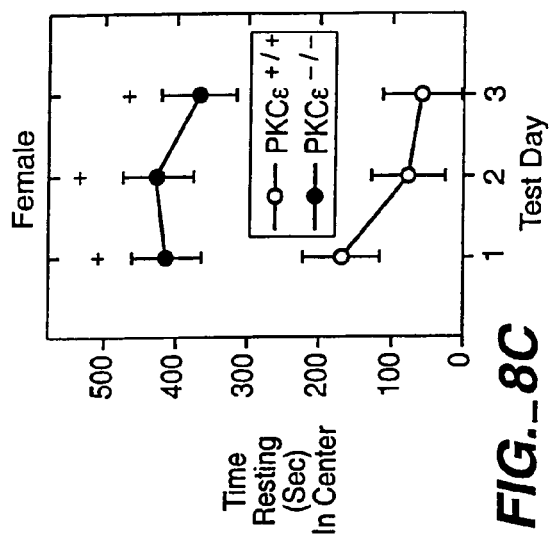
FIG._8C
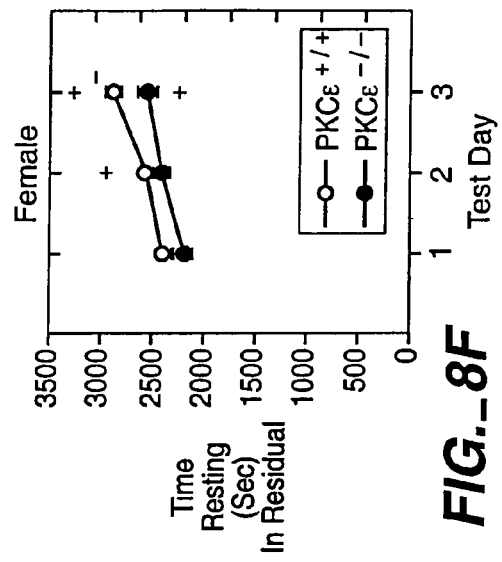
FIG._8F
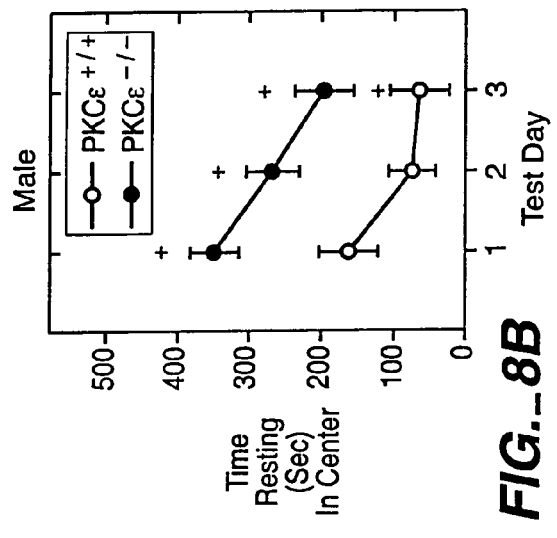
FIG._8B
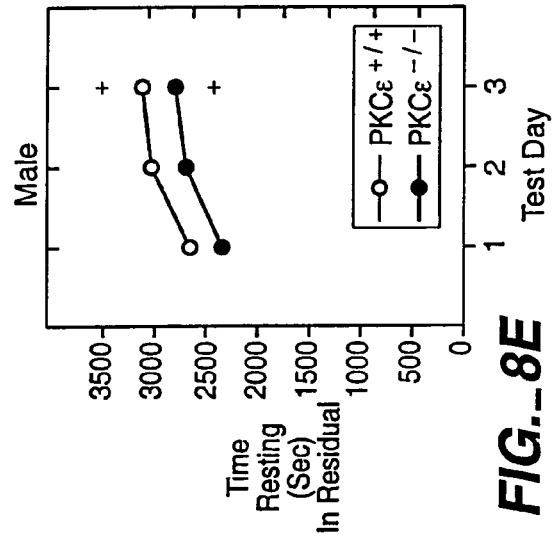
FIG._8E
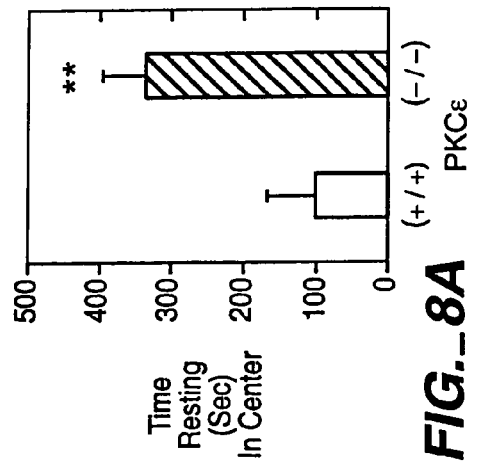
FIG._8A
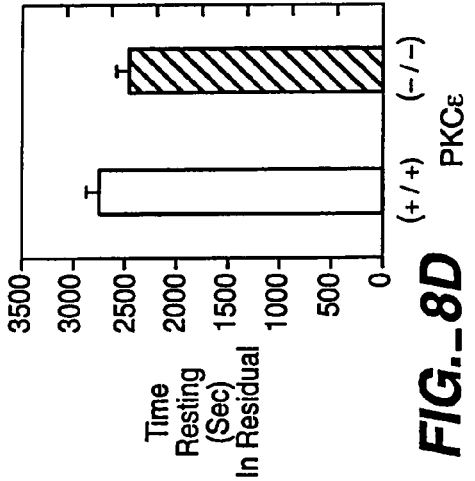
FIG._8D

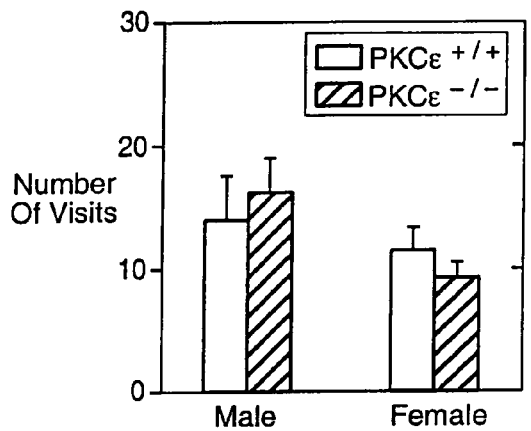
FIG._9A
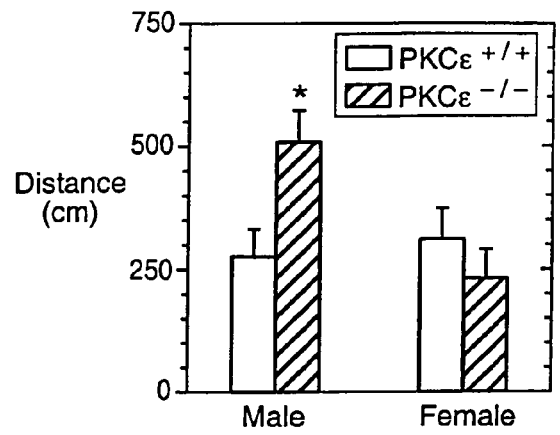
FIG._9B
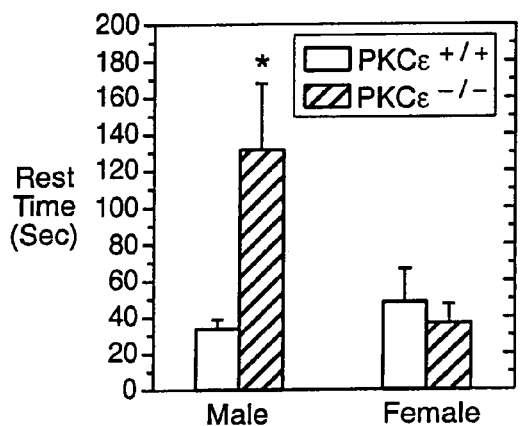
FIG._9C
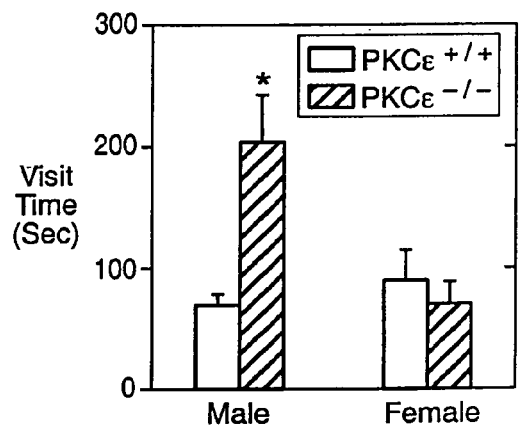
FIG._9D
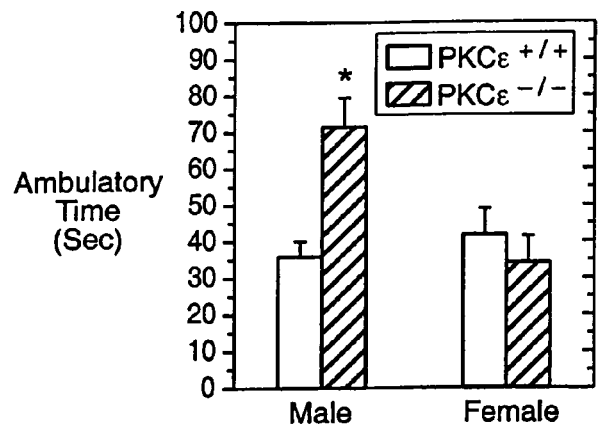
FIG._9E

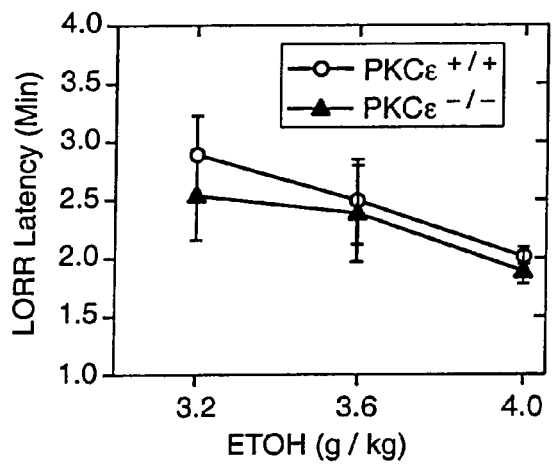
FIG._10A
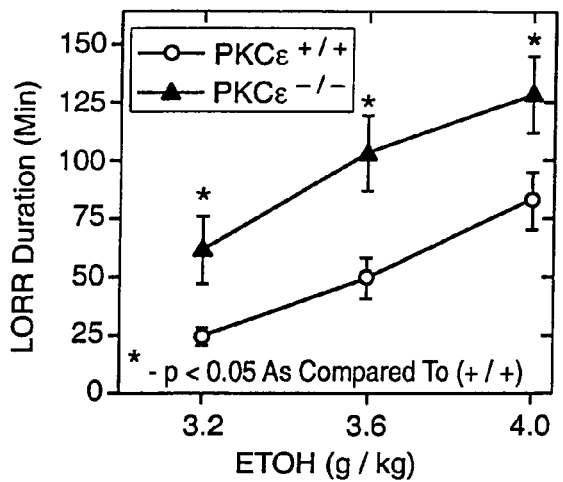
FIG._10B
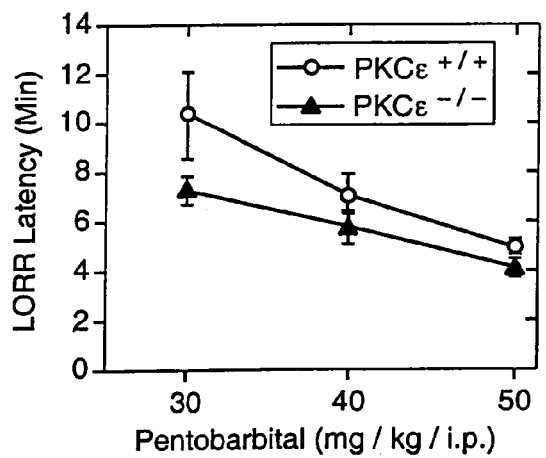
FIG._11A
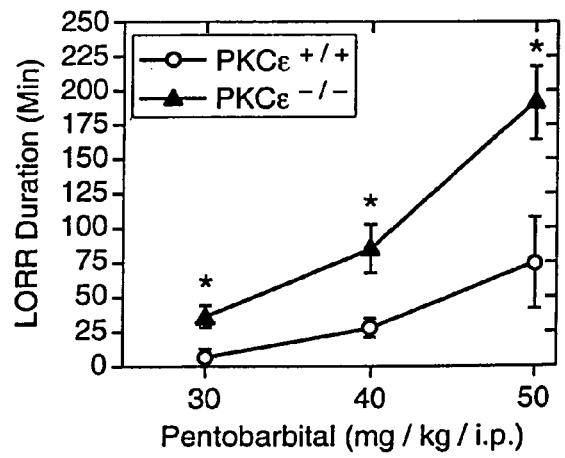
FIG._11B

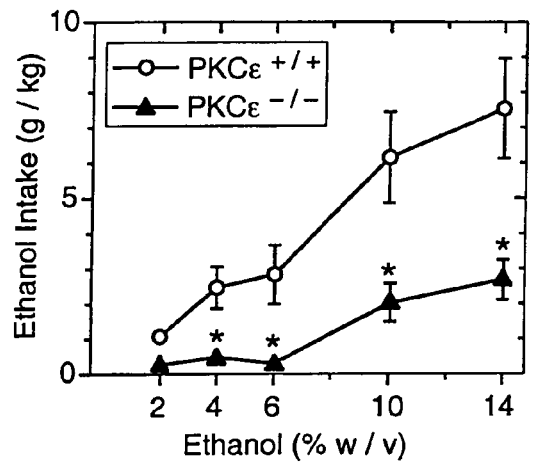
FIG._12A
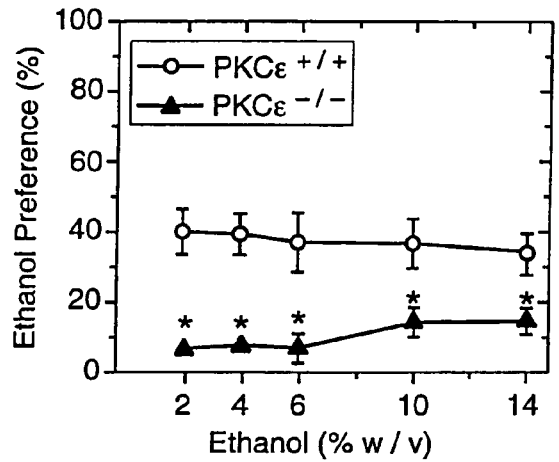
FIG._12B
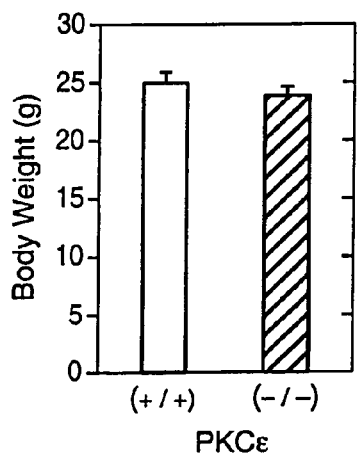
FIG._12C
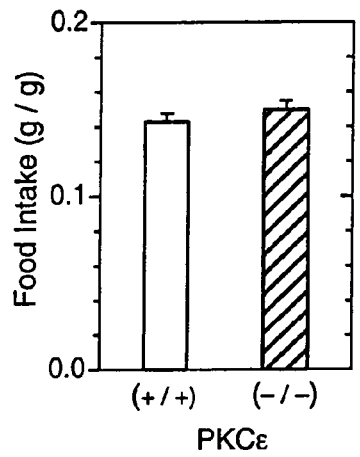
FIG._12D
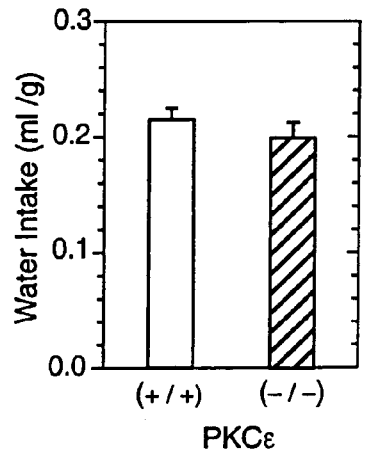
FIG._12E
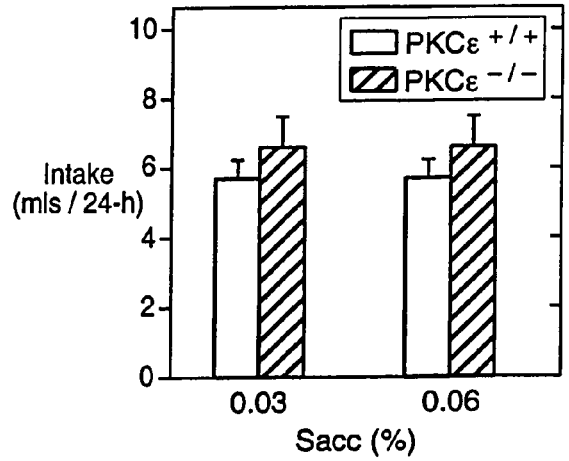
FIG._12F
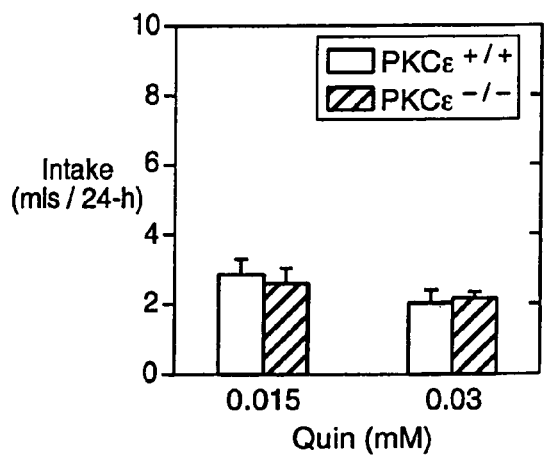
FIG._12G

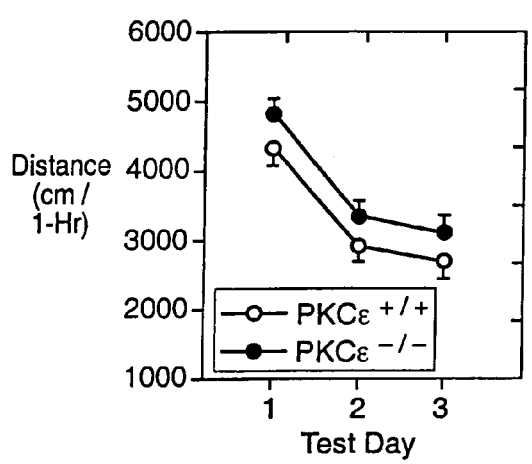
FIG._13A
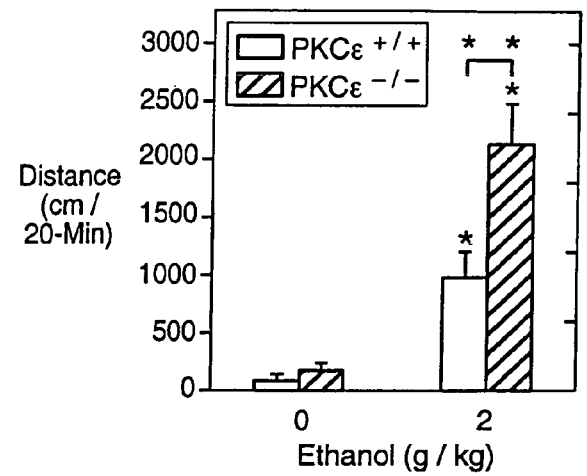
FIG._13B
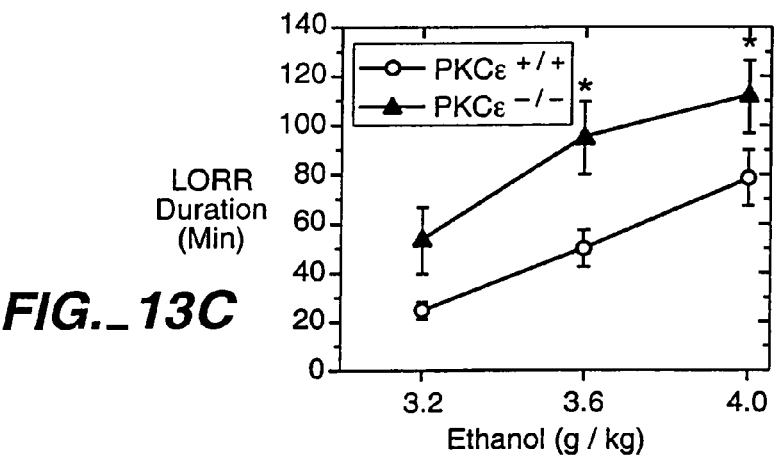
FIG._13C
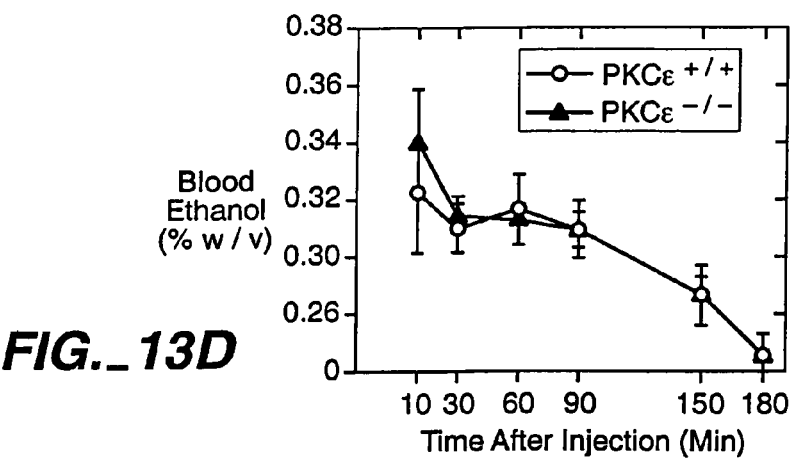
FIG._13D

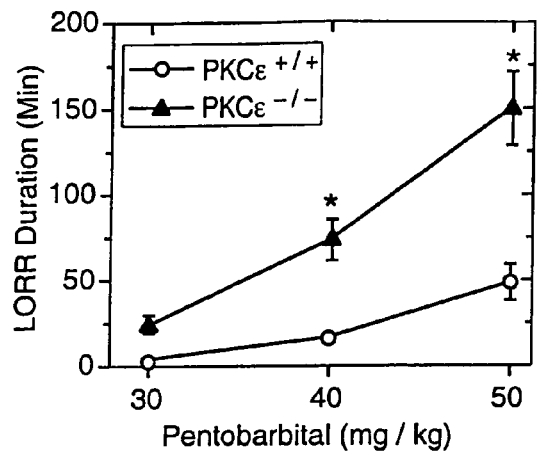
FIG._14A
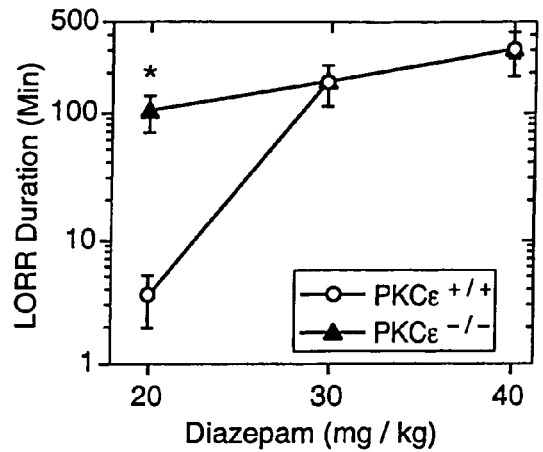
FIG._14B
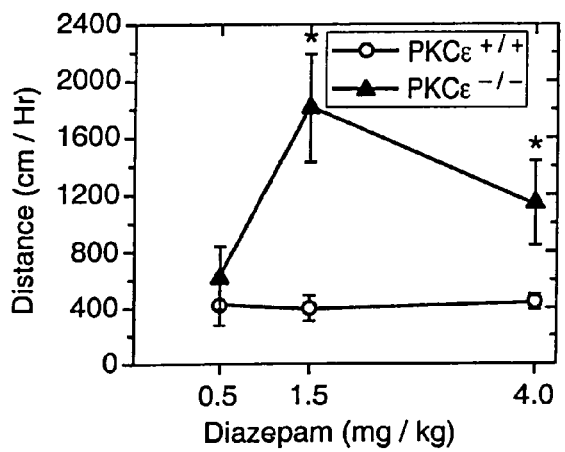
FIG._14C
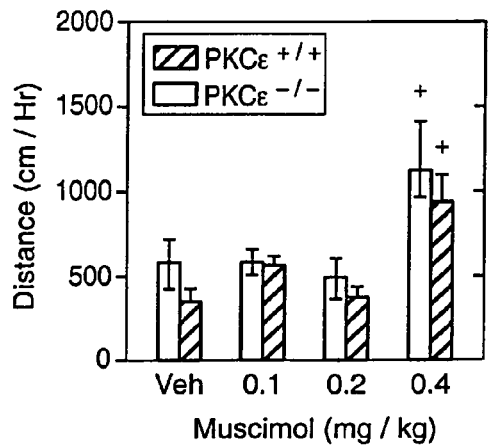
FIG._14D
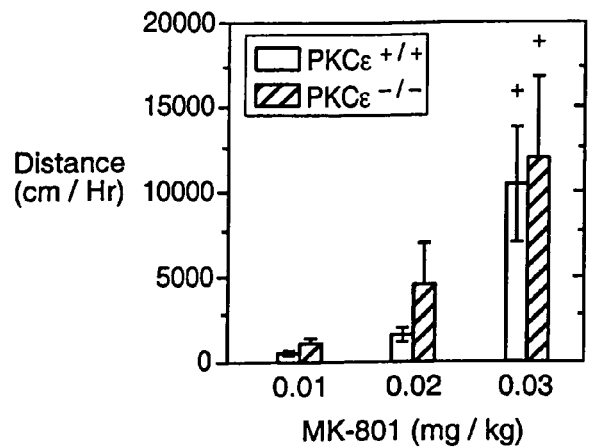
FIG._14E

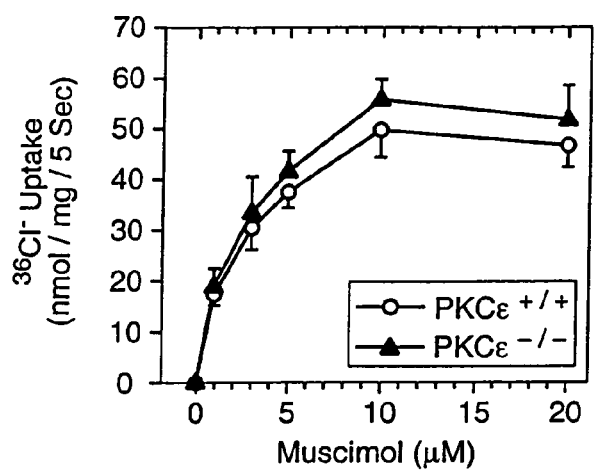
FIG._15A
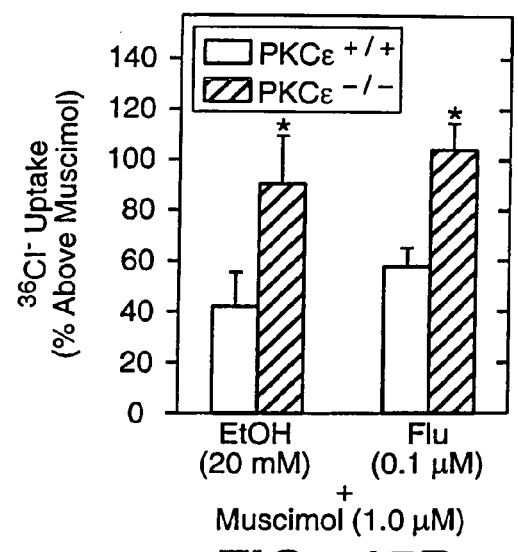
FIG._15B
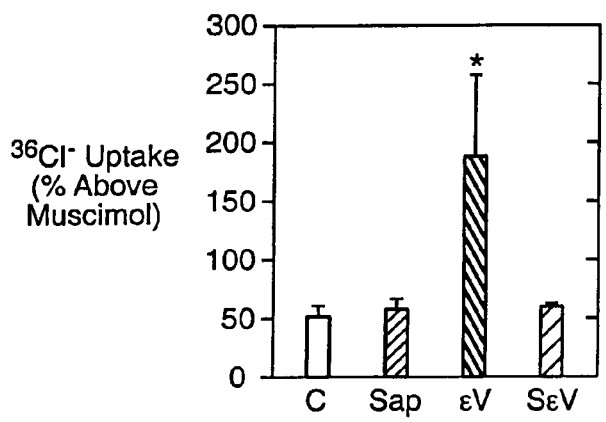
FIG._15C
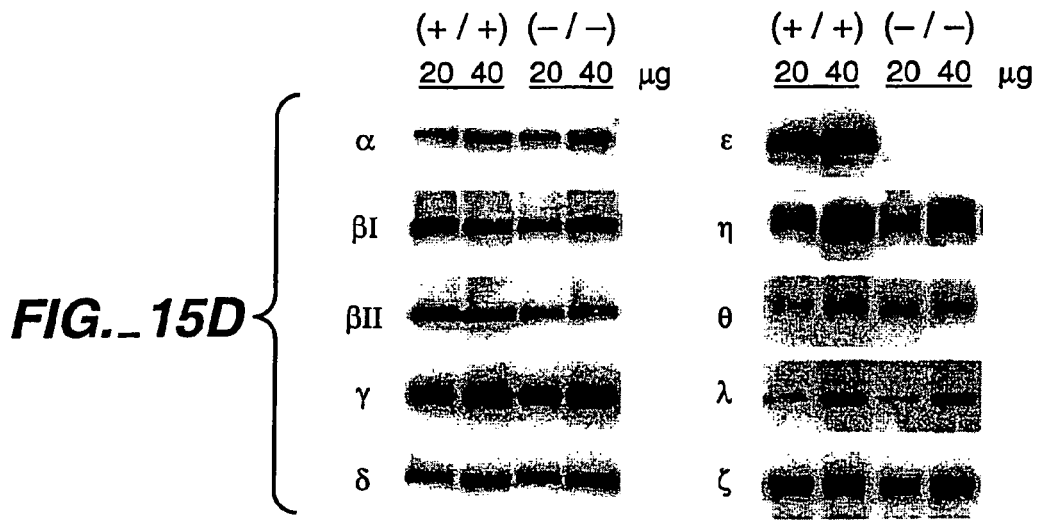
FIG._15D

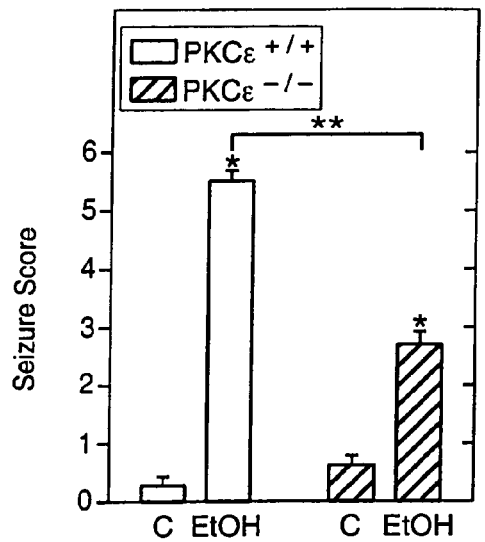
FIG._16
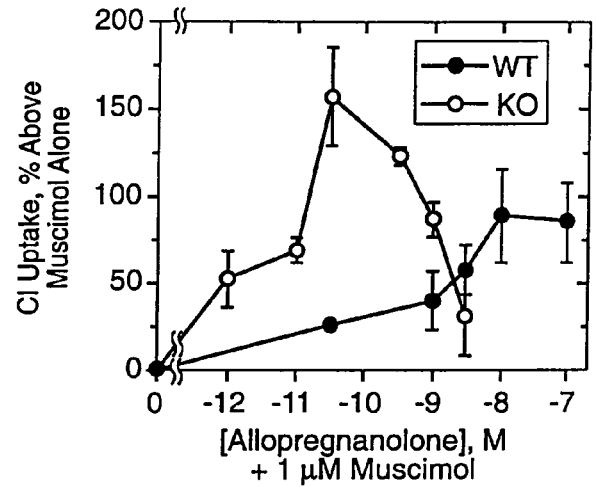
FIG._17
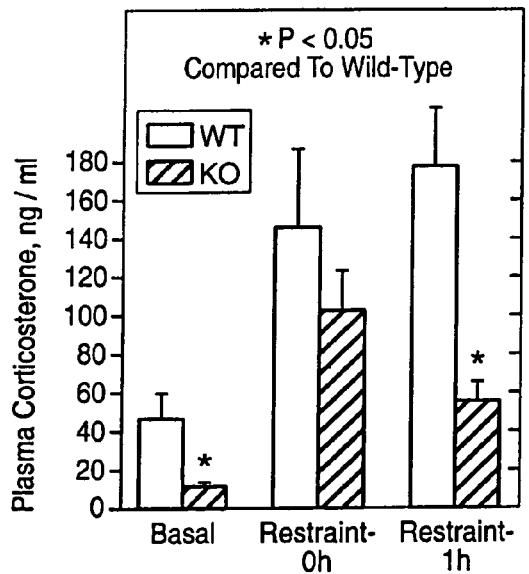
FIG._18
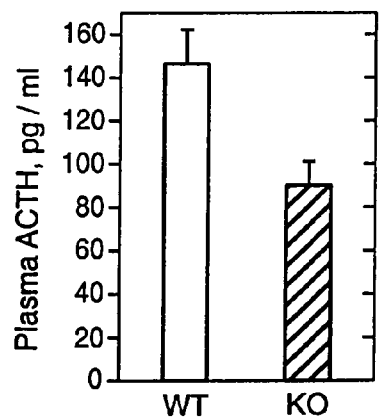
FIG._19

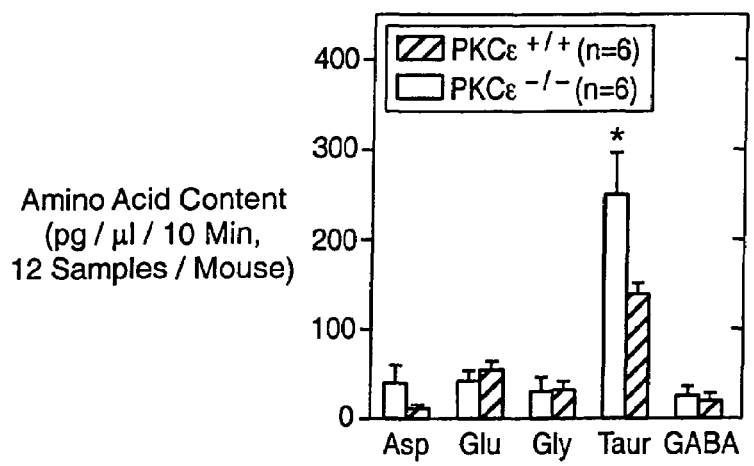
FIG._20
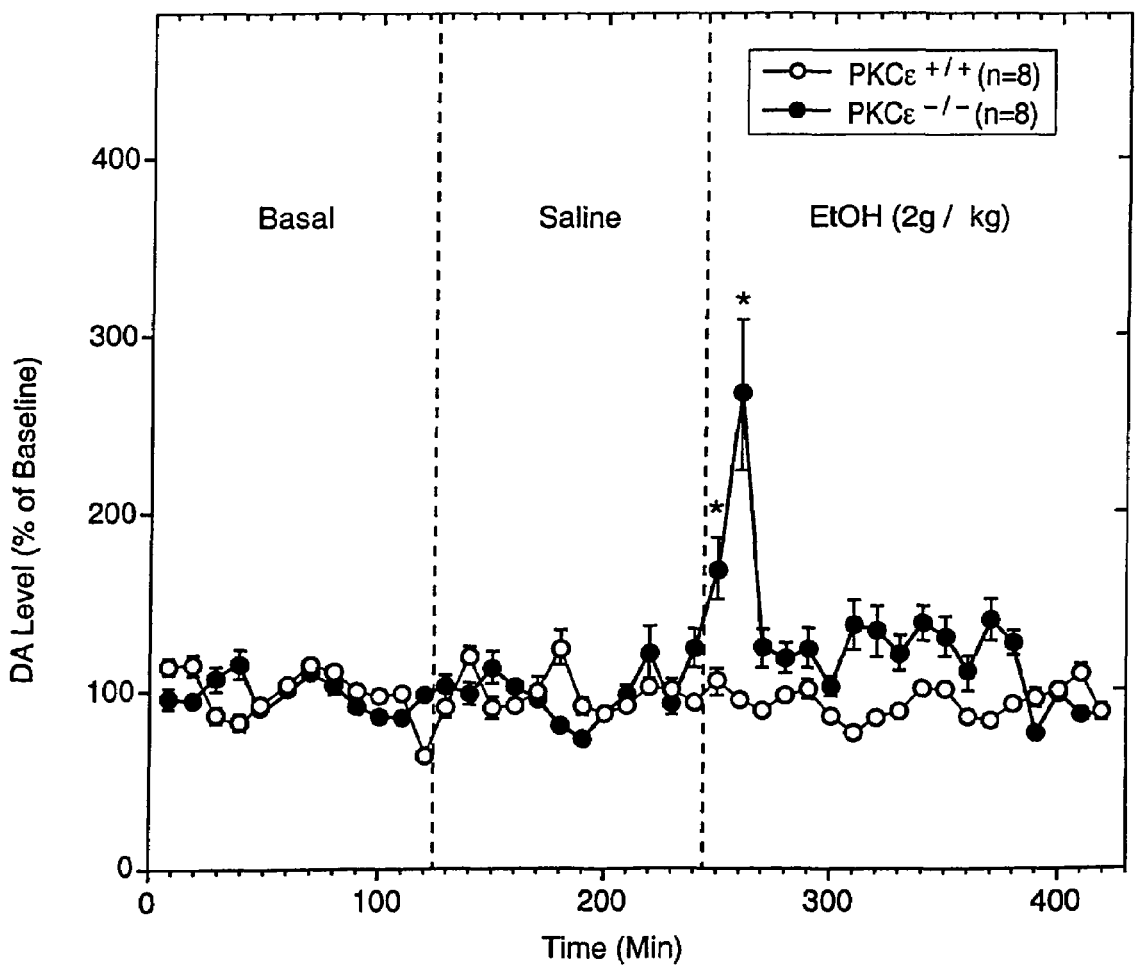
FIG._21

PROTEIN KINASE C EPSILON AS MODULATOR OF ANXIETY, ALCOHOL CONSUMPTION AND SELF-ADMINISTRATION OF DRUGS OF ABUSE

CROSS-REFERENCE TO RELATED APPLICATIONS

This application is a divisional of U.S. application Ser. No. 10/746,049, filed Dec. 23, 2003; which is a divisional of U.S. application Ser. No. 09/340,283, filed Jun. 25, 1999 now U.S. Pat. No. 6,717,030; which claims the benefit of U.S. Provisional Application No. 60/091,755, filed Jul. 6, 1998; and U.S. Provisional Application No. 60/125,995, filed Mar. 24, 1999, the disclosures of each of which are hereby incorporated by reference.

INTRODUCTION

I. Field of the Invention

The present invention relates to: cells and non-human animals deficient for the protein kinase C isozyme ε (PKCε); the use of PKCε as a target for drugs; the use of modulators of PKCε in methods of reducing anxiety, modulating alcohol consumption and self-administration of other drugs of abuse, altering the effects of alcohol, and treating conditions associated with insufficient activity of the $GABA_A$ receptor, and the identification of individuals with enhanced susceptibility to alcoholism or other forms of addiction.

II. Background of the Invention

Anxiety is very common sensation that, if severe or persistent, can be quite disabling. Anxiety-related disorders are so prevalent that benzodiazepines, the most frequently prescribed anxiolytic agents, regularly appear in lists of the top 20 or 25 most frequently prescribed drugs. Given the undesirable side effects of benzodiazepines and other anxiety-reducing drugs, there is a need for new treatments for anxiety.

Alcoholism is the most common form of drug abuse and a major public health problem worldwide. Nevertheless, few drugs exist that modify alcohol intake and the genetic factors that influence alcohol's effects on brain and behavioral processes remain largely uncharacterized. Thus, there is a need for diagnostic tests that can identify individuals with a predisposition to becoming alcoholics and a need for treatments that can alter alcohol consumption.

The Lewin Group estimated the economic cost to U.S. society in 1992 due to alcohol and drug abuse to be $246 billion, $148 billion of which was attributed to alcohol abuse and alcoholism and $98 billion of which stemmed from drug abuse and dependence (H. Harwood et al., The Economic Costs of Alcohol and Drug Abuse in the United States, 1992, NIH Publication Number 98-4327 (September 1998)). When adjusted for inflation and population growth, the alcohol estimates for 1992 are very similar to cost estimates produced over the past 20 years, and the drug estimates demonstrate a steady and strong pattern of increase. The current estimates are significantly greater than the most recent detailed estimates developed for 1985 for alcohol and for drugs (Rice et al. 1990)—42 percent higher for alcohol and 50 percent greater for drugs over and above increases due to population growth and inflation.

Protein kinase C (PKC) is a multigene family of phospholipid-dependent, serine-threonine kinases central to many signal transduction pathways. So far, ten members, i.e., isozymes, of the PKC family have been described, which are encoded by nine different genes. The ten isozymes are designated as the α-, βI, βII, γ-, δ-, ε-, ξ-, η-, ι-, and θ-isozymes. Nishizuka, 1992, *Science* 258:607-614; Selbie et al., 1993, *J. Bio. Chem.* 268:24296-24302. Based on sequence homology and biochemical properties, the PKC gene family has been divided in three groups. A first group, i.e., the α, β1, β2, and γ isozyme, designated as "conventional" PKCs, are regulated by calcium, diacylglycerol and phorbol esters. A second group, i.e., the δ, ε, θ and η isozymes, designated as "novel" PKCs, are calcium-independent, but diacylglycerol and phorbol ester-sensitive. Finally, a third group, i.e., the ξ, and ι isozymes, designated as "atypical" PKCs, are insensitive to calcium, diacylglycerol, and PMA. In addition, two related phospholipid-dependent kinases, PKCμ and protein kinase D, share sequence homology in their regulatory domains to novel PKCs and may constitute a new subgroup. Johannes et al., 1994, *J. Biol. Chem.* 269:6140-6148; Valverde et al., 1994, *Proc. Natl. Acad Sci. USA* 91:8572-8576.

A number of studies with tumor promoting phorbol esters suggest that PKC modulates neural differentiation. For example, phorbol esters induce neural tissue from ectoderm in *Xenopus* embryos (Otte et al., 1988, *Nature* 334:618-620) and elicit neurite outgrowth from chick sensory ganglia (Mehta et al., 1993, *J. Neurochem.* 60:972-98 1, Hsu et al., 1984, *Cancer Res.* 44:4607-4614), chick ciliary ganglion neurons (Bixby, 1989, *Neuron* 3:287-297), several human neuroblastoma cell lines (Pahlman et al., 1983, *Cell Diff.* 12:165-170; Spinelli et al., 1982, *Cancer Res.* 42:5067-5073), and rat PC12 cells (Roivainen et al., 1993, *Brain Res.* 624:85-93; Hall et al. 1988, *J. Biol. Chem.* 263:4460-4466). Studies using purified isozymes, kinase-defective mutants, and transgenic or mutant cell lines have implicated PKCα, -β, -δ, -ε, and -ξ in the differentiation of nonneural cells (Berra et al., 1993, *Cell* 74:555-563; Goodnight et al., 1994, *Adv. Cancer Res.* 64:159-209; Gruber et al., 1992, *J. Biol. Chem.* 267:13356-13360; Macfarlane and Manzel, 1994, *J. Biol. Chem.* 269: 4327-4331; Powell et al., 1992, *Proc. Natl. Acad. USA* 89:146-151). Overexpression of PKCα or -β in *Xetnopus* embryos enhances neural induction (Otte and Moon, 1992, *Cell* 68:1021-1029), but little else is known about the identity of specific PKC isozymes that regulate neural differentiation.

Recent evidence suggests that PKCε plays a role in neural differentiation and plasticity. PKCε is expressed predominantly in the nervous system and is particularly abundant in the hippocampus, olfactory tubercle, and layers I and II of cerebral cortex (Saito et al, 1993, *Brain Res.* 607:241-248). Within immunoreactive neurons, it is localized to the Golgi apparatus and to axons and presynaptic nerve terminals (Saito et al., supra). PKCε is activated by growth factors that stimulate neural differentiation such as insulin (Heidereich et al., 1990, *J. Biol. Chem.* 265:15076-15082) and NGF (Ohmichi et al., 1993, *Biochem J.* 295:767-772). In addition, in developing chick brain, it is the major isozyme found in nondividing, differentiating neurons (Mangoura et al., 1993, *J. Neurosci. Res.* 35:488-498).

Further evidence for involvement of PKCε in neural differentiation has come from studies with PC12 cells. PC12 cells are derived from neural crest and, when treated with NGF or fibroblast growth factors, undergo dramatic biochemical and morphological differentiation, developing several characteristics of mature sympathetic neurons. Greene et al., 1991, in: *Culturing Nerve Cells* (Banker, G. and Goslin, K. eds) pp. 207-226, MIT Press, Cambridge, Mass. PKC-activating phorbol esters enhance NGF-induced activation of ERK1 and ERK2 mitogen-activated protein (MAP) kinases and neurite outgrowth in PC12 cells, suggesting that PKC modulates responses to NGF (Rolvainen et al., 1993, supra; Hall et al; 1988, supra; Rolvainen et al., 1995, *Proc. Natl.*

Acad. Sci. USA 92:1891-1895). Studies with ethanol-treated PC12 cells suggested that PKCε is responsible for this effect Like phorbol esters, ethanol increases NGF-induced MAP kinase activation and neurite outgrowth through a PKC-dependent mechanism (Roivainen et al., 1993, supra; Roivainen et al, 1995, supra). Ethanol promotes PKC-mediated phosphorylation in PC12 cells by increasing levels of messenger RNA and protein for two PKC isozymes, PKCδ and PKCε (Messing et al., 1991, *J. Biol. Chem.*, 266:23428-23432; Roivainen et al., 1994, *Toward a Molecular Basis of Alcohol Use and Abuse*, pp. 29-38). Recent data demonstrate that overexpression of PKCε, but not of PKCδ, enhances NGF-induced MAP kinase activation and neurite outgrowth (Hundle et al., 1995, *J. Biol. Chem.* 270:30134-30140). These findings establish PKCε as a positive modulator of neurite growth. They also suggest that PKCε mediates the neurite-promoting effect of ethanol and phorbol esters in PC12 cells.

A recent study suggests that PKCε specifically mediates enhancement of MAP kinase activation and neurite growth by phorbol esters and ethanol in PC12 cells. PKC activation is generally associated with enzyme translocation to lipid containing structures in particulate fractions of cells. Specifically, studies with PC12 cell lines that stably express the fragments εV1 or δV1, which are derived from the first variable domains of PKCε or PKCδ, showed that each fragment selectively inhibited phorbol ester-induced translocation of its corresponding isozyme, indicating that these fragments can function as isozyme-selective translocation inhibitors. NGF-induced MAP kinase phosphorylation and neurite outgrowth are not enhanced by phorbol esters or ethanol in cells expressing εV1, but they are increased by these agents in cells expressing δV1 and in cells transfected with empty vector.

It has been demonstrated that chronic exposure to ethanol increases total PKC activity, high affinity phorbol ester binding and PKC-mediated phosphorylation in PC12 cells (Messing et al., 1991, *J. Biol. Chem.* 266:23428-23432), which is associated with a selective increase in immunoreactivity and mRNA levels for two PKC isozymes, PKCδ and PKCε (Roivainen et al., 1994, Protein kinase C and adaptations to ethanol, in: *Toward a Molecular Basis of Alcohol Use and Abuse*. Jansson B., Jörvall H., Rydberg U., Terenius L., and Vallee B. L., eds. Birkhduser Verlag, Basel, 1994. pp. 29-38). Ethanol does not increase diacylglycerol formation in PC12 cells or alter PKC activity in an in vitro assay using a mixture of PKC isozymes partially purified from rat brain. These findings suggest that chronic exposure to ethanol increases PKC activity by increasing expression of PKCδ and PKCε. Further, it has been demonstrated that PKCε is involved in two ethanol-induced processes in PC12 cells; first, it has been shown that ethanol potentiates NGF-induced activation of mitogen-activated protein kinases and neurite outgrowth in PC12 cells by a PKCε-dependent mechanism (Roivainen et al., 1993, *Brain Res.* 624:85-93, Roivainen et al., 1995, *Proc. Natl. Acad. Sci. USA* 92:1891-1895; Messing et al., 1991, *Brain Res.* 565:301-311); second, evidence suggesting that ethanol increases the number of N-type voltage gated $Ca^{2+}$ channels in PC12 cells and rodent brain by a PKCε-dependent process (Messing et al., *Alcoholism Clinical and Experimental Research* 22: Abstract S26:2 (1998)). Since both neural plasticity (Robinson and Kolb, 1998, *J. Neurosci.* 17:8491-8497) and increases in the activity of $Ca^{2+}$ channels (Messing and Diamond, 1997, Molecular biology of alcohol dependence, in: *The Molecular and Genetic Basis of Neurological Disease*. Rosenberg R., Prusiner S., DiMauro S., and Barchi R., eds. Butterworth-Heinemann, Boston, pp. 1109-1126) may contribute to drug dependence, PKCε may have a behavior-modulating effect.

GABA (gamma amino butyric acid) is the major inhibitory neurotransmitter in the brain and $GABA_A$ receptors are receptor-gated chloride channels. Upon binding GABA, these channels open, allowing chloride to pass in or out of the cell. This tends to hold the membrane potential of the cell at negative values close to the resting membrane potential, thereby preventing the generation of an action potential. Benzodiazepines are a class of drugs commonly used to reduce anxiety. Benzodiazepines bind with high affinty to $GABA_A$ receptors in the central nervous system. DeLorey and Olsen, 1992, *J. Biol. Chem.* 267:16747-16750. Pentobarbital and benzodiazepines such as diazepam allosterically regulate the $GABA_A$ receptor channel, increasing the $Cl^-$ channel open time or the probably of channel opening in response to GABA (A. Guidotti, M. G. Corda, B. C. Wise, F. Vaccarino, E. Costa, *Neuropharmacology* 22, 1471-9 (1983)). GABA-dependent neurotransinission is thereby enhanced. In contrast, muscimol binds competitively to the GABA recognition site on $GABA_A$ receptors and can elevate $Cl^-$ conductance independently of endogenous GABA.

Previous studies have provided conflicting reports regarding PKC regulation of $GABA_A$ receptors. $GABA_A$ receptors are heteropentameric complexes of related subunits, several of which contain consensus sequences for PKC phosphorylation. Moss, 1992, *J. Biol. Chem.* 267:14470-14476. The γ2 subunit of the $GABA_A$ receptor exists in two forms produced by alternate splicing of mRNA, and some studies suggest that the long splice variant ($γ_{2L}$), which contains a unique consensus site for PKC phosphorylation, is specifically required for ethanol sensitivity of $GABA_A$ receptors (Wafford et al., 1990, *Science* 249:291-293; K. A. Wafford, et al., *Neuron* 7, 27-33 (1991); K. A. Wafford, P. J. Whiting, *Febs Letters* 313, 113-7 (1992)). However, others have failed to observe this requirement (W. Marszalec, Y. Kurata, B. J. Hamilton, D. B. Carter, T. Narahashi, *Journal of Pharmacology and Experimental Therapeutics* 269, 157-63 (1994); E. Sigel, R. Baur, P. Malherbe, *FEBS Letters* 324, 140-142 (1993); D. W. Sapp, H. H. Yeh. *Journal of Pharmacology and Experimental Therapeutics* 284, 768-76 (1998)), and mice lacking $γ_{2L}$ show normal behavioral and electrophysiological responses to ethanol (G. E. Homanics, J. J. Quinlan, R. M. Mihalek, L. L. Firestone, *Frontiers in Bioscience* 3, D548-58 (1998)). Phorbol ester treatment of mouse cerebellar microsacs or of *Xenopus oocytes* and human kidney cells expressing $GABA_A$ receptor subunits inhibits receptor activation by GABA or muscimol (B. J. Krishek, et al., *Neuron* 12, 1081-95 (1994); N. J. Leidenheimer, R. A. Harris, *Advances in Biochemical Psychopharmacology* 47, 269-79 (1992); S. Kellenberger, P. Malherbe, E. Sigel, *The Journal of Biological Chemistry* 267, 25660-25663 (1992)). In contrast, an active catalytic domain of PKC enhances GABA-stimulated currents when expressed in fibroblasts or microinjected into CA1 hippocampal pyramidal neurons (P. Poisbeau, M. C. Cheney, M. D. Browning, I. Mody, *Journal of Neuroscience* 19, 674-83 (1999); Y. F. Lin, M. D. Browning, E. M. Dudek, R. L. Macdonald, *Neuron* 13, 1421-1431 (1994)).

As discussed above, prior to the present invention, little was known about the role of PKCε in vivo in alcoholism, anxiety, drug abuse or $GABA_A$ receptor function.

SUMMARY OF THE INVENTION

To study the role of PKCε in vivo in alcoholism, anxiety, drug abuse, $GABA_A$ receptor function, and other processes, the inventors have used gene targeting by homologous recombination to create mutant mice that lack PKCε.

The present invention relates, inter alia, to: 1) the production of PKCε deficient cells and non-human animals; 2) the identification and the use of the PKC isozyme ε (PKCε) as a target for the modulation of anxiety in a mammal; 3) the use of modulators of PKCε to modulate alcohol consumption and self-administration of other drugs of abuse and the effects of alcohol and other drug consumption; 4) the use of inhibitors of PKCε, either alone or in conjunction with allosteric agonists of $GABA_A$ receptors, to treat conditions, such as anxiety, addiction, withdrawal syndrome, skeletal muscle spasms, convulsive seizures, and epilepsy, that are amenable to treatment by allosteric agonists of $GABA_A$ receptors; and 5) a diagnostic method for identifying individuals at risk for becoming alcoholics or abusers of other drugs.

The present invention is based, in part, on the inventors' discovery that PKCε$^{-/-}$ mice have less fear and anxiety than wild-type mice. This suggests that PKCε is a target for the development of anxiety-reducing drugs. Furthermore, the invention is based, in part, on the inventors' discovery that PKCε$^{-/-}$ mice sleep twice as long as wild-type mice when injected intraperitoneally with drugs that act at $GABA_A$ receptors, such as ethanol, pentobarbital or benzodiazepines. This result suggests that PKCε$^{-/-}$ mice are hypersensitive to the sedative-hypnotic effects of compounds acting at $GABA_A$ receptors. Thus; inhibition of PKCε augments $GABA_A$ receptor-mediated signaling, and based on the fact that $GABA_A$ agonists are anxiolytics, it can be concluded that PKCε inhibitors are potent suppressors of anxiety. This conclusion is supported by the observation that PKCε$^{-/-}$ mice have reduced basal levels of stress-associated hormones and accelerated reduction of hormone levels in the wake of an event that increases such levels.

In one specific aspect, the present invention is directed to animal cells that are PKCε deficient due to a disruption in the PKCε coding nucleic acid sequences. An additional aspect of the present invention is the use of a genetically modified PKCε deficient cell to generate PKCε-deficient non-human transgenic embryos and animals. Other aspects of the present invention are the PKCε-deficient non-human, preferably mouse, transgenic embryos and animals, and offspring that comprise a targeted disruption in the PKCε gene, and hence produce less than wild-type levels of PKCε activity. The PKCε deficient non-human transgenic animals of the present invention may be heterozygous or homozygous for the mutated PKCε allele.

The present invention is also directed to assays for identifying anxiolytic compounds. The assays of the invention comprise identification of a compound that inhibits the enzymatic activity of PKCε, and isolation of such compound. In another specific aspect, the present invention is directed to pharmaceutical compositions comprising a therapeutically effective amount of a compound inhibiting the enzymatic activity of PKCε and a pharmaceutically acceptable carrier. In addition, the present invention is directed to the treatment of anxiety by administration of such pharmaceutical compositions.

Other aspects of the present invention are methods of modulating consumption of a drug of abuse and/or the effects of such drug by administering a modulator of PKCε. Administration of an inhibitor of PKCε would thereby reduce consumption of alcohol, barbituates, nicotine, opiates, or psychostimnuants. Increased consumption of such drugs would result from embodiments of the method that involve the administration of enhancers of PKCε.

Another aspect of the present invention is based on the discovery that PKCε acts as a selective modulator of endogenous and nonendogenous allosteric agonists of $GABA_A$ receptors. Therefore, conditions that are amenable to treatment by such allosteric agonists of $GABA_A$ receptors can be treated by methods of the present invention that involve the administration of an inhibitor of the ε isozyme of protein kinase C (PKCε) alone or in combination with such allosteric agonists. Conditions suitable for such treatment include anxiety, addiction, withdrawal syndrome, skeletal muscle spasms, convulsive seizures, and epilepsy. A composition comprising an inhibitor of PKCε and an allosteric agonist of a $GABA_A$ receptor is yet another aspect of the present invention. An additional aspect of the present invention is a method for reducing the effective dose of an allosteric agonist of a $GABA_A$ receptor by administering an inhibitor of the ε isozyme of protein kinase C (PKCε) in combination with such allosteric agonist.

Further aspects of the present invention include diagnostic methods and kits for predicting the likelihood that a person will become addicted to a drug of abuse.

BRIEF DESCRIPTION OF THE DRAWINGS

FIG. 1 depicts the generation of PKCε$^{-/-}$ mice. FIG. 1A shows the introduction of a novel Apa I site (A*) by the targeting vector that allows detection of a 1.6 kb fragment on Southern blots of Apa I and Sca I digests of mutant genomic DNA. FIG. 1B depicts a Southern blot analysis of tail samples from mouse pups born to heterozygous progeny of male chimeras and C5BI/6J females. Lanes containing samples from 7 homozygous knockouts are labeled by sex. FIG. 1C depicts a Western blot with anti-PKCε antibody of brain samples from wild-type (+/+), heterozygous and knockout (−/−) littermates.

FIG. 2 depicts PKC isozyme immunoreactivity in wild-type, heterozygous and mutant PKCε mice. No compensatory increase in other PKC isozymes is observed in knockout mice.

FIGS. 3A and 3B depict MAP2 immunoreactivity in CAI stratum radiatum in wild-type (FIG. 3A) and PKCε$^{-/-}$ (FIG. 3B) littermates. Mice (6 months of age) were perfused with saline and then 4% paraformaldehyde. Coronal-sections of brain were stained for MAP-2 immunoreactivity. After labeling with an FITC-tagged secondary antibody, sections were examined by confocal scanning laser microscopy. Apical dendrites of CAI pyramidal neurons are shorter and appear to branch more in the PKCε$^{-/-}$ mice.

FIG. 4 depicts decreased acetyl cholinesterase activity in CAI hippocampus of PKCε$^{-/-}$ mice. PKCε$^{-/-}$ mice (age 6 months) and wild-type littermates were perfused with saline and then 4% paraformaldehyde. Coronal brain sections through the hippocampus were stained enzymatically for the presence of cholinesterase containing nerve fibers. Top panel: wild-type mice; bottom panel: PKCε$^{-/-}$ mice. Abbreviations: SO, stratum oriens; SP stratum pyramidale; SR, stratum radiatum; SL/M Stratum lacunosum and moleculare.

FIG. 5 depicts body weight, food intake, and water intake measured daily for two weeks. PKCε$^{-/-}$ mice did not differ from controls on any measure. *,** indicates different from male, $p<0.05$; 0.01.

FIG. 6 depicts an analysis of the mice in an open-field locomotor apparatus. PKCε$^{-/-}$ mice demonstrated normal locomotor behavior (left) and habituation to a novel environment (right). + indicates different from day 1, $p<0.05$.

FIG. 7 depicts the increased traveling distance in the center of an open field by PKCε$^{-/-}$ mice, indicating reduced anxiety.

* indicates different from wild-type p<0.05, p<0.01.+indicates different from day 1, p<0.05.

FIG. 8 depicts the increased time spent resting in the center of an open field by PKCε$^{-/-}$ mice, indicating reduced anxiety. *,** indicates different from wild-type p<0.05, p<0.01. +indicates different from day 1, p<0.05.

FIG. 9 depicts a performance analysis on elevated plus maze. PKCε$^{-/-}$ mice demonstrated twice the distance traveled (top, middle), a three-fold increase in time spent resting (top, right), as well as a two-fold increase in visit time and ambulatory time in the open arms as compared to wild-type controls. These results indicate reduced anxiety in PKCε$^{-/-}$ mice. * indicates significantly different from wild-type, p<0.05.

FIG. 10 depicts that PKCε$^{-/-}$ mice demonstrated a two-fold greater response to the duration of the loss of righting reflex (LORR) effect of ethanol. * indicates significantly different from wild-type, p<0.05.

FIG. 11 depicts that PKCε$^{-/-}$ mice demonstrated a two-fold greater response to the duration of the loss of righting reflex (LORR) effect of pentobarbital. * indicates significantly different from wild-type, p<0.05.

FIG. 12 depicts voluntary 24-hr ethanol intake (A), ethanol preference (ethanol mls/total mls consumed) (B), average daily body weight (C), food (D), and water intake (E) measured over a two-week period, and average intake of saccharin (Sacc, F) or Quinine (Quin, G) over two days at each concentration in PKCε$^{-/-}$ and PKCε$^{+/+}$ mice. * indicates significantly different from wild-type, p<0.05.

FIG. 13 depicts the difference between PKCε$^{-/-}$ and PKCε$^{+/+}$ mice with regard to spontaneous locomotor behavior and habituation to a novel environment (A), locomotor activation following ethanol injection (B), duration of the loss of righting reflex (LORR) produced by ethanol (C), and blood ethanol clearance after injection of ethanol (D). * indicates significantly different from zero ethanol, p<0.05; ** indicates significantly different from wild-type, p<0.05.

FIG. 14 depicts the difference between PKCε$^{-/-}$ and PKCε$^{+/+}$ mice with regard to duration of Loss of righting reflex (LORR) in response to GABA$_A$ allosteric agonists pentobarbital (A) or diazepam (B), or locomotor activity in response to diazepam (C), the direct GABA$_A$ agonist muscimol (D), or the NMDA antagonist MK-801 (E). * indicates significantly different from wild-type, p<0.05*; † indicates significantly different from vehicle control, p<0.05.

FIGS. 15A & B depicts $^{36}$Cl$^-$ uptake in cortical microsacs prepared from PKCε$^{-/-}$ and PKCε$^{+/+}$ mice incubated for five seconds with 0-20 μM muscimol (A) or 1 μM muscimol in the presence of 20 mM ethanol (EtOH) or 0.1 μM flunitrazepam (Flu) (B). FIG. 15C depicts $^{36}$Cl$^-$ uptake in cortical microsacs prepared from wild-type mice that were first left untreated (Con), permeabilized with saponin only (Sap), or permeabilized with saponin in the presence of the εV1-2 (εV) peptide or scrambled S-εV1-2 (SεV) peptide and subsequently incubated with 1 μM muscimol and 0.1 μM flunitrazepam for 5 seconds. Data in FIGS. 15B & C are expressed as the percent above uptake measured in microsacs incubated in muscimol alone and are mean±SE values from 20 (ethanol), 5 (flunitrazepam) and 3 (peptide) experiments. * indicates significantly different from wild-type microsacs treated with the same drugs or from microsacs to subjected all other conditions, p<0.05. FIG. 15D depicts Western blots of forebrain tissue from wild-type (+/+) and PKCε mutant (−/−) mice using polyclonal anti-PKC antibodies (0.5 μg/ml) to indicated PKC isozymes from Santa Cruz Biotechnology (Santa Cruz, Calif.).

FIG. 16 depicts average handling-induced convulsion (HIC) score in PKCε$^{+/+}$ and PKCε$^{-/-}$ mice after removal from ethanol-containing liquid diet. * indicates significantly different from zero ethanol, p<0.05; ** indicates significantly different from wild-type, p<0.05.

FIG. 17 depicts the percentage increase in $^{36}$Cl$^-$ uptake in cortical microsacs prepared from PKCε$^{-/-}$ (KO) and PKCε$^{+/+}$ (WT) mice incubated for five seconds with 1 μM muscimol and 0-10$^{-6}$M allopregnanolone relative to $^{36}$Cl$^-$ uptake in cortical microsacs prepared from PKCε$^{-/-}$ and PKCε$^{+/+}$ mice, respectively, incubated only with 1 μM muscimol.

FIG. 18 depicts levels of plasma corticosterone in PKCε$^{+/+}$ (WT) and PKCε$^{-/-}$ (KO) mice under basal conditions and zero and one hour after being restrained. * indicates significantly different from wild-type, p<0.05.

FIG. 19 depicts basal levels of plasma ACTH in PKCε$^{+/+}$ (WT) and PKCε$^{-/-}$ (KO) mice.

FIG. 20 depicts levels of amino acids aspartate (Asp), glutamate (Glu), and glycine (Gly), taurine (Taur) and gamma aminobutyric acid (GABA) in the nucleus accumbens of PKCε$^{+/+}$ and PKCε$^{-/-}$ mice as measured by microdialysis. * indicates significantly different from wild-type, p<0.05.

FIG. 21 depicts dopamine (DA) levels in the nucleus accumbens of PKCε$^{+/+}$ and PKCε$^{-/-}$ mice during three 120-min phases (Baseline, after saline injection, and after ethanol injection. * indicates significantly different from wild-type, p<0.05.

DETAILED DESCRIPTION OF THE INVENTION

A. General Overview

The present invention includes the following aspects: 1) the production of PKCε deficient cells and non-human animals; 2) the identification and the use of the PKC isozyme ε (PKCε) as a target for the modulation of anxiety in a mammal; 3)the use of modulators of PKCε to modulate alcohol consumption and self-administration of other drugs of abuse and the effects of alcohol consumption; 4) the use of inhibitors of PKCε, either alone or in conjunction with allosteric agonists of GABA$_A$ receptors, to treat conditions, such as anxiety, addiction, withdrawal syndrome, skeletal muscle spasms, convulsive seizures, and epilepsy, that are amenable to treatment by allosteric agonists of GABA$_A$ receptors; and 5) a diagnostic method for identifying individuals at risk for becoming alcoholics or abusers of other drugs. Each such aspect is discussed individually below.

B. Definitions

A "pharmaceutically acceptable formulation" comprises a formulation that is suitable for administering the PKCε modulator in a manner that gives the desired results and does not also produce adverse side effects sufficient to convince a physician that the potential harm to a patient is greater than the potential benefit to that patient. The basic ingredient for an injectable formulation is a water vehicle. The water used is of a purity meeting USP standards for sterile water for injection. Aqueous vehicles that are useful include sodium chloride (NaCl) solution, Ringer's solution, NaCl/dextrose solution, and the like. Water-miscible vehicles are also useful to effect full solubility of the PKCε modulator. Antimicrobial agents, buffers and antioxidants are useful, depending on the need.

An "effective amount" is an amount that results in the desired result. Such effective amount will vary from person to person depending on their condition, their height, weight, age, and health, the mode of administering the modulator of PKCε, the particular modulator administered, and other factors. As a result, it is advisable to empirically determine an effective amount for a particular patient under a particular set of circumstances.

A "modulator of PKCε" is either an inhibitor of PKCε or an enhancer of PKCε.

An "inhibitor of PKCε" comprises a molecule or group of molecules that interferes with: (1) the expression, modification, regulation, activation or degradation of PKCε, (2) one or more of the normal functions of PKCε, or (3) the expression, modification, regulation or activation of a molecule acting downstream of PKCε in a PKCε-dependent pathway. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location. An inhibitor of PKCε can also inhibit other isozymes of PKC. However, a selective inhibitor of PKCε significantly inhibits one or more normal functions of PKCε at a concentration at which the other isozymes of PKC are not significantly inhibited. An inhibitor "acts directly on PKCε" when the inhibitor binds to PKCε via electrostatic or chemical interactions. Such interactions may or may not be mediated by other molecules. An inhibitor acts "indirectly on PKCε" when its most immediate effect is on a molecule other than PKCε which influences the expression, activation or functioning of PKCε or the downstream effects of PKCε.

An "enhancer of PKCε" comprises a molecule or group of molecules that enhances: (1) the expression, modification, regulation, activation or degradation of PKCε, (2) one or more of the normal functions of PKCε, or (3) the expression, modification, regulation or activation of a molecule acting downstream of PKCε in a PKCε-dependent pathway. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location. An enhancer of PKCε can also enhance other isozymes of PKC. However, a selective enhancer of PKCε significantly enhances one or more normal functions of PKCε at a concentration at which the other isozymes of PKC are not significantly affected. An enhancer "acts directly on PKCε" when the enhancer binds to PKCε via electrostatic or chemical interactions. Such interactions may or may not be mediated by other molecules. An enhancer acts "indirectly on PKCε" when its most immediate effect is on a molecule other than PKCε which influences the expression, activation or functioning of PKCε or the downstream effects of PKCε.

A compound or molecule "modulates that activity of PKCε" if it affects (1) one or more of the normal functions of PKCε, or (2) the expression, modification, regulation, activation or degradation of PKCε or a molecule acting upstream of PKCε in a regulatory or enzymatic pathway. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location.

An "engineered mutation" in an allele of the PKCε gene comprises a change in nucleotide sequence of the PKCε gene that results in the production of (1) increased or reduced amounts of PKCε protein relative to the amounts produced in the absence of such change or (2) PKCε protein having enhanced or impaired normal functions relative to such functions in the absence of such changes. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location.

A "drug of abuse" comprises any substance the excessive consumption or administration of which can result in a diagnosis of substance dependence or substance abuse as defined herein or as defined by the current DSM Criteria promulgated by the American Psychiatric Association or equivalent criteria Drugs of abuse include, without limitation, ethanol, psychostimulants, opiates, and other sedative-hypnotic drugs. For clarity, it is understood that drugs of abuse include, without limitation, heroin, cocaine, metamphetamines and barbituates.

"Substance dependence"[1] comprises a maladaptive pattern of substance use, leading to clinically significant impairment or distress, as manifested by three (or more) of the following symptoms, occurring at any time in the same 12-month period:

[1] Definition derived from American Psychiatric Association, Diagnostic Criteria for DSM-IV, Washington D.C., APA, 1994.

(1) Tolerance, as defined by either of the following: (a) a need for markedly increased amounts of the substance to achieve intoxication or desired effect, or (b) markedly diminished effect with continued use of the same amount of the substance;

(2) Withdrawal, as manifested by either of the following: (a) the characteristic withdrawal syndrome for the substance (refer to Criteria A and B of the criteria sets for Withdrawal from the specific substances), or (b) the same (or closely related) substance is taken to relieve or avoid withdrawal symptoms;

(3) The substance is often taken in larger amounts or over a longer period than was intended;

(4) There is a persistent desire or unsuccessful efforts to cut down or control substance use;

(5) A great deal of time is spent in activities necessary to obtain the substance (e.g., visiting multiple doctors or driving long distances), use the substance (e.g., chain-smoking), or recover from its effects;

(6) Important social, occupational, or recreational activities are given up or reduced because of substance use; and (7) The substance use is continued despite knowledge of having a persistent or recurrent physical or psychological problem that is likely to have been caused or exacerbated by the substance (e.g., current cocaine use despite recognition of cocaine-induced depression, or continued drinking despite recognition that an ulcer was made worse by alcohol consumption).

"Substance abuse"[2] comprises a maladaptive pattern of substance use leading to clinically significant impairment or distress, as manifested by one (or more) of the following, occurring within a 12-month period: (1) recurrent substance use resulting in a failure to fulfill major role obligations at work, school, or home (e.g., repeated absences or poor work performance related to substance use; substance-related absences, suspensions, or expulsions from school; neglect of children or household); (2) recurrent substance use in situations in which it is physically hazardous (e.g., driving an automobile or operating a machine when impaired by substance use); (3) recurrent substance-related legal problems (e.g., arrests for substance-related disorderly conduct); and (4) continued substance use despite having persistent or recurrent social or interpersonal problems caused or exacerbated by the effects of the substance (e.g., arguments with spouse about consequences of intoxication, physical fights).

[2] Definition derived from American Psychiatric Association, Diagnostic Criteria for DSM-IV, Washington D.C., APA, 1994.

"Substance intoxication"[3] comprises the development of a reversible substance-specific syndrome due to recent ingestion of (or exposure to) a substance in which clinically significant maladaptive behavioral or psychological changes that are due to the effect of the substance on the central nervous system (e.g., belligerence, mood lability, cognitive impairment, impaired judgment, impaired social or occupational functioning) develop during or shortly after use of the substance and are not due to a general medical condition or not better accounted for by another mental disorder.

[3] Definition derived from American Psychiatric Association, Diagnostic Criteria for DSM-IV, Washington D.C., APA, 1994.

"Substance withdrawal"[4] comprises the development of a substance-specific syndrome, due to the cessation of (or reduction in) substance use that has been heavy and prolonged, that causes clinically significant distress or impairment in social, occupational, or other important areas of functioning and such symptoms are not due to a general medical condition or better accounted for by another mental disorder.

[4] Definition derived from American Psychiatric Association, Diagnostic Criteria for DSM-IV, Washington D.C., APA, 1994.

"Alcohol intoxication"[5] comprises clinically significant maladaptive behavioral or psychological changes (e.g., inappropriate sexual or aggressive behavior, mood lability, impaired judgment, impaired social or occupational functioning) that developed during, or shortly after, alcohol ingestion and accompanied by one (or more) of the following signs: (1) slurred speech, (2) incoordination, (3) unsteady gait, (4) nystaginus, (5) impairment in attention or memory, or (6) stupor or coma, wherein the symptoms are not due to a general medical condition or better accounted for by another mental disorder.

[5] Definition derived from American Psychiatric Association, Diagnostic Criteria for DSM-LV, Washington D.C., APA, 1994.

"Alcohol withdrawal"[6] comprises a condition characterized by two (or more) of the following symptoms which develop within several hours to a few days after cessation of (or reduction in) heavy and prolonged alcohol use, are not due to a general medical condition or better accounted for by another mental disorder, and cause clinically significant distress or impairment in social, occupational, or other important areas of functioning: (1) autonomic hyperactivity (e.g., sweating or pulse rate greater than 100), (2) increased hand tremor insomnia, (3) insomnia, (4) nausea or vomiting, (5) transient visual, tactile, or auditory hallucinations or illusions, (6) psychomotor agitation, (7) anxiety, and (8) grand mal seizures.

[6] Definition derived from American Psychiatric Association, Diagnostic Criteria for DSM-IV, Washington D.C., APA, 1994.

The "effects of a drug of abuse" comprises those biochemical or behavioral changes that occur as a result of and within a reasonable time following the administration of the drug of abuse. Different effects can be expected depending on the drug of abuse and the dose administered thereof. For example, the effects of low doses of ethanol include locomotor activation whereas the effects of high doses of ethanol include the symptoms of alcohol intoxication.

A "condition amenable to treatment by an allosteric agonist of a $GABA_A$ receptor" comprises any indication for which administration of an allosteric agonist of a $GABA_A$ receptor is approved by the Food and Drug Administration or recommended or acknowledged in the medical literature. REMINGTON: THE SCIENCE AND PRACTICE OF PHARMACY, $19^{th}$ edition (1995) is one source of information regarding such indications. Conditions amenable to treatment by an allosteric agonist of a $GABA_A$ receptor include, but are not limited to, anxiety, addiction, withdrawal syndrome, skeletal muscle spasms, convulsive seizures, and epilepsy.

A person is "dependent upon a drug of abuse" if such person is determined by a licensed physician or other appropriate accredited medical personnel to meet the criteria for substance dependence with respect to such drug of abuse.

A person is "an abuser of a drug of abuse" or "abusive of a drug of abuse" if such person is determined by a licensed physician or other appropriate accredited medical personnel to meet the criteria for substance abuse with respect to such drug of abuse.

The specific items mentioned in the foregoing definitions represent preferred embodiments of the present invention.

C. Generation and Characterization of $PKC\epsilon^{-/-}$ Animals

In one embodiment, the present invention relates to animal cells that are PKCε-deficient due to a disruption in the PKCε coding nucleic acid sequences. In another embodiment, the present invention relates to the use of a genetically modified PKCε deficient cell to generate PKCε-deficient non-human transgenic embryos and animals. In again another embodiment, the present invention relates to PKCε-deficient non-human, preferably mouse, transgenic embryos and animals, and offspring that comprise a targeted disruption in the PKCε gene, and hence produce less than wild-type levels of PKCε activity. The PKCε deficient non-human transgenic animals of the present invention may be heterozygous or homozygous for the mutated PKCε allele.

One aspect of the present invention is directed to the production of PKCε deficient cells, and PKCε deficient non-human animals. The non-human transgenic animals contemplated by the present invention generally include any vertebrates, and preferably mammals, which encode a PKCε, or a PKCε homolog. Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, and porcine species, other members of the rodent family, e.g., rat, as well as rabbit and guinea pig and non-human primates, such as chimpanzee, may be used to practice the present invention. Particularly preferred animals are rats, rabbits, guinea pigs, and most preferably mice.

Other aspects of the invention involve a diploid animal cell comprising an engineered mutation in at least one allele of the gene encoding PKCε and a non-human transgenic animal comprising one or more such cells. Preferred embodiments include those in which: the cell is homozygous for the engineered mutation; the cell is a mouse embryonic stem cell; the cell is an embryonic fibroblast cell that is homozygous for said mutation; the transgenic animal contains germline cells having such mutation; and such mutation results in the mutant cell having lower or higher PKCε activity levels than wild-type cells. Lower levels can be used to further characterize the function of the PKCε protein and identify other molecules, both endogenous and nonendogenous, with which it interacts, including molecules in the same pathway as PKCε. Cells or animals with enhanced levels of PKCε activity may be used to identify and/or test molecules for ability to inhibit or diminish such PKCε activity. Engineered mutations that are deletion mutations are preferred, especially when such mutation deletes nucleotides at least about 1,200 bases of the PKCε coding sequence. Embryos, juvenile and adult animals that comprise cells having an engineered mutation in at least one allele of the gene encoding PKCε and that have as an ancestor (a direct relation from an earlier generation) a non-human transgenic animal comprising one or more cells having such engineered mutation are also preferred; such embryos and animals are sometimes referred to herein as "descendants of" or "derived from" the non-human transgenic animal. It is particularly preferable for all or almost all of the cells of a descendent to be homozygous for the mutant PKCε gene. Even more preferably, the mutation for which such cells are homozygous is a deletion mutation.

Preferred embodiments of the present invention include diploid mouse cells, mouse embryos, and mice that contain two chromosomal alleles of the PKCε gene, wherein at least one of the PKCε alleles contains a mutation such said cell produces less than wild-type levels of PKCε activity. Based on the suggested role of PKCε in the nervous system, and ethanol addiction. PKCε deficient animals and cells are deemed to be useful as, inter alia, experimental models for e.g., studying behavior, neurological responses and ethanol addiction, carcinogenesis, heart function, ischemia, and cell growth.

A variety of methods, vector systems and other tools are known in the art that may be used for the generation of PKCε$^{+-}$ and PKCε$^{-/-}$ cells and animals. See, for example, Joyner A J, ed. *Gene Targeting*. The Practical Approach Series, ed. Rickwood D. and Flames B. D., 1993, IRI Press: New York.

Generally, the mutation, or targeted disruption, in the target gene, i.e., PKCε, may be engineered using any of a number of well established mutations that are well known in the art. Preferably, the mutation is a deletion mutation, although substitution mutations and/or insertion mutations are included within the scope of the present invention.

Substitution mutations can be prepared by site directed mutagenesis that introduces a stop codon or other mutation near the 5' end of the target gene such that abortive production of PKCε protein results, or the production of a mutant protein which lacks PKCε activity.

Similarly, insertion mutations can be introduced within the PKCε gene taking advantage of the convenient restriction sites therein, such as any of the exonic restrictions sites or other sites which are easily identified by exonic sequencing of the PKCε gene and restriction mapping.

Another method of introducing an insertion or other mutation consists of infecting with a retrovirus which integrates in the PKCε locus, thereby creating a mutated PKCε allele using methodologies similar to that described by von Melcher et al., 1992, *Genes and Development* 6:919-927.

An alternative method of isolating PKCε-deficient cells is by the screening of ES cell libraries that have been treated to incorporate integrated viral (usually retrovirus or adeno-associated virus) sequences that inactivate the gene in which they have inserted. Once isolated, the PKCε-deficient ES cell may be used to generate transgenic animals.

Preferably, the mutants of the present invention lack part of the DNA sequence coding for PKCε so that a defective PKCε allele is more likely to result The coding region of PKCε is 2721 bp, corresponding to 709 amino acids. Ono et al., 1988, *J. Biol. Chem.* 263:6927-6932. Deletion mutants can be produced by eliminating a DNA fragment from a coding region of the PKCε gene so that proper folding or substrate binding of the PKCε protein is prevented. The size of the deletion may vary, but in general a larger deletion is preferable to a smaller deletion since the larger deletions are more likely to result in a deficiency in PKCε activity.

Alternatively, by deleting a single base pair or two base pairs (or any number of base pairs not divisible by 3) from the coding region, one may generate frameshift mutations that alter the PKCε protein. In the latter instance, a truncated polypeptide may be produced because polypeptide synthesis is aborted due to a frame shift-induced stop codon. Still, changing a single base pair in the coding region of the PKCε gene could also be a mutation which, if resulting in an amino acid change, could alter the proper folding of the PKCε protein and thereby create an PKCε-deficiency. A single amino acid change so generated could also alter the affinity of PKCε for its substrate and thereby result in a deficiency of PKCε activity Another alternative is to generate a deletion or other mutation in the non-coding region of the PKCε gene which effects the proper splicing of the PKCε messenger RNA. Such a mutation would effectively create a mutant PKCε transcript which is missing an entire exon or several exons normally present in the wild-type PKCε mRNA.

Another alternative is to delete a non-coding regulatory region to decrease expression of the PKCε gene. The preferred size of the deletion is about several hundred nucleotides near the 5' end of the gene. Preferably, such a deletion would eliminate a number of nucleotides from the coding region not evenly divisible by 3, thereby creating a frameshift mutation as well. Alternatively, promoter sequences may be deleted or altered that would diminish the transcription of the PKCε gene.

Antisense RNA transgenes may also be employed to partially or totally knock-out expression of specific genes. See, Helene and Toulme, 1990, *Biochimica Biophys. Acta* 1049: 99; Pepin et al., 1991 *Nature* 355:725, Stout and Caskey, 1990, *Somat. Cell Mol. Genet.* 16:369; Munir et al., 1990, *Somat. Cell. Mol. Genet.* 16:383.

Generally, antisense polynucleotides for the purposes of the invention are complementary to parts of the sequence of the PKCε gene. Complementary antisense polynucleotides include antisense RNA which can hybridize specifically to individual mRNA species and hinder or prevent transcription and/or RNA processing of the mRNA species and/or translation of the encoded polypeptide (Ching et al., 1989, *Proc. Natl. Acad. Sci. USA* 86:10006-10010; Broder et al., *Ann. Int. Med.* 113:604-618; Loreau et al., 1990, *FEBS Letters* 274: 53-56; Holcenberg et al. WO91/11535; WO91/09865; WO91/04753; WO90/13641; and EP 386563). An antisense sequence is a polynucleotide sequence of at least about 15 contiguous nucleotides in length, typically at least 20 to 30 nucleotides in length, and preferably more than about 30 nucleotides in length that is substantially complementary to a target gene sequence, or sequences, in a cell. In some embodiments, antisense sequences may have substitutions, additions, or deletions as compared to the complementary target sequence but as long as specific hybridization is retained, the polynucleotide will generally function as an antisense inhibitor of gene expression.

Preferably, the antisense sequence is complementary to an endogenous PKCε target gene sequence. In some cases, sense sequences corresponding to the PKCε target region sequence may function to suppress expression, particularly by interfering with transcription. Alternatively, an antisense polynucleotide will generally suppress PKCε expression at a post-transcriptional level.

Given that antisense polynucleotides inhibit the production of the polypeptide(s) in cells, they may further alter a non-human transgenic animal's capacity to produce PKCε protein.

Antisense polynucleotides may be produced from a heterologous expression cassette inserted into transgenic pluripotent embryonic stem cells which may subsequently be used to generate the presently described PKCϵ-deficient animals. Where the expression of the antisense polynucleotide is placed under the control of promoter elements that are primarily, or exclusively, active under specific conditions or at specific phases of embryonic development, it is possible to selectively suppress expression of the target gene. The target region sequence may function to suppress expression, particularly by interfering with transcription. Alternatively, an antisense polynucleotide will generally suppress PKCϵ expression at a post transcriptional level.

Given that antisense polynucleotides inhibit the production oil the polypeptide(s) in cells, they may further alter a nonhuman transgenic animal's capacity to produce PKCϵ protein.

Antisense polynucleotides may be produced from a heterologous expression cassette inserted into transgenic pluripotent embryonic stem cells which may subsequently be used to generate the presently described PKCϵ-deficient animals. Where the expression of the antisense polynucleotide is placed under the control of promoter elements that are primarily, or exclusively, active under specific conditions or at specific phases of embryonic development, it is possible to selectively suppress expression of the target gene.

The gene modified animal cells of the present invention can be prepared by any of several techniques that are well established in the art. In particular, techniques conceptually similar to those taught in U.S. Pat. No. 5,464,764 issued to Capecchi and Thomas on Nov. 7, 1995, herein incorporated by reference, may be used. In general, PKCϵ-defective cells may be engineered using the following steps:

(1) Constructing a targeting vector comprising a cloning vector and a DNA fragment containing at least one positively selectable marker gene (positive selection marker), flanked by two regions of the mouse PKCϵ gene or genomic locus which are in the same 5' to 3' orientation to one another referred to as the regions of homology;

(2) Including in the targeting vector a negatively selectable marker gene (negative selection marker) adjacent to one of the regions of homology. This negatively selectable marker may increase the likelihood of recovering the desired homologous recombination event deleting a portion of the PKCϵ gene but it is not required;

(3) Transfecting PKCϵ$^{+/+}$ mouse cells with the targeting vector of step (2);

(4) Screening or selecting for said marker(s) in the resulting transfected mouse cells of step (3); and (5) Screening for PKCϵ-deficient mouse cells from those cells in step (4) which are found to contain or express said positive selection marker(s) and not express said negative selection marker(s).

The precise PKCϵ gene or gene locus sequences which must be present in the targeting vector of step (1) will depend on the sequences chosen for the deletion, and (2) the restriction nucleases to be employed in the engineering of the deletion mutant.

The particular positive and negative selection markers employed in the present invention are not critical to the practice of the invention. Examples of preferred positive and negative selection markers are listed in Table I of U.S. Pat. No. 5,464,764. The positive selectable marker should be located between the regions of homology and the negative marker, if one is used, should be outside the regions of homology. The regions of homology should generally be present in the vector in the same 5' to 3' orientation relative to one another. Conversely, the relative orientations of the positive and negative selectable markers are not critical. In fact, it is not really necessary to include a negative selectable marker, even though the presence of the negative marker may improve selection for targeted clones.

Preferably, the positive selectable marker is expressed in the cells that are targeted for gene modification. Positive and/or negative selection markers are deemed to be functional in the transfected cells if the DNA sequences encoding the selectable markers are capable of conferring either a positive or negative phenotypic selection characteristic to cells expressing the sequences. In general, the marker will be operably linked to a regulatory sequence that mediates the expression of the marker. A nucleic acid marker is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous.

Additionally, the means by which the positive selectable marker gene is made functional is not critical to the present invention. Positive selection is accomplished by exposing the cells to an appropriate agent which kills or otherwise selects against cells that do not contain or express an integrated positive selection marker. The positive selectable marker gene may have a promoter driving its expression or it may be driven by the juxtaposition of transcriptional elements at the target locus with the positive selectable marker. The latter gene organization requires that the transcriptional elements are active in the transfected cells.

The DNA used in the regions of homology should be derived from genomic DNA from the PKCϵ gene locus, or sequences that flank the PKCϵ gene locus. Where the mouse gene is targeted, the strain of mouse from which the DNA is derived is not important but it should preferably be the same as the strain of mouse as the cells targeted for gene transfer. Using DNA in the homology regions that is isogenic to the cells in which gene targeting will be performed may enhance the efficiency with which gene targeting is accomplished. The regions of homology may be derived from genomic libraries of mouse DNA which may be cloned into a variety of library vectors such as lambda phage vectors, cosmid vectors, plasmid vectors, p1 phage vectors, yeast artificial chromosome vectors, or other vectors. Regions of homology to be used in the targeting vector may also be derived directly from genomic DNA using the polymerase chain reaction (PCR). This method relies on having some knowledge of the sequence of the PKCϵ gene which is published, or the flanking sequences. Regions of homology so derived could be subcloned directly into the targeting vector.

The particular cloning vector used to construct the described targeting vector shall generally contain, inter alia, two regions of PKCϵ homology separated by a positive selectable marker gene. Optionally, a negative selectable marker may also included in the either, or both regions flanking the regions of homology. In any event, the particular cloning vector used is not critical as long as it contains a gene coding for a selective trait, e.g., drug resistance. Examples of suitable cloning vectors include, but are not limited to, pBR322 and pBR322-based vectors (Sekiguchi, 1983), pMB9, pBR325, pKH47 (Bethesda Research Laboratories), pBR328, pHC79, phage Charon 28 (Bethesda Research Laboratories, Boehringer Mannheim Biochemicals), pKB11, pKSV-10 (P-L Biochemicals), pMAR420 (Otsuka, 1981) and oligonucleotide (dg)-tailed pBR322 (Bethesda Research Laboratories), pBluescript or similar plasmids (Stratagene), puc19 or similar plasmids (New England Biolabs).

Alternatively, a targeting vector comprising two regions of PKCε homology separated by a positive selectable marker gene and an optional flanking negative selectable marker could be cloned into other cloning vectors such as lambda phage vectors, cosmid vectors, plasmid vectors, p1 phage vectors, yeast artificial chromosome vectors, or other vectors. Another option is to prepare the components of the targeting vector synthetically by PCR and simply ligating each component into its proper position by choosing restriction endonuclease sites for ligation which insured proper orientation of the homology regions relative to each other, and to insure that the positive selectable marker was located between the regions of homology. Once constructed, this "targeting cassette" may be placed into suitable vectors such as those described above, or placed into any of a wide variety of viral vectors (adenovirus, papilloma virus, retrovirus, adeno-associated virus, etc.).

The specific host employed for growing the targeting vectors of the present invention is not critical. Examples of such hosts include *E. coil* K12 RRI (Bolivar et al., 1977); *E. coil* K12 HBIOI (ATCC No. 33694); *E. coli* MM21 (ATCC No. 336780); and *E. coli* DHI (ATCC No. 33849). The preferred host in the present invention is DH5α (Life Technologies). Similarly, alternative vector/cloning systems may be employed such as targeting vectors which grow in *E. coli* or *Saccharomyces cerevisiae*, or both, or plasmid vectors which grow in *B. subtilus* (Ure et al., 1983, *Methods in Enzymology* "Recombinant DNA", vol. 101, Part C, Academic Press, NY).

The specific mouse cell that is mutated in the present invention is not critical, but is preferably a precursor pluripotent cell. The term precursor means that the pluripotent cell is a precursor of the desired transfected pluripotent cell which is prepared in accordance with the present invention. The pluripotent cell may be cultured in vivo to form a mutant mouse (Evans et al. 1981, *Nature* 292: 292-156). Examples of mouse cells that may be employed in the present invention include embryonic stem (ES) cells (preferably primary isolates of ES cells), such as AB 1 or A132. 1. Primary isolates of ES cells may be obtained directly from embryos, such as described for the EK.CCE cell line or for ES cells in general.

The particular embryonic stem cell employed in the present invention is not critical. Examples of such embryonic stem cells are AB 2.1, an hprt⁻ cell line, AB 1, an hprt⁺ cell line.

The ES cells are preferably cultured on stromal cells; e.g., STO cells and/or primary embryonic fibroblast cells as described by Robertson, 1987, in "Teratocarcinomas and embryonic stem cells: a practical approach", E. J. Robertson, ed. (Oxford: IRL Press), pp. 71-112. The stromal (and/or fibroblast) cells serve to reduce the clonal outgrowth of abnormal ES cells. In some cases it may be preferable to culture the ES cells in the presence of leukocyte inhibitory factor, though it is not critical (Gough et al., 1989, *Reprod. Fertil. Dev.* 1:281; Yamagouchi et al., 1989, *Science*, 246:1412).

In order to obtain the PKCε-deficient mice of the present invention, the mutant embryonic stems cells are injected into mouse blastocysts as described by Bradley, 1987, In "Teratocarcinomas and embryonic stem cells: a practical approach", E. Robertson, ed. (Oxford: IRL Press), pp. 113-151.

The particular mouse blastocysts employed in the present invention are not critical. Examples of suitable blastocysts include, but are not limited to, those derived from C57BI-6 mice, C57BL6Albino, Swiss outbred, CFLP, MFI or others.

In a specific embodiment of the present invention, a strategy was designed to create a targeting vector that would "knock out" 1.2 kb of the genomic DNA sequence for mouse PKCε, including all of exon I and part of the downstream intron sequence. To create a targeting vector, an 813 bp fragment (nt 470-1282) was amplified from mouse PKCε cDNA (Schaap et al., 1989, *FEBS Lett.* 243:351-357) by PCR. This fragment was used to screen a lambda FIX 11 129 mouse liver genomic library (Stratagene #946308). Two 13 kb and 15 kb overlapping genomic clones were selected and subcloned into the Nod site of pBluescript 11 SK+ (Stratagene). The clones were digested with BamHI and EcoRI restriction enzymes and fragments subclones into pBluescript 11 SK+. The subclones were analyzed by restriction digestion with 20 enzymes to construct a genomic map. Several clones were used to identify 1700 bp of sequence 5' of the ATG start codon. The preferred approach for the generation of the PKCε$^{-/-}$ animals, and characterization of such animals, is described in the Examples, see, infra, Section VI. B.

D. Assays for the Identification of Compounds Inhibiting PKCε Activity

The PKCε$^{-/-}$ mice of the present invention had a normal body weight, eating, drinking over a two-week period as compared to litter-mate wild-type controls at about 60 days of age. Similarly, PKCε$^{-/-}$ mice showed normal spontaneous locomotor behavior and habituation to a novel environment as compared to wild-type controls during three daily 1-hour tests. Although PKCε$^{-/-}$ mice exhibited normal gross locomotor behavior, further analysis showed that they differed significantly from wild-type controls on specific measures of open-field activity, exploration of a novel object, and elevated plus maze performance. For instance, PKCε$^{-/-}$ mice demonstrated a two-fold increase in distance traveled, and a three-fold increase in time spent resting in the center area of the open-field. Both of these findings are consistent with reduced anxiety levels in the mutant mice. The PKCε$^{-/-}$ mice also demonstrated a two-fold increase in exploratory behavior when a novel object was placed in the center of an open-field, which also suggests reduced anxiety levels. Moreover, when tested in the elevated plus maze, a well defined test of anxiety, PKCε$^{-/-}$ mice exhibited twice the distance traveled, visit time, ambulatory time, and rest time in the open arms as compared to controls. Finally, PKCε$^{-/-}$ mice have lower basal levels of stress hormones corticosterone and adrenocorticotropic hormone (ACTH) than wild-type mice and, although a stressful event causes increases in corticosterone levels in both mutant and wild-type mice, corticosterone returns to basal levels more quickly in mutant mice than in wild-type mice. These data clearly demonstrate that PKCε plays an important role in regulating anxiety and indicate that inhibitors of PKCε lessen anxiety without rendering the recipient drowsy or otherwise unable to respond appropriately to environmental stimuli.

GABA$_A$ receptors are widely known to mediate the sedative effects of ethanol (Allan and Harris, 1987, *Pharmacol. Biochem. Behav.* 27:665-670; Mehta and Ticku, 1988, *J. Pharmacol. Exp. Ther.* 246:558-564). However, the relationship between GABA$_A$ receptor sensitivity to effects of ethanol and the protein kinase C epsilon (PKCε) isozyme is less defined. The PKCε$^{-/-}$ animals of the invention are a model suited to determine whether the PKCε isozyme is involved in mediating the sedative effects of ethanol as measured by the onset and duration of an ethanol-induced loss of righting reflex (LORR). For that purpose, PKCε$^{-/-}$ mice and wild-type controls were given intraperitoneal injections of three doses of ethanol (3.2, 3.6, and 4.0 g/kg), after which latency and duration of LORR were measured. All mice showed a dose-dependent increase in LORR duration. PKCε$^{-/-}$ mice were found to have significantly higher LORR duration than wild-type controls. In order to determine if this effect was mediated by changes in $GABA_A$ receptor activity, the effects of sedative doses of the $GABA_A$ agonist pentobarbital were tested. $PKC\epsilon^{-/-}$ mice demonstrated two-fold greater sensitivity to the sedative effects of pentobarbital. This suggests that PKCε mediates the sedative effects of ethanol through GABA-ergic mechanisms.

The invention is based, in part, on the inventors' discovery that $PKC\epsilon^{-/-}$ mice show less fear and anxiety when compared to wild-type mice. Specifically, it was found that $PKC\epsilon^{-/-}$ mice have increased locomotor activity and spend more time in the center of an open field compared to wild-type littermates. They also explore novel objects more extensively than wild-type mice. On an elevated plus maze, male mice spend twice as long on the open arms of the maze. These results suggest that $PKC\epsilon^{-/-}$ mice, particularly the males, have less fear and anxiety than wild-type mice.

In another embodiment, the present invention relates to assays for identifying anxiolytic compounds. The assays of the invention comprise identification of a compound that inhibits the enzymatic activity of PKCε, and isolation of such compound. Such a compound may be identified comparing PKCε activity in the presence and absence of such compound and by administering such compound to a subject to and determining whether the subject becomes less anxious. In an additional aspect, the present invention relates to pharmaceutical compositions comprising a therapeutically effective amount of a compound inhibiting the enzymatic activity of PKCε and a pharmaceutically acceptable carrier. In again a further aspect, the present invention relates to the treatment of anxiety by administration of pharmaceutical compositions that contain a compound inhibiting the enzymatic activity of PKCε and a pharmaceutically acceptable carrier. Such a pharmaceutical composition may further comprise a therapeutically effective amount of a $GABA_A$ agonist, preferably an allosteric agonist of a $GABA_A$ receptor and more preferably a benzodiazepine.

The invention is further based, in part, on the inventors' discovery that $PKC\epsilon^{-/-}$ mice are hypersensitive to the sedative-hypnotic effects of compounds acting at $GABA_A$ receptors. Specifically, studies of alcohol-related behaviors show that the mutant mice sleep twice as long as wild-type mice when injected intraperitoneally with sedative doses of drugs acting at the $GABA_A$ receptors, such as ethanol, pentobarbital or diazepam. Together with open field and elevated plus maze data, the findings suggest that inhibition of PKCε augments $GABA_A$ receptor-mediated signaling. Since $GABA_A$ agonists are anxiolytics, PKCε inhibitors can be expected to have a suppressive effect on anxiety, enhancing the effects of anxiolytic drugs acting at the $GABA_A$ receptor or its signaling pathway.

PKCε Inhibitors as Suppressors of Anxiety and as Enhancers of The Anxiolytic Effects of $GABA_A$ Receptor Inhibitors. As elucidated by the present invention, PKCε is involved in the regulation of anxiety of an animal, including human and non-human mammals. As such, modulators of PKCε activity will be useful as agents to down- or upregulate anxiety in a subject in need, including non-human and human mammals. Agonists, enhancing the activity of PKCε will be useful agents to upregulate the enzymes effects, while antagonists, inhibiting the activity of PKCε will be useful agents to suppress anxiety in a subject. The invention encompasses assays for the identification of both compounds acting as PKCε agonists and antagonists, respectively, and the compounds identified by such assays.

In specific embodiments, the invention is for the identification of compounds inhibiting PKCε, and the compounds identified. Therapeutically effective amounts of such identified PKCε inhibitors are used for the preparation of pharmaceutical compositions for the treatment of anxiety, e.g., in conditions such as anxiety disorders, including panic disorder (e.g., panic disorder without agoraphobia, panic disorders with agoraphobia), agoraphobia without history of panic disorder, specific phobia, social phobia, obsessive-compulsive disorder, post-traumatic stress disorder, acute stress disorder, generalized anxiety disorder, substance-induced anxiety disorder, or anxiety disorder otherwise not specified. Such pharmaceutical compositions may be admninistered to a subject in need for the amelioration of symptoms of anxiety.

In one embodiment, the pharmaceutical compositions comprise a therapeutically effective amount of a compound inhibiting PKCε and a pharmaceutically acceptable carrier. These pharmaceutical composition may be administered to a subject in need for the treatment of anxiety. Such pharmaceutical compositions have important advantages over the treatment of anxiety using $GABA_A$ agonists. Specifically, in contrast to $GABA_A$ agonists, which are currently used for the treatment of anxiety, PKCε inhibitors should not have sedative effects on the subject treated, as evidenced by the phenotype of the $PKC\epsilon^{-/-}$ mice of the present invention, which were very awake and active and responded appropriately to a stressful event. As such, the pharmaceutical compositions of the present invention allow for the treatment of anxiety without having sedative side-effects.

In another embodiment, the invention is for pharmaceutical compositions comprising a therapeutically effective amount of a PKCε inhibitor and a $GABA_A$ agonist and a pharmaceutically acceptable carrier. Pharmaceutical compositions comprising both a PKCε antagonist and a $GABA_A$ agonist are particularly useful for the treatment of symptoms of severe anxiety, where enhancement of the anxiety-reducing effects of $GABA_A$ agonists is desired.

In one aspect, the present invention relates to assays for the identification of compounds that modulate and/or interfere with, preferably inhibit, PKCε activity. Such compounds are useful for the generation of pharmaceutical composition for the treatment of anxiety, e.g., in conditions such as anxiety disorders, including panic disorder (e.g., panic disorder without agoraphobia, panic disorders with agoraphobia), agoraphobia without history of panic disorder, specific phobia, social phobia, obsessive-compulsive disorder, post-traumatic stress disorder, acute stress disorder, generalized anxiety disorder, substance-induced anxiety disorder, or anxiety disorder otherwise not specified. Two general types of assays are preferred. On one hand, the assay may be designed to identify compounds that modify the enzymatic activity of PKCε. On the other hand, the assay may be designed to identify compounds that block specific interactions of PKCε with a cellular binding partner such that PKCε-specific signal transduction is modulated, e.g., interrupted.

For the identification and isolation of compounds modifying, inhibiting or enhancing the function of PKCε according to the invention, suitable cellular systems expressing PKCε may be employed. Alternatively, PKCε may be isolated and used for in vitro or in vivo assays for the identification and isolation of compounds specifically interfering with its activity. Generally, methods for PKCε purification and assessment of its activity are described in Ohmichi et al., 1993, *Biochem. J.* 295:767-772; Hundle et al., 1995, *J. Biol. Chem.* 270: 30134-30140; Hundle et al., 1997, *J. Biol. Chem.* 272:15028-15035; Uchida and Filburn, 1984, *J. Biol. Chem.* 259:12311-12314; Chakravarthy et al., 1994, *Biochem. J.* 304:809-816; Walton et al., 1987, *Analytical Biochemistry* 161:425-437; Roth et al., 1989, *J. Neurochem.* 52:215-22 1; Lehel et al., 1997, *Analytical Biochemistry* 244:340-346; and Papadopoulos and Hall, 1989, *J. Cell Biol.* 108:553-567.

More specifically, cells in an appropriate assay system expressing PKCε may be exposed to chemical compounds or compound libraries to identify compounds having the desired modulating effects. Alternatively, PKCε may be expressed in suitable expression systems, designed to allow for high-throughput testing of compounds from any source, optionally isolated, to identify molecules binding to or having measurable inhibitory effects on PKCε.

Nucleotide sequences encoding PKCε may be used to produce the corresponding purified protein using well-known methods of recombinant DNA technology. Among the many publications that teach methods for the expression of genes after they have been isolated is *Gene Expression Technology, Methods and Enzymology. Vol.*: 185. edited by Goeddel, Academic Press, San Diego, Calif. (1990).

The PKCε may be expressed in a variety of host cells, either prokaryotic or eukaryotic. In many cases, the host cells would be eukaryotic, more preferably host cells would be mammalian. Host cells may be from species either the same or different than the species from which the nucleic acid sequences encoding the protein identified with the methods of the invention are naturally present, i.e., endogenous. Advantages of producing PKCε by recombinant DNA technology in cellular expression systems include the development of optimized assay systems for the identification of modulating compounds. Generally, the expression systems of the invention have the advantage that they readily provide a system for the production of large amounts of recombinant proteins. However, under certain circumstances which the skilled artisan will appreciate, alternative expression systems may, in some instances, also prove advantageous for obtaining highly enriched sources of PKCε for purification and the availability of simplified purification procedures. Methods for recombinant production of proteins are generally very well established in the art, and can be found, among other places in Sambrook et al., *Molecular Cloning: A Laboratory Manual. 2nd Ed.*, Cold Spring Harbor (1989).

In an embodiment of the invention, cells transformed with expression vectors encoding PKCε are cultured under conditions favoring expression of its gene sequence and the recovery of the recombinantly produced protein from the cell culture. The PKCε protein produced by a recombinant cell may be secreted or may be contained intracellularly, depending on the nature of the gene and the particular genetic construction used. In general, it is more convenient to prepare recombinant proteins in secreted form. Purification steps will depend on the nature of the production and the particular protein produced. Purification methodologies are well established in the art; the skilled artisan will know how to optimize the purification conditions. General protocols of how to optimize the purification conditions for a particular protein can be found, among other places, in Scopes in: *Protein Purification: Principles and Practice*, 1982, Springer-Verlag New York, Heidelberg, Berlin.

In addition to recombinant production, peptide fragments of PKCε may be produced by direct peptide synthesis using solid-phase techniques. See, Stewart et al., *Solid-Phase Peptide Synthesis* (1969), W. H. Freeman Co., San Francisco; and Merrifield, 1963, *J. Am. Chem. Soc.* 85:2149-2154.

In vitro polypeptide synthesis may be performed using manual techniques or by automation. Automated synthesis may be achieved, for example, using Applied Biosystems 431A Peptide Synthesizer (Foster City, Calif.) following the instructions provided in the instruction manual supplied by the manufacturer.

In an embodiment of the invention, the PKCε protein and/or cell lines expressing the PKCε protein are used to screen for antibodies, peptides, organic molecules or other ligands that act as agonist or antagonists of the PKCε gene activity. For example, antibodies capable of interfering with the activity, e.g., enzymatic activity of PKCε, or with its interaction with a binding partner, e.g., ligand, adapter molecule, or substrate are used to inhibit PKCε's function. In cases where amplification of PKCε's function is desired, antibodies which mimic, e.g. a ligand, an adapter molecule or substrate of the corresponding the signal transduction pathway may be developed. Obviously, if desired, antibodies may be generated which modify the activity, function, or specificity of PKCε.

Alternatively, screening of peptide libraries or organic compounds with recombinantly expressed PKCε or cell lines expressing PKCε may be useful for identification of therapeutic molecules that function by inhibiting, enhancing, or modifying its biological activity.

Synthetic compounds, natural products, and other sources of potentially biologically active materials can be screened in a number of ways. The ability of a test compound to inhibit, enhance or modulate the function of the target protein may be determined with suitable assays measuring PKCε's function. For example, responses such as its activity, e.g., enzymatic activity, or the PKCε's ability to bind its ligand, adapter molecule or substrate may be determined in in vitro assays. Cellular assays can be developed to monitor a modulation of second messenger production, changes in cellular metabolism, or effects on enzymatic activity. These assays may be performed using conventional techniques developed for these purposes. Finally, the ability of a test compound to inhibit, enhance or modulate the function of PKCε will be measured in suitable animal models in vivo. For example, mouse models will be used to monitor the ability of a compound to inhibit or reduce anxiety, e.g., in conditions such as anxiety disorders, including panic disorder (e.g., panic disorder without agoraphobia, panic disorders with agoraphobia), agoraphobia without history of panic disorder, specific phobia, social phobia, obsessive-compulsive disorder, post-traumatic stress disorder, acute stress disorder, generalized anxiety disorder, substance-induced anxiety disorder, or anxiety disorder otherwise not specified.

In an embodiment of the invention, random peptide libraries consisting of all possible combinations of amino acids attached to a solid phase support are used to identify peptides that are able to interfere with the function PKCε. For example, peptides may be identified binding to a ligand-, adapter molecule- or substrate binding site of PKCε or functional domains thereof, such as the enzymatic domain. Accordingly, the screening of peptide libraries may result in compounds having therapeutic value as they interfere with its activity.

Identification of molecules that are able to bind to PKCε may be accomplished by screening a peptide library with recombinant soluble PKCε protein. Methods for expression and purification of the PKCε protein and may be used to express recombinant full PKCε protein or fragments thereof, depending on the functional domains of interest.

In order to identify and isolate the peptide/solid phase support that interacts and forms a complex with PKCε, it is necessary to label or "tag" the PKCε protein molecule or fragment thereof For example, PKCε may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to PKCε may be performed using techniques that are routine in the art.

In addition to using soluble PKCε molecules or fragments thereof, in another embodiment, peptides that bind to the PKCε may be identified using intact cells. The use of intact cells is preferred in instances where a PKCε function requires the lipid domain of the cell membrane to be functional. Methods for generating cell lines expressing PKCε identified with the methods and expression systems of the invention. The cells used in this technique may be either live or fixed cells. The cells are incubated with the random peptide library and will bind to certain peptides in the library. The so formed complex between PKCε and the relevant solid phase support/peptide may be isolated by standard methods known in the art, including differential centrifugation.

In the case where a PKCε function is measured that requires the lipid domain of the cell membrane, an alternative to whole cell assays is to reconstitute the receptor molecules into liposomes where a label or "tag" can be attached.

In another embodiment, cell lines that express PKCε or, alternatively, isolated PKCε, or fragments thereof, are used to screen for molecules that inhibit, enhance, or modulate PKCε's activity or signal transduction. Such molecules may include small organic or inorganic compounds, or other molecules that effect PKCε activity or that promote or prevent the complex formation with its ligand, adapter molecules, or substrates. Synthetic compounds, natural products, and other sources of potentially biologically active materials can be screened in a number of ways, which are generally known by the skilled artisan.

For example, the ability of a test molecule to interfere with PKCε function may be measured using standard biochemical techniques. Alternatively, cellular responses such as activation or suppression of a catalytic activity, phosphorylation, dephosphorylation, or other modification of other proteins, activation or modulation of second messenger production, changes in cellular ion levels, association, dissociation or translocation of signaling molecules, or transcription or translation of specific genes may also be monitored. These assays may be performed using conventional techniques developed for these purposes in the course of screening.

Further, effects on PKCε function may, via signal transduction pathways, affect a variety of cellular processes. Cellular processes under the control of the its signaling pathway may include, but are not limited to, normal cellular functions, proliferation, differentiation, maintenance of cell shape, and adhesion, in addition to abnormal or potentially deleterious processes such as unregulated cell proliferation, loss of contact inhibition and, blocking of differentiation or cell death. The qualitative or quantitative observation and measurement of any of the described cellular processes by techniques known in the art may be advantageously used as a means of scoring for signal transduction in the course of screening.

Various technologies may be employed for the screening, identification, and evaluation of compounds which interact with PKCε, which compounds may affect various cellular processes under the control of PKCε.

For example, PKCε or a functional derivative thereof, in pure or semi-pure form, in a membrane preparation, or in a whole live or fixed cell is incubated with the compound. Subsequently, under suitable conditions, the effect of the compound on the PKCε function is scrutinized, e.g., by measuring its activity, or its signal transduction, and comparing the activity to that of PKCε, incubated under same conditions, without the compound, thereby determining whether the compound stimulates or inhibits the PKCε activity.

In addition to the use of whole cells expressing PKCε for the screening of compounds, the invention also includes methods using soluble or immobilized PKCε. For example, molecules capable of binding to PKCε may be identified within a biological or chemical preparation. For example, PKCε, or functional fragments thereof, e.g., fragments containing a specific domain of interest, is immobilized to a solid phase matrix, subsequently a chemical or biological preparation is contacted with the immobilized PKCε for an interval sufficient to allow the compound to bind. Any unbound material is then washed away from the solid phase matrix, and the presence of the compound bound to the solid phase is detected, whereby the compound is identified. Suitable means are then employed to elute the binding compound.

1. Source of Candidate Test Compounds

The test compounds employed for such assays are obtained from any commercial source, including Aldrich (1001 West St. Paul Ave., Milwaukee, Wis. 53233), Sigma Chemical (P.O. Box 14508, St. Louis, Mo. 63178), Fluka Cherme AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasaao (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the assay cascade of the invention, including microbial, fungal or plant extracts.

2. Other PKCε Modulators and Their Properties

Although any molecule that inhibits the PKCε isozyme is sufficient to lessen anxiety or decrease alcohol consumption, molecules that selectively inhibit the PKCε isozyme are preferred because, as shown by PKCε-mutant mice, elimination of PKCε does not cause major developmental abnormalities or serious side effects. Since molecules also capable of inhibiting PKC isozymes other than PKCε interfere with the various functions performed by those isozymes, such nonselective inhibitors of PKCε, although they diminish anxiety or alcohol consumption, are likely to have many unwanted side effects;

There are many known inhibitors of PKCε that can be used in the instant invention. For instance, U.S. Pat. No. 5,783,405 describes a large number of peptides that inhibit PKC isozymes. Of these, the εV1-1, εV1-2, εV1-3, εV1-4, εV1-5, εV1-6 and εV1-7 peptides are selective for PKCε. Small molecule inhibitors of PKC are described in U.S. Pat. Nos. 5,141,957, 5,204,370, 5,216,014, 5,270,310, 5,292,737, 5,344,841, 5,360,818, and 5,432,198. These molecules belong to the following classes: N,N'-Bis-(sulfonamido)-2-amino-4-iminonaphthalen-1-ones; N,N'-Bis-(amido)-2-amino-4-iminonaphthalen-1-ones; vicinal-substituted carbocyclics; 1,3-dioxane derivatives; 1,4-Bis-(aminohydroxyalkylamino)-anthraquinones; furocoumarinsulfonamides; Bis-(hydroxyalkylamino)-anthraquinones; and N-aminoallyl amides. The relevant portions of foregoing patents are hereby incorporated by reference.

Additional inhibitors of PKCε can be identified using assays that measure the activation, intracellular translocation, binding to intracellular receptors (e.g. RACKs) or catalytic activity of PKCε. Traditionally, the kinase activity of PKC family members has been assayed using at least partially purified PKC in a reconstituted phospholipid environment with radioactive ATP as the phosphate donor and a histone protein or a short peptide as the substrate (T. Kitano, M. Go, U. Kikkawa, Y. Nishizuka, Meth. Enzymol. 124,349-352

(1986); R. O. Messing, P. J. Peterson, C. J. Henrich, J. Biol. Chem. 266, 23428-23432 (1991)). Recent improvements include a rapid, highly sensitive chemiluminescent assay that measures protein kinase activity at physiological concentrations and can be automated and/or used in high-throughput screening (C. Lehel, S. Daniel-Issakani, M. Brasseur, B. Strulovici, Anal. Biochem. 244, 340-346 (1997)) and an assay using PKC in isolated membranes and a selective peptide substrate that is derived from the MARCKS protein (B. R. Chakravarthy, A Bussey, J. F. Whitfield, M. Sikorska, R. E. Williams, J. P. Durkin, Anal. Biochem. 196, 144-150 (1991)). Inhibitors that affect the intracellular translocation of PKCε can be identified by assays in which the intracellular localization of PKCε is determined by fractionation (R. O. Messing, P. J. Peterson, C. J. Henrich, J. Biol. Chem. 266, 23428-23432 (1991)) or immunohistochemistry (U.S. Pat. No. 5,783,405; U.S. patent application Ser. No. 08/686,796). To identify an inhibitor of PKCε, the assays should be performed with PKCε. The selectivity of such PKCε inhibitors can be determined by comparing the effect of the inhibitor on PKCε with its effect on other PKC isozymes. The relevant portions of foregoing patents and publications are hereby incorporated by reference.

3. Indications for the Use of Compounds Interfering with PKCε Enzymatic Activity or Signal Transduction The compounds identified by the methods of the present invention are modulators of the enzymatic activity of PKCε, or, alternatively, modulators of protein/protein interactions in the PKCε-induced signal-transduction pathway. Such compounds may be useful for the treatment of a number of indications, including, but not limited to, anxiety, e.g., in conditions such as anxiety disorders, including panic disorder (e.g., panic disorder without agoraphobia, panic disorders with agoraphobia), agoraphobia without history of panic disorder, specific phobia, social phobia, obsessive-compulsive disorder, post-traumatic stress disorder, acute stress disorder, generalized anxiety disorder, substance-induced anxiety disorder, or anxiety disorder otherwise not specified.

E. Formulations/Route of Administration

The identified compounds can be administered to a human patient alone or in pharmaceutical compositions where they are is mixed with suitable carriers or excipient(s) at therapeutically effective doses to treat or ameliorate a variety of disorders. A therapeutically effective dose further refers to that amount of the compound sufficient to result in amelioration of symptoms as determined in a decrease of, e.g., a patient's anxiety. Techniques for formulation and administration of the compounds of the instant application may be found in "Remington's Pharmaceutical Sciences," Mack Publishing Co., Easton, Pa., latest edition.

1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer a compound of the invention in a local rather than systemic manner, for example, via injection of the compound directly into a solid tumor, often in a depot, or in a sustained release formulation.

Furthermore, one may administer the drug via a targeted drug delivery system, for example, in a liposome coated with tumor-specific antibody. The liposomes will be targeted to and taken up selectively by the tumor.

2. Composition/Formulation

Because PKCε is an intracellular protein, preferred embodiments of the invention involve pharmaceutically acceptable inhibitor formulations capable of permeating the plasma membrane. Small, apolar molecules are often membrane permeable. The membrane permeability of other molecules can be enhanced by a variety of methods known to those of skill in the art, including dissolving them in hypotonic solutions, coupling them to transport proteins, and packaging them in micelles.

The pharmaceutical compositions of the present invention may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g. by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the anxiety-inhibiting compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms, e.g. the symptom of anxiety, of the subject being treated. Determination of the effective amounts is well within the capability of those skilled in the art, especially in light of the detailed disclosure provided herein.

PKC$\epsilon$ inhibitors can be administered hourly, several times per day, daily or as often as the person undergoing treatment or that person's physician sees fit Preferably, the administration interval will be in the range of 8 to 24 hours. The severity of the patient's condition can be taken into account when determining appropriate intervals for PKC$\epsilon$ inhibitor treatments. PKC$\epsilon$ inhibitor treatments can continue over the course of several days, one month, several months, one year, several years or the duration of the patient's lifetime. Alternatively, PKC$\epsilon$ inhibitors can be administered on a one-time only basis. PKC$\epsilon$ inhibitors should be administered at levels sufficient to reduce produce the desired effect in the body of the patient. The skilled artisan will appreciate that increasing doses of PKC$\epsilon$ inhibitors should be administered until the patient experiences the desired modulation of symptoms, and larger doses fail to effect more desirable modulation.

Inhibitor dosage will vary according to many parameters, including the nature of the inhibitor and the mode of administration. For the $\epsilon$PKC-v1 peptide, a 150 µg/ml intracellular concentration inhibited PKC$\epsilon$ translocation and downstream effects of PKC$\epsilon$ activation (U.S. Pat. No. 5,783,405). Daily dosages in the range of 1 µg/kg-100 mg/kg of body weight, preferably 1 µg/1 kg-1 mg/kg and most preferably 10 µg/kg-1 mg/kg are contemplated for PKC inhibitors that are N,N'-Bis-(sulfonamido)-2-amino-4-iminonaphthalen-1-ones or N,N'-Bis-(amido)-2-amino-4-linonaphthalen-1-ones. Daily dosages in the range of 1 µg/kg-100 mg/kg of body weight, preferably 1 µg/kg-40 mg/kg and most preferably 10 g/kg-20 mg/kg are contemplated for PKC inhibitors that are vicinal-substituted carbocyclics. Daily dosages in the range of 5-400 mg/kcg of body weight, preferably 10-200 mg/kg and most preferably 10-50 mg/kg are contemplated for PKC inhibitors that are 1,4-Bis-(amino-hydroxyalkylamino)-anthraquinones, Bis-(hydroxyalkylamino)-anthraquinones, or N-aminoalkyl amides. Daily dosages in the range of 0.1-40 mg/kg of body weight, preferably 1-20 mg/kg, are contemplated for PKC inhibitors that arc 1,3-dioxane derivatives. Daily dosages in the range of 1-100 mg/kg of body weight are contemplated for PKC inhibitors that are furo-coumarinsulfonamides.

For any compound used in the method of the invention, the therapeutically effective dose can be estimated initially from cell culture assays. For example, a dose can be formulated in animal models to achieve a circulating concentration range that includes the $IC_{50}$ as determined in cell culture (ie., the concentration of the test compound which achieves a half-maximal inhibition of PKCε enzymatic activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred.

The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1 p 1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50-90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include amelioration of anxiety disorders, seizure disorders, cancer, cardiac arrhythmia, cardiac ischemia, pain, and the like.

F. Use of Modulators of PKCε to Alter Alcohol Consumption and Self-Administration of Other Drugs of Abuse and the Effects Thereof The inventors of the present invention have discovered that mutant mice lacking PKCε voluntarily consume significantly less alcohol than wild-type littermates, are much more sensitive to the locomotor activating and sedative effects of alcohol than wild-type littermates, and fail to experience the ethanol-induced peak in extracellular dopamine levels that occurs in the nucleus accumbens of wild-type littermates. Ethanol modulation of $GABA_A$ receptor function is also increased in cerebral cortex of mutant mice. These data indicate that PKCε regulates drinking preference, acute behavioral responses to ethanol and ethanol-mediated reward pathways in the brain.

Thus, the present invention includes methods for altering alcohol intake or self-administration of other drugs of abuse by administering a modulator of PKCε activity to a person desiring to modify his or her alcohol intake or drug use, respectively. The administration of an inhibitor of PKCε will cause the person to drink less alcohol or self-administer decreased quantities of drugs of abuse whereas an enhancer of PKCε activity will result in greater consumption of alcohol or a drug of abuse. Alcoholics, drug addicts and persons predisposed to alcoholism or addiction to other drugs of abuse are therefore preferred recipients of PKCε inhibitors. The most preferred embodiments decrease alcohol consumption by alcoholics. Such inhibitors of PKCε activity can be identified and/or administered by the methods discussed in section V.D above. While alcoholics and persons predisposed to alcoholism might receive PKCε inhibitors on a regular basis, those who wish to alter their alcohol consumption at a particular time might self-administer PKCε modulators at a time prior to, during or following alcohol ingestion. Preferably, the PKCε modulator would be present in the body at a time during which ethanol is also present and would be administered as part of a pharmaceutically acceptable formulation. In addition, PKCε modulators can be added directly to alcoholic beverages, and a composition comprising alcohol and a modulator of PKCε is one embodiment of the invention. Effective doses of such modulators can be established by the methods set forth in Section V.D.3. Alternatively, the range of effective doses may be established in mice by monitoring drinking behavior and comparing it with that evidenced by PKCε mutant mice. Such dosages could then be adjusted to account for differences between mice and the species of the subject to be treated.

Methods of modulating consumption of a drug of abuse that involve the administration of an effective amount of a selective inhibitors or selective enhancer of PKCε are preferred embodiments. Preferred selective inhibitors include the following peptides: εV1-1, εV1-2, εV1-3, εV1-4, εV1-5, εV 1-6 and εV1-7; a particular preference for the εV1-2 peptide is noted. Modulators of PKCε may be small molecule compounds (that is, compounds with a molecular weight of less than or equal to about 2000 daltons, preferably less than or equal to 1000 daltons and most preferably less than or equal to 500 daltons). PKCε inhibitors that inhibit the catalytic activity of PKCε or the intracellular translocation of PKCε may be administered in the methods of the present invention. Inhibitors that act directly on PKCε are preferred.

Another aspect of the invention is a method of modulating the effects of alcohol on the person drinking it. Since the inventors have shown that PKCε modulates effects of both low doses and high doses of alcohol, this method can be employed in a variety of ways to potentially alter different effects of alcohol, including effects on motor coordination or sedative effects. In one embodiment, a person who wishes to drink alcohol without becoming drunk could take an enhancer of PKCε. This might enable the person to experience the pleasures (taste, socializing, etc.) of alcohol consumption without fear of reduced capacity to operate machinery, participate in sports, or stay awake. In another embodiment, an individual might wish to experience the effects of alcohol without having to drink large quantities of alcohol. For example, a person could become pleasantly tipsy after just one drink, thereby avoiding the calories, expense, and other negative factors associated with consuming more alcohol. A pregnant woman at risk for premature delivery could experience the early labor forestalling effects of alcohol without exposing her fetus to high levels of alcohol.

Dopamine released in the nucleus accumbens from presynaptic terminals of neurons projecting from the midbrain ventral tegmental area (VTA) is a major mediator of drug reward and reinforcement Acute administration of all abusable drugs increases extracellular levels of dopamine in the nucleus accumbens and dopamine receptor antagonists injected into this region reduce alcohol and drug self-administration in animals (Di Chiara, G., and Imperato, A., Proc. Natl. Acad. Sci. USA 85, 5274-5278 (1983); Hodge et al, Pharmacol Biochem Behav 48:141-150 (1994)). The VTA and nucleus accumbens have been identified as key structures involved in drug reward and motivational aspects of drug dependence (Koob et al., Neuron 21, 467-476 (1998)) and are components of the mesocorticolimbic dopamine system that is now a principal focus of addiction research.

The finding that ethanol does not elevate dopamine-levels in the nucleus accumbens in PKCε$^{-/-}$ mice suggests that either dopamine reuptake in the nucleus accumbens is increased or the secretion of dopamine by VTA neurons in the nucleus accumbens is suppressed in these mice. Although the mechanisms by which abusable drugs promote dopamine release vary,[7] either mechanism for PKCε's effect on ethanol-induced heightened dopamine levels discussed in the previous sentence would suppress the ability of other abusable drugs to elevate extracellular dopamine levels in the nucleus accumbens. Given that dopamine release in the nucleus accumbens is important for the rewarding properties of abusable drugs, it is very likely that PKCε$^{-/-}$ mice will show reduced self administration of other abusable drugs besides alcohol. That would indicate a role for PKCε inhibitors in the treatment of addiction to several drugs of abuse, as was discussed above in the relationship of diagnostic methods for identifying individuals at risk for becoming alcoholics or abusers of other drugs.

[7] Cocaine and amphetamine inhibit dopamine reuptake at VTA nerve terminals thereby increasing the concentration of dopamine at synapses in the nucleus accumbens (Amara, S. G., and Sonders, M. S., Drug Alcohol Depend. 51, 87-96 (1998)). Opiates act by a different mechanism. Normally in the VTA, GABA-containing neurons suppress firing of dopaminergic VTA neurons that project to the nucleus accumbens. Opiates disinhibit these dopaminergic neurons by binding to opioid receptors expressed by the GABA-containing neurons (Wise, R. A., Curr. Opin. Neurobiol. 6, 243-251 (1996)). This increases the firing rate of dopaminergic VTA neurons and promotes dopamine release in the nucleus accumbens. Nicotine directly activates VTA dopaminergic neurons (Wise, R. A., Curr. Opine Neurobiol. 6, 243-251 (1996)). Ethanol also activates dopaminergic VTA neurons directly by altering ion channel function (Brodie, M. S., and Appel, S. B., Alcoholism, Clinical and Experimental Research 22, 236-244 (1998)). This increases the firing rate of these neurons and stimulates dopamine release in the nucleus accumbens.

G. Use of Inhibitors of PKCε to Treat Anxiety, Addiction, Withdrawal Syndrome, Muscle Spasms, Convulsive Seizures, and Epilepsy The inventors of the present invention have discovered that PKCε mutant mice are also significantly more sensitive to the locomotor activating and sedative effects of allosteric $GABA_A$ receptor agonists. Benzodiazepine modulation of $GABA_A$ receptor function is also increased in cerebral cortex of mutant mice. Because the mutation reduced PKCε immunoreactivity in whole-brain homogenates to undetectable levels without significantly altering levels of other PKC isozymes, the effects on $GABA_A$ receptor function are due to the absence of PKCε rather than alterations of other PKC isozymes. These data indicate that PKCε regulates the response of $GABA_A$ receptors to allosteric agonists. As such, modulators of PKCε define a new class of drugs that act as selective modulators of allosteric agonists of $GABA_A$ receptors. The heightened levels of taurine observed in PKCε$^{-/-}$ mice show that the enhanced $GABA_A$ receptor activity seen in these mice is due, in part, to the increased levels of an allosteric $GABA_A$ receptor agonist.

Because the inventors have shown that PKCε modulates both endogenous and non-endogenous allosteric agonists of $GABA_A$ receptors, PKCε inhibitors may be administered either alone or in combination with such allosteric agonists to treat conditions remediated by increasing $GABA_A$ receptor activity. Such conditions include anxiety, addiction, withdrawal syndrome, skeletal muscle spasms, convulsive seizures, and epilepsy. Anxiety may be due to a number of circumstances, including without limitation, anticipation of a painful event or the performance of a surgical or endoscopic procedure, in which case it is preferable to administer the inhibitor of PKCε prior to the administration of anesthesia. Withdrawal syndromes treated by PKCε inhibitors alone or together with allosteric agonists of $GABA_A$ receptors include those induced by ethanol or any other sedative-hypnotic drug the withdrawal from which is characterized by seizures and autonomic hyperactivity. Treatment of withdrawal symptoms due to alcohol or drugs having withdrawal syndromes that may be ameliorated by administration of alcohol are preferred.

Treating a patient with a combination of one or more PKCε inhibitors and one or more allosteric agonists of $GABA_A$ receptors is preferable to prior art treatments which employed only allosteric agonists of $GABA_A$ receptors because the combination therapy allows the same therapeutic effect to be achieved with a lower dose of allosteric agonists of $GABA_A$ receptor, thereby minimizing the undesirable side effects, such as addiction and sedation, of the allosteric agonists. Thus, the present invention also involves a method for reducing the effective dose of an allosteric agonist of a $GABA_A$ receptor by administering a PKCε inhibitor in conjunction with such allosteric agonist of a $GABA_A$ receptor.

Another aspect of the invention is a composition comprising an inhibitor of PKCε and an allosteric agonist of a $GABA_A$ receptor. Benzodiazepines and barbituates are preferred allosteric agonists. Benzodiazepines that may be used in this composition and in any method employing such composition include, without limitation, alprazolam, chlordiazepoxide, chlordiazepoxide hydrochloride, chlormezanone, clobazam, clonazepam, clorazepate dipotassium, diazepam, droperidol, estazolam, fentanyl citrate, flurazepam hydrochloride, halazepam, lorazepam, midazolam hydrochloride, oxazepam, prazepam, quazepam, temazepam, and traizolam. Amobarbital, amobarbital sodium, aprobarbital, butabarbital sodium, hexobarbital sodium, mephobarbital, metharbital, methohexital sodium, pentobarbital, pentoberbital sodium, phenobarbital, phenobarbital sodium, secobarbital, secobarbital sodium, talbutal, thiamylal sodium, and thiopental sodium are barbituates suitable for use in the present invention.

H. Diagnostic Methods for Identifying Alcoholism- and/or Addiction-Prone Individuals There is growing evidence that genetic factors influence behavioral responses to alcohol in mammals (J. C. Crabbe, J. K. Belknap, K. J. Buck, Science 264, 1715-23 (1994); K. Demarest, J. McCaughran, Jr., E. Mahjubi, L. Cipp, R. Hitzemann, Journal of Neuroscience 19, 549-61 (1999)). In human populations, alcohol abuse and alcoholism have been widely demonstrated to have a genetic component, but information concerning specific responsible genes is limited (V. Hesselbrock, in The Genetics of Alcoholism H. Begleiter, B. Kissin, Eds. (Oxford, N.Y., 1995) pp. 17-39; T. Reich, et al., American Journal of Medical Genetics 81, 207-15 (1998)). Evidence indicates that acute sensitivity to alcohol may predict genetic risk for development of alcoholism. Sons of alcoholics who demonstrated greater acute responses to ethanol were less likely to become alcoholics than those who demonstrated lower responses (M. A. Schuckit, American Journal of Psychiatry 151, 184-9 (1994)). Although the genetics of addiction to drugs of abuse other than alcohol are not well understood, many persons are prone to addiction to more than one drug of abuse. The inventors of the present invention have discovered that mutant mice lacking the gene for PKCε are more sensitive to acute doses of ethanol and self-administer much less ethanol than wild-type mice, and they do not achieve a peak in dopamine levels after administration of ethanol. This indicates that the PKCε gene influences ethanol sensitivity and the risk of developing alcoholism and/or addiction to another drug of abuse. A test which determines the activity of the PKCε proteins encoded by a person's genes and uses such information to predict the likelihood that such person will become an alcoholic is another aspect of the present invention. A kit for performing such a test is yet another embodiment of the present invention.

An individual's PKCε activity level can be determined in a number of ways. For example, the nucleic acids encoding each of the person's two PKCε alleles can be sequenced and the amino acid sequence of the encoded PKCε protein can be deduced. If both amino acid sequences are identical to the sequence of the wild-type PKCε protein and no mutations are discovered in non-coding portions of the gene that may be regulatory, then such person's PKCε activity can be assumed fall within the range of PKCε activities reported in individuals from a control population and such person shall be classified as not having a predisposition to become an alcoholic. If either of the PKCε amino acid sequences differs from the sequence of the wild-type PKCε protein, the activity of such "mutant" PKCε protein can be determined by methods such as: 1) determining if the activity of such "mutant" PKCε protein has been previously measured; 2) expressing the "mutant" PKCε protein in vitro or in test cells and assaying its activity by known methods; or 3) running a computer simulation of the activity of such "mutant" PKCε protein. If there is a mutation in a non-coding region, any effect of such mutation on PKCε expression can be assessed by direct measurement of transcription, translation or amount of PKCε protein.

Alternatively, a sample containing PKCε protein can be obtained from the individual being tested and the activity of said PKCε protein can be directly measured by one of the many assays for PKCε activity.

If the sample is to be used for nucleic acid analysis, it may be obtained from any cell or tissue source possessing nuclear DNA. If the sample is to be used for protein analysis, it must be collected from cells or tissues in which the PKCε protein is present. Such cells or tissues include neurons, astroglial cells, Purkinje cells, lymphocytes, neutrophils and epidermal keratinocytes.

The individual's PKCε activity level is compared with a standard value to determine the likelihood that the individual will become an alcoholic. The standard value is usually (1) a range of PKCε activity levels for the same type of sample in a control population or (2) a range of PKCε activity levels for the same type of sample in a control population of alcoholics. It is apparent that comparison with both standard values (1) and (2) may be possible and may provide confirmatory evidence of the likelihood that the individual will become an alcoholic.

The first general standard value set out above, a range of PKCε activity levels for the same type of sample in a control population, is typically obtained by using the same assay technique that will be used in the application of the method to the sample being tested in order to ensure the highest correlation. Sufficient measurements are made within the appropriate control population to produce a statistically significant range of control values to which a comparison will be made. It is appreciated that the appropriate control population will vary depending upon the particular patient being tested.

Preferably, the control population is selected such that its members do not suffer from alcoholism and approximately match the patient being tested with respect to any characteristic or condition (other than alcoholism) known to affect PKCε activity levels. The range of PKCε activity levels determined from this population thus serves as a baseline value for PKCε concentration or activity for the individual patient being tested. In many cases, the appropriate control population will consist of normal, healthy humans. A control population consisting of normal healthy humans will be appropriate particularly when the patient being tested is free of conditions unrelated to alcoholism that may contribute to an increase in PKCε activity levels. When the patient being tested is known to have a condition, other than propensity towards alcoholism, that is associated with elevated PKCε levels, the appropriate control population is preferably a population having the same condition.

The foregoing discussion is not to suggest, however, that an actual control population must be measured for every application of the method of the present invention. Once a clinically satisfactory standard is established, this predetermined standard range can be used for subsequent evaluations without additional testing of control populations. It is also possible to relate the PKCε level for any patient to normal human controls by taking into consideration elevated PKCε levels associated with other disorders.

It will be apparent that to obtain the first general standard value set out above, the PKCε concentration or activity for the appropriate control population can be determined in a number of ways. For example, it can be estimated from values in the relevant scientific or clinical literature, it can be constructed from a combination of measured values and estimated adjustment factors (i.e. adjustments for the presence or absence of a condition, other than propensity towards alcoholism, affecting PKCε activity), or it may be actually measured.

The second general standard value set out as an alternative above is a range of PKCε concentrations or activities from the same type of sample in a population of alcoholics. Typically the measurement of PKCε concentrations or activities in the population of alcoholics is taken using the same technique as that used in the test application.

When either general standard value is used for comparison with the PKCε value of the sample being analyzed, the threshold concentration or activity indicative of increased likelihood of becoming an alcoholic can be determined by any appropriate statistical method. The concentration or activity set above the mean of the predetermined PKCε concentration or activity range for the appropriate control population will indicate the threshold above which the onset of alcoholism is likely to occur with a particular level of certainty. It will be recognized by those familiar with statistics that the number of standard deviations used as a positive indication of predisposition for alcoholism will be selected with an appropriate diagnosis goal in mind. A concentration or activity greater than one standard deviation from the mean may correlate with predisposition for alcoholism, particularly in combination with other risk factors. A concentration or activity greater than two standard deviations from the mean generally indicates statistical significance and is predictive of predisposition for alcoholism. A concentration or activity value greater than three standard deviations is accordingly predictive of predisposition for alcoholism with a higher degree of certainty, and values greater than four standard deviations will be predictive of predisposition for alcoholism with a still higher degree of certainty. It will also be recognized that concentration or activity levels falling outside the range observed for the control population are statistically significant values. Preferably, a particular concentration or activity of PKCε considered to reflect a positive indication of predisposition for alcoholism is best selected by the attending physician and will vary depending on the condition of the patient as well as the presence of other risk factors for developing alcoholism.

Persons constituting a population of alcoholics from whom such a second standard value can be obtained may be identified as those individuals who meet the criteria set forth in for alcohol dependence.

Thus, one aspect of the present invention is a method of determining a person's susceptibility to alcoholism or drug dependence. The method can be practiced by determining the person's activity or concentration of PKCε and assigning the person a addiction risk factor which correlates with the percentage of drug abusers among a statistically significant group of persons having the approximately the same activity or concentration of PKCε. Alternatively, the method can be practiced by analyzing PKCε activity or concentration in a appropriate sample (i.e., one that contains PKCε or nucleic acid encoding PKCε from the person) and comparing the person's PKCε activity or concentration with a standard value selected from a range of PKCε activities or concentrations, respectively, for similar samples obtained from a population of persons having a known characteristic with respect to dependence on a drug of abuse and relating said activity or concentration of PKCε to said standard value, wherein a statistically different activity or concentration is predictive of the degree of likelihood of said person becoming dependent upon or an abuser of said drug of abuse.

Another embodiment of the invention is a kit or article of manufacture that comprises an ingredient for assaying PKCε activity or concentration in an appropriate sample and instructions for comparing said PKCε activity or concentration with a predetermined standard value, and determining whether a statistically significant difference exists between said PKCε activity or concentration and said predetermined standard value is predictive of increased or decreased likelihood of becoming dependent upon or an abuser of a drug of abuse.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent-are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

A. Example 1

Generation of A PKCε$^{-/-}$ Mouse

Ethanol potentiates NGF-induced activation of mitogen-activated protein kinases and neurite outgrowth in PC12 cells by a PKCε-dependent mechanism (Roivainen et al., 1993, *Brain Res.* 624:85-93; Roivainen et al., 1995, *Proc. Natl. Acad. Sci. USA* 92:1891-1895; Hundle et al., 1995, *J. Biol. Chem.* 270:30134-30140; Hundle et al., 1997, *J. Biol. Chem.* 272:15028-15035). Since neural plasticity (Nestler and Aghajanian, 1997, *Science* 278:58-63) may contribute to drug dependence, we became interested in the role of PKCε in behavior-modulating effects in mice. The following describes the generation of PKCε$^{-/-}$ mice by homologous recombination (Joyner A J, ed. *Gene Targeting*. The Practical Approach Series, ed. Rickwood D. and Harries B. D. 1993, IRl Press: New York).

A strategy was designed to create a targeting vector that would "knock out" 1.2 kb of the genomic DNA sequence for mouse PKCε, including all of exon I and part of the downstream intron sequence. To create a targeting vector, we amplified an 813 bp fragment (nt 470-1282) from mouse PKCε cDNA (94) by PCR. This fragment was used to screen a lambda FLX 11 129 mouse liver genomic library (Stratagene #946308) (Stratagene, La Jolla, Calif.). Two 13 kb and 15 kb overlapping genomic clones were selected and subcloned into the Nod site of pBluescript 11 SK+ (Stratagene). The clones were digested with BamHI and EcoRI restriction enzymes and fragments subcloned into pbluescript II SK+. The subclones were analyzed by restriction digestion with twenty (20) enzymes to construct a genomic map. Several clones were used identify ~1700 bp of sequence 5' to the ATG start codon.

FIG. 1 depicts the generation of PKCε$^{-/-}$ mice. A unique Apa I site (A*) introduced by the targeting vector (FIG. 1A) allows detection of a 1.6 kb fragment on Southern blots of Apa I and Sca I digests of mutant genomic DNA. FIG. 1B shows a Southern blot of tail samples from mouse pups born to heterozygous progeny of male chimeras and C5Bl/6J females, in which the 1.6 kb fragment has been visualized with radioactively labeled probes. Lanes containing samples from 7 homozygous knockouts are labeled by sex. FIG. 1C depicts a Western blot with anti-PKCε antibody of brain samples from wild-type (+/+), heteroygous (+/−) and knockout littermates.

A 1.0 kb BssH II "short arm" fragment (beginning 60 bp 5' from the ATG start codon) was cloned into the BamHI site of the vector pNTK (Steward et a., 1987, *EMBO J.* 6:383-388; *Current Protocols in Molecular Biology*, by: Ausubel et al., eds., 1993, J. Wiley & Sons, Unit 9.16). This vector contains a neomycin resistance gene for positive selection and a herpes simplex virus thymidine kinase (TK) sequence for negative selection, both driven by PGK promoters. A 6.1 kb Stu I genomic "long-arm" fragment downstream of the first exon of PKCε was cloned into the Hind III site of the pNTK construct containing the short arm sequence. The completed construct was then linearized with Cla I and transfected by electroporation into 129/RF8 embryonic stem cells. Meiner et a., 1996, *Proc. Natl. Acad. Sci. USA* 93:14041-14046. Clones were selected by culture in the presence of neomycin and FIAU. Four hundred resistant colonies were expanded and examined by Southern analysis. Nine correctly targeted clones were identified and two were microinjected into embryonic day 3.5 C57BL/6J blastocysts. Three male chimeras with 80-90% agouti coat color were mated with C57BL/6J females. Germ-line transmission was documented by Southern analysis using a probe that detects a novel 1.6 kb DNA fragment after digestion with Sca I and Apa I (FIG. 1). Mating of heterozygous mice initially produced seven mice homozygous for the mutation, and Western analysis of one animal revealed the absence of PKCε immunoreactivity in brain (FIG. 1) without a compensatory increase in levels of other PKC isozymes (FIG. 2).

B. Example 2

CNS Morphology in PKCε-/- Mice

Using the procedure described in Example 1, a total number of over 80 PKCε$^{-/-}$ mice has been identified. The CNS morphology in the mutant mice has been characterized as follows.

The overall brain structure appears normal both grossly, and microscopically by hematoxylin and eosin staining. However, fiber staining reveals structural abnormalities in the stratum radiatum of the CAI sector in 6-month old knockout mice. There, MAP-2 immunoreactive apical dendrites are shorter and appear to branch earlier than in wild-type littermate controls (FIG. 3). In addition, staining for acetylcholinesterase reveals a decrease in cholinergic innervation of the hippocampus of PKCε$^{-/-}$ mice (FIG. 4). Despite these alterations in hippocampal morphology, no deficit in spatial learning was found in 6 week-old PKCε$^{-/-}$ mice as assessed by Morris water maze.

C. Example 3

Behavioral Studies in PKCε-/- Mice

The following is an analysis of the behavior of PKCε$^{-/-}$ mice.

Basic Characterization. PKCε$^{-/-}$ mice demonstrated normal body weight, eating, drinking over a two-week period as compared to litter-mate wild-type controls at about 60 days of age (FIG. 5). Similarly, PKCε mice demonstrated normal spontaneous locomotor behavior and habituation to a novel environment as compared to wild-type controls during three daily 1-hour tests (FIG. 6 and TABLE 1).

Anxiety Related Behavior. Although PKCε$^{-/-}$ mice exhibited normal gross locomotor behavior, further analysis revealed that they differed significantly from wild-type controls on specific measures of open-field activity, exploration of a novel object, and elevated plus maze performance. For instance, PKCε$^{-/-}$ mice demonstrated a two-fold increase in distance traveled, and a three-fold increase in time spent resting, in the center area of the open-field (FIGS. 7 and 8). Both of these findings are consistent with reduced anxiety levels in the mutant mice. The PKCε$^{-/-}$ mice also demonstrated a two-fold increase in exploratory behavior when a novel object was placed in the center of an open-field, which also suggests reduced anxiety levels. Moreover, when tested in the elevated plus maze, a well defined test of anxiety, PKCε$^{-/-}$ mice exhibited twice the distance traveled, visit time, ambulatory time, and rest time in the open arms as compared to controls (FIG. 9). These data represent the novel finding the PKCε plays an important role in regulating anxiety.

Sedative Effects of Ethanol and GABA$_A$ Agonist. GABA$_A$ receptors are widely known to mediate the sedative effects of ethanol (Allan and Harris, 1987, *Pharmacol. Biochem. Behav.* 27:665-670; Mehta and Ticku, 1988, *J. Pharmacol. Exp. Ther.* 246:558-564). However, the relationship between GABA$_A$ receptor sensitivity to effects of ethanol and the protein kinase C epsilon (PKCε) isozyme is less defined. One purpose of this study was to determine if the PKCε isozyme is involved in modulating the sedative effects of ethanol as measured by the onset and duration of an ethanol-induced loss of righting reflex (LORR). Mutant mice lacking PKCε and wild-type controls were injected with three doses of ethanol (3.2, 3.6, and 4.0 g/kg/i.p.), after which latency and duration of LORR were measured. All mice showed a dose-dependent increase in LORR duration. PKCε-knockout mice were found to have significantly higher LORR duration than wild-type controls (FIG. 10). In order to determine if this effect was mediated by changes in GABA$_A$ receptor activity, we tested the effects of sedative doses of the GABA$_A$ agonist pentobarbital. PKCε$^{-/-}$ mice demonstrated two-fold greater sensitivity to the sedative effects of pentobarbital (FIG. 11). This suggests that PKCε modulates the sedative effects of ethanol through GABA-ergic mechanisms. Updated versions of these experiments are described in Examples 5 and 6 below and depicted in FIGS. 13C and 14A.

D. Example 4

Alcohol Consumption in PKCε-/- Mice is Significantly Less Than That of Their Wild-Type Littermates To determine whether PKCε modulates ethanol consumption, ethanol preference drinking was compared in wild-type mice and mutant mice lacking PKCε. Ethanol preference drinking was examined using a published method (C. Hodge, C. Slawecki, A. Aiken, *Alcohol Clin Exp Res* 21, 250-260 (1996)) by which mice have continuous access to two drinking bottles, one containing water and the other containing an ascending range of ethanol concentrations. 12 PKCε$^{+/+}$ and 12 PKCε$^{-/-}$ mice were tested in parallel. Following a one-

TABLE I

|  | Day 1 | | Day 2 | | Day 3 | |
| --- | --- | --- | --- | --- | --- | --- |
|  | PKCε$^{+/+}$ | PKCε$^{-/-}$ | PKCε$^{+/+}$ | PKCε$^{-/-}$ | PKCε$^{+/+}$ | PKCε$^{-/-}$ |
| Horizontal Dist, in | 4300 ± 239 | 4800 ± 215 | 2517 ± 593 | 3327 ± 223 | 2459 ± 521 | 4300 ± 239 |
| Ambulatory events | 4110 ± 596 | 4531 ± 453 | 2308 ± 496 | 2375 ± 580 | 2242 ± 511 | 2796 ± 498 |
| Time ambulatory, sec | 502 ± 53 | 554 ± 46 | 286 ± 53 | 286 ± 58 | 275 ± 55 | 327 ± 54 |
| Rearing events | 321 ± 53 | 359 ± 54 | 169 ± 30 | 203 ± 49 | 166 ± 35 | 216 ± 47 | week acclimatization period during which water was the only fluid available, the mice were given a choice between ethanol (2% w/v) and water. Two-bottle drinking sessions were conducted 23 hours per day, 7 days per week. During the course of the exposure period, ethanol concentration was increased from 2.0% to 14%, with the mice having four days of access to each of the following concentrations of ethanol: 2, 4, 6, 10, 14%. Each day, the mice were weighed and placed in individual holding chambers while the fluids where attached to the home cage. Initial fluid levels were recorded to the nearest milliliter at the beginning and end of 23 hour fluid access periods. The position (left or right) of each solution was alternated daily to control for side preferences.

PKCε mutant mice (PKCε$^{-/-}$) voluntarily consumed significantly less ethanol than wild-type littermate control (PKCε$^{+/+}$) mice (FIG. 12A). Although both genotypes preferred water to ethanol, PKCε$^{-/-}$ mice demonstrated a 75% reduction in ethanol preference as compared to PKCε$^{+/+}$/mice (FIG. 12B). No differences were observed in daily fluid intake during tests of ethanol preference drinking (ethanol+ water mls: 6.6±0.3 for PKCε$^{+/+}$ vs. 6.2±0.24 for PKCε$^{-/-}$)

Since reductions in ethanol intake may be influenced by a general disruption of appetite or fluid balance, daily body weights and consumatory behavior by PKCε$^{-/-}$ and PKCε$^{+/+}$ mice were measured over a two-week period. There were no significant differences in body weight, food, or water intake between the genotypes (FIGS. 12C, D, E). Given that differential taste reactivity may also influence ethanol intake, one month after the ethanol self-administration procedure, the same mice were tested for saccharin (sweet) and quinine (bitter) intake and preference in an order-balanced experimental design that can detect taste neophobias (J. C. Crabbe, et al., *Nature Genetics* 14, 98-101 (1996)). Saccharin sodium salt and quinine hemisulphate salt (Sigma, St. Louis, Mo.) were dissolved in tap water. These solutions are used for their strong tastes, lack of caloric value, and absence of confounding pharmacological effects. There were no significant differences in average saccharin (FIG. 12F) or quinine (FIG. 12G) intake over two days at each concentration, or preference relative to water, between PKCε$^{-/-}$ and PKCε$^{+/+}$ mice. Thus, reduced ethanol intake and ethanol preference by PKCε$^{-/-}$ mice do not appear to be related to genotypic deficits in consumatory behavior or to specific taste neophobias.

E. Example 5

PKCε-/- Mice are Hypersensitive to Activating and Sedative Effects of Ethanol

Because both diminished risk of developing alcoholism in humans and reduced voluntary ethanol intake in mice are associated with increased sensitivity to acute effects of ethanol (M. A. Schuckit, *American Journal of psychiatry* 151, 184-9 (1994); T. E. Thiele, D. J. Marsh, L. Ste. Marie, I. L. Bernstein, R. D. Palmiter, *Nature* 396, 366-9 (1998)), the sensitivity of PKCε$^{-/-}$ mice to acute effects of ethanol was tested. In mice, low doses of acute ethanol produce locomotor activation, whereas high doses result in sedation (D. A. Finn, P. J. Syapin, M. Bejanian, B. L. Jones, R. L. Alkana, *Alcoholism, Clinical and Experimental Research* 18, 382-6 (1994); G. D. Frye, G. R. Breese, *Psychopharmacology* 75, 372-9 (1981)).

Spontaneous locomotor activity and habituation of naive PKCε$^{-/-}$ (n=6) and PKCε$^{+/+}$ (n=6) mice was measured in Plexiglas chambers (17×17 in) located in sound-attenuating cubicles equipped with exhaust fans that masked external noise (Med Associates, Lafayette, Ind.). Two sets of 16 pulse-modulated infrared photobeams were placed on opposite walls at 1-inch centers to record X-Y ambulatory movements. Activity chambers were computer-interfaced (Med Associates, Lafayette, Ind.) for data sampling at 100-millisecond resolution. Mice were handled and weighed daily for 1 week prior to activity testing. Horizontal distance traveled (cm) was recorded for 1 hour on each of three days. These experiments demonstrated that spontaneous locomotor activity and habituation to a novel environment did not differ between mutant and wild-type mice (FIG. 13A).

However, when male mice were administered an acute intraperitoneal injection of 2 g/kg ethanol (an amount sufficient to induce locomotor activation) immediately before the start of activity monitoring, PKCε$^{-/-}$ mice demonstrated a two-fold greater increase in locomotor activity over a 15-minute period than PKCε$^{+/+}$ mice (FIG. 13B).

Following administration of a range of sedative doses of ethanol (3.2, 3.6, and 4.0 g/kg/i.p.), mice were intermittently placed on their backs and tested for loss or righting reflex (LORR). LORR was defined as the inability to complete a righting reflex within a 30-s interval. The duration of LORR was defined as the time interval between LORR and the return of the righting reflex. PKCε$^{-/-}$ mice showed a dose-related two-fold increase in the time required to regain their righting reflex as compared to PKCε$^{+/+}$ littermates (FIG. 13C).

To test whether the increased sensitivity to ethanol observed in PKCε$^{-/-}$ mice is due to differential absorption, distribution, or clearance of ethanol, blood ethanol concentrations at 10-180 min post intraperitoneal administration of ethanol (4.0 g/kg) were measured by drawing a 20 µl blood sample from the tail vein. Blood was added to a centrifuge tube containing 1.8 ml trichloroacetic acid solution and mixed by vortexing. Samples were analyzed using the Sigma Alcohol Diagnostic Kit 332 (Sigma, St. Louis, Mo.). Ethanol clearance showed a normal pattern (consistent with that reported in (T. Miyakawa, et al., *Science* 278, 698-701 (1997)) in both PKCε$^{-/-}$ and PKCε$^{+/+}$ mice (FIG. 13D). Thus, differential sensitivity to the acute locomotor activating and sedative effects of ethanol observed between PKCε$^{-/-}$ and PKCε$^{+/+}$ mice appears to be directly attributable to the loss PKCε activity rather than a function of differential motor ability or ethanol kinetics in the mutant mice.

F. Example 6

PKCε-/- Mice Exhibit Enhanced Sensitivity to Activating and Sedative Effects of Allosteric GABA$_A$ Agonists and Normal Sensitivity to Direct GABA$_A$ Agonists and NMDA Antagonists A number of ethanol's effects on brain and behavioral processes are mediated by changes in GABA$_A$ receptor function (C. W. Hodge, A. A. Cox, *Psychopharmacology* 139, 95-107 (1998); A. Allan, R. Harris, *Pharmacology, Biochemistry & Behavior* 27, 665-670 (1987)). Biochemical evidence indicates that GABA$_A$ receptors can be directly phosphorylated by PKC and that PKC regulates GABAergic currents in hippocampal CA1 neurons (B. J. Krishek, et al., *Neuron* 12, 1081-95 (1994); P. Poisbeau, M. C. Cheney, M. D. Browning, I. Mody, *Journal of Neuroscience* 19, 674-83 (1999); J. Weiner, C. Valenzuela, P. Watson, C. Frazier, T. Dunwiddie, *Journal of Neurochemistry* 63, 1949-1959 (1997)). Similarly, NMDA receptors mediate acute responses to ethanol, and they are phosphorylated by PKC (D. M. Lovinger, G. White, F. Weight, *Science* 243, 1721-1724 (1989); P. C. Suen, et al., *Brain Research. Molecular Brain Research* 59, 215-28 (1998)). To examine potential links between PKCε and GABA$_A$ receptor function or NMDA receptor function, the effects of allosteric GABA$_A$ agonists, direct GABA$_A$ agonists and NMDA antagonists in PKCε$^{-/-}$ and PKCε$^{+/+}$ mice were tested.

Following intraperitoneal injection of 30, 40, or 50 mg/kg Pentobarbital or 20, 30, or 40 mg/kg Diazepam, loss of righting reflex (LORR) was tested in PKCε$^{-/-}$ and PKCε$^{+/+}$ mice as in Example 5. Mutant mice demonstrated a dose-related three-fold greater sensitivity to the sedative effects of pentobarbital, an allosteric GABA$_A$ agonist, as compared to control mice (FIG. 14A). Moreover, PKCε$^{-/-}$ mice were 30-fold more sensitive to the sedative effects of diazepam, a more selective allosteric GABA$_A$ agonist than pentobarbital and a member of the benzodiazepine family (FIG. 14B).

Because a full dose-response curve for the sedative effects of diazepam in PKCε$^{-/-}$ mice could not be determined due to the fact that lower doses did not reliably produce the loss of righting reflex (LORR) measure in either genotype, the locomotor activating effects of 0.5, 1.5, and 4.0 mg/kg intraperitoneal injection of diazepam in PKCε$^{-/-}$ and PKCε$^{+/+}$ mice were evaluated by the methods described in Example 5. Mutant mice showed a significant increase in distance traveled following acute injections of diazepam as compared to wild-type mice (FIG. 14C).

In contrast to the enhanced sensitivity of PKCε$^{-/-}$ mice to the allosteric GABA$_A$ agonists diazepam and pentobarbital, the locomotor response of PKCε$^{-/-}$ mice to 0.1, 0.2 and 0.4 mg/kg intraperitoneal injections of muscimol, a direct GABA$_A$ agonist, was indistinguishable from that of similarly treated PKCε$^{+/+}$ mice (FIG. 14D).

Finally, the locomotor activating effects of 0.01, 0.02, 0.03 mg/kg intraperitoneal injections of the un-competitive NMDA antagonist MK-801 were examined by the methods described in Example 5. No differences were observed between mutant and wild-type mice in their responses to MK-801 (FIG. 14E).

These data demonstrate that PKCε$^{-/-}$ mice are hypersensitive to the acute sedative and locomotor activating effects of allosteric GABA$_A$ agonists such as barbituates and benzodiazepines, but are not differentially affected by a direct GABA$_A$ agonist or an NMDA antagonist.

G. Example 7

GABA$_A$ Receptor Function is Altered in PKCε−/− Mice and Wild-Type Mice Treated with An Inhibitor of PKCε

The increased sensitivity of PKCε$^{-/-}$ mice to ethanol, pentobarbital, and diazepam demonstrated in Examples 5 and 6 suggests that PKCε may selectively influence allosteric modulation of GABA$_A$ receptors. GABA$_A$ receptor function was tested directly in wild-type and mutant mice. Since GABA$_A$ receptors are ligand-gated ion channels whose activation increases Cl$^{31}$ conductance, GABA$_A$ receptor function was monitored by measuring $^{36}$Cl$^{31}$ flux in membrane vesicles (microsacs) prepared from frontal cortex using a modified version of published methods (Leidenheimer, N. J., McQuilkin, S. J., Hahner, L. D., Whiting, P. & Harris, R. A. Activation of protein kinase C selectively inhibits the γ-aminobutyric acid$_A$ receptor: role of desensitization. *Mol. Pharmacol.* 41, 1116-1123 (1992); Harris, R. A. & Allan, A. M. Functional coupling of gamma-aminobutyric acid receptors to chloride channels in brain membranes. *Science* 228, 1108-10 (1985)) in which the assay buffer contained the following protease inhibitors: 40 μg/ml leupeptin, 40 μg/ml aprotinin, 25 μg/ml soybean trypsin inhibitor, and 1 mM phenylmethylsulfonyl fluoride. Following a five minute incubation in a shaking water bath at 34° C., chloride uptake in 200 μl membrane aliquots was initiated by the addition and immediate vortexing of 200 μl of a solution containing $^{36}$C$^{31}$ (0.2 μCi/ml of assay buffer). Drugs (muscimol, flunitrazepam, or ethanol) were added only in the $^{36}$Cl$^-$ solution. Five seconds following the addition of $^{36}$Cl$^-$, influx was terminated by the addition of 4 ml of ice cold assay buffer and rapid filtration under vacuum (10-15 in. Hg) onto a 2.5 cm Whatman GF/C glass microfiber filter, using a Hoefer manifold (Hoefer Scientific, San Francisco, Calif.). The filters were washed with an additional 12 ml of cold assay buffer. Filters were submerged in Filtron-X (National Diagnostics) and the amount of radioactivity on the filters was determined by liquid scintillation spectrometry. Muscimol-dependent uptake was defined as the total amount of $^{36}$Cl$^-$ taken up while muscimol was present in the medium minus the amount of $^{36}$Cl$^-$ taken up when muscimol was not present.

Cl$^-$ uptake stimulated by the direct GABA$_A$ receptor agonist muscimol was similar in knockout and wild-type littermates (FIG. 15A). However, enhancement of muscimol-stimulated Cl$^-$ uptake by ethanol or flunitrazepam, a benzodiazepine, was two-fold greater in microsacs from PKCε$^{-/-}$ mice (FIG. 15B). These findings demonstrate that GABA$_A$ receptors in the frontal cortex of PKCε mutant mice are more sensitive to allosteric modulation by ethanol and benzodiazepines. This enhanced sensitivity to allosteric modulators of GABA$_A$ receptors may be due to a defect in PKCε-mediated signal transduction.

To make sure that the enhanced sensitivity to allosteric modulators of GABA$_A$ receptors of PKCε$^{-/-}$ mice is the result of impaired PKCε function in the adult mouse and is not primarily attributable to the absence of PKCε during development, muscimol-stimulated Cl$^-$ uptake was examined in wild-type microsacs treated with a selective inhibitor of PKCε, εV1-2 (J. A. Johnson, M. O. Gray, C.-H. Chen, D. Mochly-Rosen, *Journal of Biological Chemistry* 271, 24962-24966 (1996)). Microsacs were prepared from wild-type mice as described above and treated for 15 min at 4° C., in the presence or absence of 100 μM εV1-2 (EAVSLKPT) or S-εV1-2 (LSETKPAV) peptide, with a permeabilization buffer containing 140 mM KCl, 10 mM EGTA, 20 mM HEPES (pH 7.4), 50 μg/ml saponin, 5 mM sodium azide, 5 mM potassium oxalate, 6 mM ATP, and 0.2% (w/v) protease-free bovine serum albumin (Johnson, J. A et al., *J. Biol. Chem.* 271, 24962-24966 (1996)). Following centrifugation at 900× g for 15 min at 4° C., microsacs were then resuspended in assay buffer plus protease inhibitors and incubated for another 15 minutes on ice. Microsacs were then centrifuged again at 900× g for 15 min at 4° C. and re-suspended in assay buffer with protease inhibitors at 5 mg/ml immediately prior to assaying $^{36}$Cl$^-$ uptake.

Incubation with εV1-2 markedly increased the enhancing effect of flunitrazepam on muscimol-stimulated Cl$^-$ uptake, whereas incubation with a scrambled version of this peptide, S-εV1-2, had no effect (FIG. 15C). Treatment of microsacs from PKCε$^{-/-}$ mice with the PKCε inhibitor εV1-2 did not affect muscimol and flunitrazepam -stimulated $^{36}$Cl$^-$ uptake in the microsacs. These results strongly support the conclusion that absence of PKCε-mediated signaling in adult neurons is responsible for enhanced sensitivity of $GABA_A$ receptors to allosteric modulators in PKCε mutant mice.

H. Example 8

Modulation of $GABA_A$ Receptor Function in PXCε−/− Mice is Not Due to Altered Expression of Other PKC Isozymes Because mutant mice that lack PKCγ show reduced enhancement of $GABA_A$ receptor function in response to ethanol (R. A. Harris, et al., *Proc. Natl. Acad. Sci. USA* 92, 3658-3662 (1995)), it is possible that the effects of ethanol and $GABA_A$ agonists described above in PKCε$^{-/-}$ mice may be due to up-regulation of PKCγ or other PKC isozyme(s). To test this theory, Western analysis (B. Hundle, et al., *Journal of Biological Chemistry* 272, 15028-35 (1997)) of the various PKC isozymes was performed on protein samples from PKCε$^{-/-}$ mice. No alterations in levels of PKC isozymes other than PKCε were observed in PKCε$^{-/-}$ mice (FIG. 15D). Therefore, the altered responses to $GABA_A$ agonists observed in PKCε$^{-/-}$ mice appear to be due to the loss of PKCε rather than altered abundance of another PKC isoform.

I. Example 9

PKCε Affects Alcohol Withdrawal Syndrome

Since activation of $GABA_A$ receptors reduces ethanol withdrawal severity (G. D. Frye, T. J. McCown, G. R. Breese, *The Journal of Pharmacology and Experimental Therapeutics* 226, 720-725 (1983); B. R. Cooper, K. Viik, R. M. Ferris; H. L. White, *Journal of Pharmacology and Experimental Therapeutics* 209, 396403 (1979).) and PKCε mutant mice demonstrate a behavioral and biochemical profile that is consistent with enhanced GABAergic function, ethanol-induced withdrawal seizures were tested in PKCε$^{+/+}$ and PKCε$^{-/-}$ mice. Withdrawal seizures known as handling-induced convulsions (HIC) can be induced in mice by handling them after chronic exposure to ethanol. Seizure severity, as measured by a standardized HIC rating scale (TABLE II) represents a quantitative measure of ethanol dependence and withdrawal (J. C. Crabbe, C. Merrill, J. K. Belknap, *The Journal of Pharmacology and Experimental Therapeutics* 257, 663-667 (1991)). Withdrawal seizures were evaluated in 4 PKCε$^{+/+}$ and 4 PKCε$^{-/-}$ mice following two weeks exposure to a fully nutritious liquid diet containing 5% ethanol (Dyets, Bethlehem, Pa.) as the only source of food or fluid. Seizures were videotaped at 2, 4, 6, and 7 hours following removal of ethanol from the cage and rated by observers who were blind to the genotype and drug exposure. Data were averaged across time-points and mice.

As shown in FIG. 16, PKCε$^{+/+}$ mice exhibited a 50% reduction in seizure severity as compared to wildtype littermates. These data demonstrate that PKCε modulates symptoms of ethanol withdrawal and indicates that inhibitors of PKCε should allay or prevent such symptoms.

TABLE II

HIC Rating Scale[8]

| Score | Description |
| --- | --- |
| 7 | Severe, clonic-tonic convulsion with rapid onset and long duration; spontaneous or elicited by mild environmental stimuli, such as lifting the cage top |
| 6 | Severe, tonic-clonic convulsion when lifted by the tail; rapid onset and long duration, often continuing several seconds after the mouse is released |
| 5 | Tonic-clonic convulsion when lifted by the tail, onset delayed by 1-2 seconds |
| 4 | Tonic convulsion when lifted by the tail |
| 3 | Convulsion after gentle 180° spin |
| 2 | No convulsion when lifted by the tail, but tonic convulsion elicited by gentle 180° spin |
| 1 | Only facial grimace after gentle 180° spin |
| 0 | No convulsion or grimace |

[8]Reproduced from J. C. Crabbe, C. Merrill, J. K. Belknap, The Journal of Pharmacology and Experimental Therapeutics 257, 663-667 (1991)).

J. Example 10

PKCε Modulates Activity of Neurosteroids

Neurosteroids are steroid hormones that are found in brain at concentrations independent of their plasma levels. Allopregnanolone (3alpha-hydroxy-5alpha-pregnan-20-one) and allotetrahydrodeoxycorticosterone (THDOC) are neurosteroids that: 1) compete with the ligand [35S]-t-butylbicyclophosphorothionate (TBPS) for binding to $GABA_A$ receptors; 2) allosterically enhance binding of GABA and benzodiazepines to the $GABA_A$ receptor; 3) have anxiolytic and hypnotic effects when administered to rodents; 4) reduce seizures produced by agents, such as bicuculline, picrotoxin, and pentylenetetrazole, that act at $GABA_A$ receptors; and 5) do not inhibit seizures induced by the glycine receptor antagonist strychnine. Thus allopregnanolone and THDOC are endogenous allosteric modulators of $GABA_A$ receptors.

Because PKCε modulates the activity of benzodiazepines, which are non-endogenous allosteric modulators of $GABA_A$ receptors, the ability of PKCε to modulate the activity of a neurosteroid was tested. Muscimol-stimulated Cl$^-$ uptake in microsacs prepared from PKCε$^{-/-}$ mice (n=6) and PKCε$^{+/+}$ mice (n=4) was measured in the presence of different concentrations of allopregnanolone between 0 and $10^{-6}$M according to the methods described in Example 7.

As shown in FIG. 17, concentrations of allopregnanolone between $10^{-12}$M and $10^{-9}$M substantially activate $GABA_A$ receptors from PKCε$^{-/-}$ mice but have comparatively little effect on the activity of $GABA_A$ receptors from PKCε$^{+/+}$ mice. These data demonstrate that PKCε modulates the effects of a neurosteroid on $GABA_A$ receptors. Since neurosteroids are endogenous, such data indicates that inhibitors of PKCε, when administered alone (that is, without co-administration of an allosteric agonist of $GABA_A$ receptors), will increase neurosteroid-modulated $GABA_A$ receptor activity.

K. Example 11

PKCε Modulates Stress Hormone Levels

Since the experiments discussed in Example 3 demonstrated that PKCε$^{-/-}$ mice display significantly less anxiety-related behaviors than their wild-type littermates, the basal levels of stress hormones and the changes in such levels in response to anxiety-inducing conditions was determined in these mice.

Basal levels of corticosterone and adrenocorticotropic hormone (ACTH) were measured by radioimmunoassay in PKCε$^{-/-}$ mice (n=13 and 13, respectively) and PKCε$^{+/+}$ mice (n=15 and 16, respectively). Corticosterone levels were also measured in PKCε$^{-/-}$ mice and PKCε$^{+/+}$ mice immediately after and one hour after the mice were restrained for 10 minutes in a plastic sleeve, a model anxiety-inducing event (Hauger, R. L. et al., *Endocrinology* 123:396-405 (1988)).

As shown in FIGS. 18 and 19, PKCε$^{-/-}$ mice exhibited significantly (p<0.05) lower basal levels of corticosterone and ACTH, respectively, than their wild-type littermates. Corticosterone levels immediately following administration of a restraint were substantially higher than basal levels in both PKCε$^{-/-}$ mice and PKCε$^{+/+}$ mice. Although corticosterone levels were lower in PKCε$^{-/-}$ mice (n=4) than in their wild-type littermates (n=4) that this timepoint (0 hours), this difference was not significant. When corticosterone levels were measured again one hour later, they had increased slightly in PKCε$^{+/+}$ mice (n=6) and decreased substantially in PKCε$^{-/-}$ mice (n=6). The difference in corticosterone levels between mutant and wild-type mice was significant (p<0.05) at this time point (1 hour). These data demonstrate that PKCε modulates both basal levels of stress hormones and levels of such hormones during the recovery period following an anxiety-producing event. They also indicate that administration of PKCε inhibitors should diminish general anxiety and accelerate re-establishment of calm following an anxiety-producing event without impairing the ability of the recipient to respond appropriately to such events.

L. Example 12

PKCε Modulates Levels of an Inhibitory Amino Acid Neurotransmitter that is an Allosteric Agonist of GABA$_A$ Receptors The behavioral profile observed in PKCε$^{-/-}$ mice (e.g., reduced anxiety, reduced drug withdrawal, reduced alcohol self-administration, and heightened sensitivity to GABA$_A$ receptor allosteric agonists) may reflect changes in endogenous neurotransmitters or neuromodulators that mediate GABA$_A$ receptor function. To investigate this possibility, amino acid levels in the nucleus accumbens of awake, freely moving PKCε$^{-/-}$ mice and PKCε$^{+/+}$ mice were determined using the microdialysis method described below.

A concentric microdialysis probe (Jolly, D. and Vezina, P., *J. Neurosci. Methods*, 68:259-267 (1996); Robinson, T. E. and Camp, D. M., The feasibility of repeated microdialysis procedures for within-subjects design experiments: studies on the mesostriatal dopamine system. In T. E. Robinson and J. B. Justice Jr. (Eds.), Microdialysis in the Neurosciences. 7 Techniques in the Behavioral and Neural Sciences, Elsevier, Amsterdam, pp. 189-234 (1991)) was surgically implanted through a guide cannula into the nucleus accumbens of each of 6 PKCε$^{-/-}$ mice and 6 PKCε$^{+/+}$. Probes were perfused with artificial cerebrospinal fluid (aCSF), and animals were allowed to recover overnight. Mice were placed in open field chambers equipped with photobeams, and dialysis sample tubes were changed at 10 min intervals. Amino acid neurotransmitter content in the dialysis samples was quantified isocratically by HPLC with electrochemical detection (Donzanti, B. A. and Yamamoto, B. K., An improved and rapid HPLC-EC method for the isocratic separation of amino acid neurotransmitters from brain tissue and microdialysis perfusates, *Life Sci.*, 43:913-922 (1988); Gamache, P., Ryan, E., Svendsen, C., Murayama, K. and Acworth, I. N. Simultaneous measurement of monoamines, metabolites and amino acids in brain tissue and microdialysis perfusates, *J. Chromatogr. B Biomed. Appl.*, 614:213-220 (1993)).

As shown in FIG. 20, the levels of the excitatory amino acids aspartate, glutamate and glycine and the inhibitory amino acid gamma aminobutyric acid (GABA) in PKCε$^{-/-}$ mice (n=6) were not significantly different from those of their wild-type littermates (n=6). Yet, levels of the inhibitory amino acid taurine were two-fold higher in PKCε$^{-/-}$ mice than in PKCε$^{+/+}$ mice, a significant difference (p<0.05, t-test). Since taurine is an endogenous agonist of the GABA$_A$ receptor, these data demonstrate that the heightened activity of the GABA$_A$ receptor seen in PKCε$^{-/-}$ mice (see Examples 6 and 7) is due in part to increased activation of the receptor attributable to heightened taurine levels in these mice. Thus, two mechanisms for increasing GABA$_A$ receptor activity by decreasing or eliminating PKCε activity are demonstrated herein: elevated taurine levels and enhanced sensitivity of the GABA$_A$ receptor to allosteric agonists.

M. Example 13

PKCε Modulates Drug-Induced Increases in Dopamine Levels

It is well established that acute administration of ethanol or another drug of abuse results in a brief but substantial increase in the extracellular levels of dopamine in the nucleus accumbens region of the brain. This increase, which is caused by the release of dopamine from presynaptic terminals of neurons that originate in the ventral tegmental area (VTA) of the brain, is a major mediator of drug reward and the reinforcement that leads to drug dependence. In fact, following injection of dopamine receptor antagonists into the nucleus accumbens, treated animals reduce drug self-administration (Di Chiara, G., and Imperato, A., Proc. Natl. Acad. Sci. USA 85, 5274-5278 (1988)). Because the experiments discussed in Example 4 demonstrated that PKCε$^{-/-}$ mice consume significantly less alcohol than their wild-type littermates, the ability of ethanol to induce an increase in dopamine levels in the nucleus accumbens was tested.

Extracellular dopamine levels in the nucleus accumbens of awake, freely moving PKCε$^{-/-}$ mice (n=8) and PKCε$^{+/+}$ mice (n=8) were determined using the microdialysis method described in Example 12, as modified to quantitate catecholamine levels (Gobert, A., Rivet, J.-M., Audinot, V., Newman-Tancredi, A., Cistarelli, L. and Millan, M. J., Simultaneous quantification of serotonin, dopamine and noradrenaline levels in single frontal cortex dialysates of freely-moving rats reveals a complex pattern of reciprocal auto- and heteroreceptor-mediated control of release, *Neuroscience*, 84:413-429(1998)) at various timepoints following intraperitoneal injection of saline, intraperitoneal injection of 2.0 g/kg of ethanol or no treatment (basal). As shown in FIG. 21, the transient increase in dopamine levels seen in PKCε$^{+/+}$ mice following ethanol administration did not occur in PKCε$^{-/-}$ mice. No change in dopamine levels was observed in PKCε$^{-/-}$ mice after exposure to ethanol. These data show that PKCε modulates ethanol-induced increases in extracellular dopamine concentration in the nucleus accumbens. Thus, PKCε affects both an organism's ability to experience the reward associated with consuming alcohol and the amount of alcohol consumed by such organism.

The ability of acute administration of other drugs of abuse to induce transient increases in dopamine levels in the nucleus accumbens of PKCε$^{-/-}$ mice is tested by analogous methods. Results showing that PKCε$^{-/-}$ mice fail to experience such transient increases following the administration of all tested drugs of abuse would demonstrate that PKCε modulates a component of the drug reward pathway that is common to drugs of abuse. Such data, coupled with existing knowledge of the relationship between reward achievement and drug consumption, would strongly suggest that administration of PKCε inhibitors would decrease self-administration of a wide variety of drugs of abuse.

N. Example 14

PKCε Affects Consumption of, Effects of and Withdrawal from Drugs of Abuse

Because there is some evidence that the effects of drugs of abuse that cause increased release of dopamine are mediated by $GABA_A$ receptors (Dewey, S L; Morgan, A E; Ashby, C R Jr, Horan. B; Kushner, S A; Logan, J; Volkow, N D; Fowler. J S; Gardner, E L; Brodie, J D. A novel strategy for the treatment of cocaine addiction. *Synapse* 30:119-29 (1998)), the role of PKCε in modulating intake, effects and withdrawal from such drugs is tested in vivo and in vitro.

Self-administration of psychostimulants (for example, cocaine and amphetamines) and opiates (such as morphine and heroin) by $PKCε^{-/-}$ mice is compared with that of $PKCε^{+/+}$ mice. Self-administration is tested for ingestible drugs by methods analogous to those described in Example 4. Intravenous self-administration methods such as those employed by Mello et al. (Mello, N. K., Negus, S. S., Lukas, S. E., Mendelson, J. H., Sholar, J. W. & Drieze, J., A primate model of polydrug abuse: cocaine and heroin combinations, *Journal of Pharmacology and Experimental Therapeutics* 274; 1325-37 (1995)) are employed for drugs that are usually administered intravenously.

The ability of PKCε to modulate the effects of psychostimulants and opiates is examined by giving $PKCε^{-/-}$ and $PKCε^{+/+}$ mice intraperitoneal acute injections of low and high doses of the drug of interest and comparing the amount of locomotor activation or duration of loss of righting reflex caused by low and high doses, respectively, in $PKCε^{-/-}$ and $PKCε^{+/+}$ mice by the methods described in Example 5. Data showing greater sensitivity of $PKCε^{-/-}$ mice to the effects of the drug of interest would indicate that administration of inhibitors of PKCε would increase the effects of the drug and administration of enhancers of PKCε would diminish such effects.

The affect of PKCε on withdrawal syndromes of sedative-hypnotic drugs withdrawal from which causes seizures and autonomic instability is tested in $PKCε^{-/-}$ and $PKCε^{+/+}$ mice by methods analogous to those described in Example 9. Data showing significantly reduced seizure severity in $PKCε^{-/-}$ mice, relative to their wild-type littermates, would indicate that administration of inhibitors of PKCε would lessen the severity of withdrawal symptoms in individuals dependent upon such drug.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a selective inhibitor of PKCε, wherein said selective inhibitor is a fragment of PKCε and an agonist of a $GABA_A$ receptor, wherein said agonist is a benzodiazepine or barbiturate.

2. The composition of claim 1, wherein the selective inhibitor of PKCε is selected from the group consisting of εV1-1, εV1-2, εV1-3, εV1-4, εV1-5, εV1-6 and εV1-7.

3. The composition of claim 1, wherein the beuzodiazepine is selected from the group consisting of: alprazolam, chlordiazepoxide, chlordiazepoxide hydrochloride, chlormezanone, clobazam, clonazepam, clorazepate dipotassium, diazepam, droperidol, estazolam, fentanyl citrate, flurazepam hydrochloride, halazepam, lorazepam, midazolam hydrochloride, oxazepam, prazepam, quazepam, temazepam, and triazolam.

4. The composition of claim 1, wherein the barbiturate is selected from the group consisting of: amobarbital, amobarbital sodium, aprobarbital, butabarbital sodium, hexobarbital sodium, mephobarbital, metharbital, methohexital sodium, pentobarbital, pentobarbital sodium, phenobarbital, phenobarbital sodium, secobarbital, secobarbital sodium, talbutal, thiamylal sodium, and thiopental sodium.

* * * * *

UNITED STATES PATENT AND TRADEMARK OFFICE
CERTIFICATE OF CORRECTION

PATENT NO. : 7,534,859 B2
APPLICATION NO. : 11/501667
DATED : May 19, 2009
INVENTOR(S) : Messing et al.

It is certified that error appears in the above-identified patent and that said Letters Patent is hereby corrected as shown below:

In column 48, line 27, replace "beuzodiazepine" with -- benzodiazepine --.

Signed and Sealed this

First Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,534,859 B2 Page 1 of 1
APPLICATION NO. : 11/501667
DATED : May 19, 2009
INVENTOR(S) : Robert O. Messing and Clyde Hodge It is certified that error appears in the above-identified patent and that said Letters Patent is hereby corrected as shown below:

In claim 1, column 48, line 21, after "PKCϵ" insert --,--.

Signed and Sealed this

Thirty-first Day of August, 2010

David J. Kappos
*Director of the United States Patent and Trademark Office*